(12) United States Patent
Singh et al.

(10) Patent No.: US 8,802,642 B2
(45) Date of Patent: Aug. 12, 2014

(54) SPINAL MUSCULAR ATROPHY TREATMENT VIA TARGETING SMN2 CATALYTIC CORE

(75) Inventors: Ravindra Singh, Ames, IA (US); Natalia Singh, Ames, IA (US)

(73) Assignee: Iowa State University Research Foundation, Inc., Ames, IA (US)

( * ) Notice: Subject to any disclaimer, the term of this patent is extended or adjusted under 35 U.S.C. 154(b) by 82 days.

(21) Appl. No.: 13/093,958

(22) Filed: Apr. 26, 2011

(65) Prior Publication Data

US 2011/0269820 A1    Nov. 3, 2011

Related U.S. Application Data

(60) Provisional application No. 61/343,373, filed on Apr. 28, 2010.

(51) Int. Cl.
  *A61K 48/00*    (2006.01)
  *C12N 15/85*    (2006.01)
  *C07H 21/02*    (2006.01)
  *C07H 21/04*    (2006.01)

(52) U.S. Cl.
  USPC ............ 514/44; 435/325; 536/23.1; 536/24.5

(58) Field of Classification Search
  CPC ........... C12N 2310/321; C12N 15/113; C12N 2310/11
  See application file for complete search history.

(56) References Cited

U.S. PATENT DOCUMENTS 6,133,246 A * 10/2000 McKay et al. .............. 514/44 A
2007/0292408 A1   12/2007 Singh et al.

OTHER PUBLICATIONS

Hua, Yimin et al., "Antisense Masking of an hnRNP A1/A2 Intronic Splicing Silencer Corrects SMN2 Splicing in Transgenic Mice", The American Journal of Human Genetics 82, Apr. 2008, pp. 834-848.
Hua, Yimin et al., "Supplemental Data", "Antisense Masking of an hnRNP A1/A2 Intronic Splicing Silencer Corrects SMN2 Splicing in Transgenic Mice", The American Journal of Human Genetics 82, 2008, pp. 1-3.
Singh, Natalia N. et al., "A short antisense oligonucleotide masking a unique intronic motif prevents skipping of a critical exon in spinal muscular atrophy", RNA Biology 6:3, 2009, pp. 341-350.
Singh, Natalia N. et al., "An antisense microwalk reveals critical role of an intronic position linked to a unique long-distance interaction in pre-mRNA splicing", RNA (2010), pp. 1-15.
Singh, Nirmal K. et al., "Splicing of a Critical Exon of Human Survival Motor Neuron Is Regulated by a Unique Silencer element Located in the Last Intron", Molecular and Cellular Biology, Feb. 2006, vol. 26, No. 4., pp. 1333-1346.

* cited by examiner

*Primary Examiner* — Amy Bowman
(74) *Attorney, Agent, or Firm* — McKee, Voorhees & Sease

(57) ABSTRACT

The present invention is directed to methods and compositions for blocking the effect of the intronic inhibitory splicing region of intron 7 of the SMN2 gene. The compositions and methods of the instant invention include short oligonucleotide reagents (e.g., oligoribonucleotides) that effectively target sites in the SMN2 pre-mRNA, thereby modulating the splicing of SMN2 pre-mRNA to include exon 7 in the processed transcript. The short target regions are 8-mers and 5-mers and also include the identification of a single nucleotide base that is essential for initiating a long distance stearic inhibitory interactions as well as novel targets distant from intron 7 which block the intronic inhibitory splicing of the same. These short target regions and concomitant inhibitory blocking oligonucleotides are less expensive and easier to manufacture and are small enough to cross the blood brain barrier.

18 Claims, 15 Drawing Sheets

SPINAL MUSCULAR ATROPHY TREATMENT VIA TARGETING SMN2 CATALYTIC CORE

GRANT REFERENCE

This invention was made with government support under NIH Grant No. 7 R01 NS055925 awarded by the United States National Institutes of Health. The government has certain rights in the invention.

CROSS-REFERENCE TO RELATED APPLICATIONS

This application claims priority under 35 U.S.C. §119 to provisional application Ser. No. 61/343,373 filed Apr. 28, 2010, herein incorporated by reference in its entirety.

BACKGROUND OF THE INVENTION

Alternative splicing increases the coding potential of human genome by producing multiple proteins from a single gene (Black, D. L. 2003. Annu Rev. Biochem. 72:291-336). It is also associated with a growing number of human diseases (Faustino, N. A., and T. A. Cooper. 2003. Genes Dev. 17:419-437; Garcia-Blanco, M. A., et al. 2004. Nat. Biotechnol. 22:535-546; Pagani, F., and F. E. Baralle. 2004. Nat. Rev. Genet. 5:389-396).

Spinal Muscular Atrophy (SMA) is an often-fatal genetic disorder resulting from the loss of the Survival Motor Neuron (SMN) protein encoded by the Survival Motor Neuron (SMN) gene. The SMN genes, SMN1 and SMN2, are located on chromosome 5 and SMA is caused by the loss of SMN1 from both chromosomes. SMN2, while being almost identical to SMN1, is less effective at making the SMN protein. The severity of SMA is affected by the efficiency at which SMN2, of which there are several copies, produces the SMN protein.

SMN1 encodes a ubiquitously expressed 38 kDa SMN protein that is necessary for snRNP assembly, an essential process for cell survival (Wan, L., et al. 2005. Mol. Cell. Biol. 25:5543-5551). A nearly identical copy of the gene, SMN2, fails to compensate for the loss of SMN1 because of exon 7 skipping, producing an unstable truncated protein, SMNΔ7 (Lorson, C. L., et al. 1998. Nat. Genet. 19:63-66). SMN1 and SMN2 differ by a critical C to T substitution at position 6 of exon 7 (C6U in transcript of SMN2) (Lorson, C. L., et al. 1999. Proc. Natl. Acad. Sci. USA 96:6307-6311; Monani, U. R., et al. 1999. Hum. Mol. Genet. 8:1177-1183). C6U does not change the coding sequence, but is sufficient to cause exon 7 skipping in SMN1.

Current treatment for SMA consists of prevention and management of the secondary effect of chronic motor unit loss. Currently, there are no drug therapies available for the treatment or prevention of SMA.

Antisense technology, used mostly for RNA downregulation, recently has been adapted to alter the splicing process (Kole et al., Acta Biochim Pol. (2004) 51, 373-8). Techniques that trick the splicing machinery to alter splicing of SMN2 pre-mRNAs are likely to have high therapeutic value.

SUMMARY OF THE INVENTION

The present invention is based, in part, on the discovery that antisense targeting, displacement and/or disruption of an intronic sequence in the SMN2 gene can enhance production of full-length SMN2 transcripts (transcripts containing exon 7) during splicing. In particular, the present inventors have identified critical regions of the intron 7 which must be included to be work as a desirable therapeutic target. Accordingly, the invention is directed to effective use of blocking agents, targeting this critical region. According to the invention, Applicants have identified a short target comprising no more than 8 nucleotides which is effective as a therapeutic target. In another embodiment, Applicants have identified a single critical base, $^{10}$C which must be targeted and which interacts with distant sequences in a stearic fashion to repair intron splicing. Quite surprisingly, Applicants have found that this critical base, and sequences 5' thereof, which do not include any previously known target motifs work better than any targets discovered to date, and create the opportunity to generate sequences as short as 5-mers that are effective in repairing splicing. The invention thus includes, blocking oligonucleotide reagents (e.g., modified antisense oligoribonucleotides) to inhibit these critical intronic splice-inhibitory sequences. Treatment of cells derived from SMA patients with the oligonucleotide reagent compositions of the instant invention will effectively restore the production of the full-length SMN protein. These results demonstrate for the first time a stearic distant interaction between an oligonucleotide reagent and inhibition of an SMN2 splice site inhibitory domain. This distant interaction also provides a novel target site for inhibition of the intron 7 aberrant splicing and includes oligonucleotides designed to block a $^{10}$C interacting region of intron 7.

Prior work by the inventors and others had discovered the ISS-N1, CCAGCAUUAUGAAAG (SEQ ID NO:1) an intronic element that harbors two putative hnRNP A1 binding sites (CAGCAU and UGAAAG) as a primary target for SMN2. Applicants here show that much shorter targets are effective, in fact even targets that do not include either of the hnRNP A1 site, and which include sequences which are 5' of the ISS-N1 target.

The present invention therefore is directed to compositions capable of blocking the inhibitory effects of the newly-discovered SMN2 shortened and critical intronic splice silencing domain. Agents capable of blocking the splice-inhibitory effect of this domain have high value as SMA therapeutics. Featured agents capable of blocking the splice-inhibitory effect of the SMN2 shortened domain include, but are not limited to, e.g., agents that disrupt the interaction of an target domain-interacting protein with the target sequence, agents that sequester a target interacting protein, agents that disrupt the structure of the target domain and/or surrounding regions.

In exemplary embodiments, the instant invention is directed to oligonucleotide reagents (e.g., modified antisense oligoribonucleotides) that block the effect on pre-mRNA splicing of the SMN2 sequence via direct interaction and/or hybridization with the target sequence. Such RNA-complementary oligonucleotide reagents may be modified by art-recognized means to improve their in vivo stabilities and/or bioaccessibility. The instant invention also is directed to methods for identifying target domain-interacting proteins, as such methods are enabled by discovery and characterization of the target sequence.

In one aspect, the instant invention is directed to an isolated oligonucleotide reagent (e.g., an oligoribonucleotide) comprising a nucleotide sequence which is complementary to an SMN2 target comprising 8 bases or even surprisingly 5 or less bases in length and which also includes the critical $^{10}$C base in the target sequence. These shorter oligonucleotides are easier and less expensive to manufacture and are small enough to cross the blood brain barrier, making them especially beneficial for use therapeutics.

In another aspect, the instant invention is directed to an isolated oligonucleotide reagent (e.g., an oligoribonucleotide) which is complementary to the 8mer sequence 5'-CUGCCAGC-3'.

In an additional aspect, the instant invention is directed to an isolated oligonucleotide reagent (e.g., an oligoribonucleotide) which is complementary to the 5mer sequence 5'-CUGCC-3'.

In a further aspect, the instant invention is directed to an isolated oligonucleotide reagent (e.g., an oligoribonucleotide) which is complementary to a sequence which includes the $^{10}$C and sequence 5' thereof.

In another aspect, the instant invention is directed to an isolated oligonucleotide reagent (e.g., an oligoribonucleotide) which is greater than 90% complementary to the sequence 5'-5'-CUGCCAGC-3', or CUGCC.

In an additional aspect, the instant invention is directed to an isolated oligonucleotide sequence comprising the sequence 5'-GCUGGCAG-3'.

In another aspect, the instant invention is directed to an isolated oligonucleotide sequence comprising the sequence 5'-GGCAG-3'.

In another aspect, the instant invention is directed to an isolated oligonucleotide reagent comprising a sequence greater than 80% identical to the sequence 5'-GCUGGCAG-3' or 5'-GGCAG-3'.

In one embodiment, the oligonucleotide is modified by the substitution of at least one nucleotide with a modified nucleotide, such that in vivo stability is enhanced as compared to a corresponding unmodified oligonucleotide. In a related embodiment, the modified nucleotide is a sugar-modified nucleotide. In another embodiment, the modified nucleotide is a nucleobase-modified nucleotide.

In an additional embodiment, the modified nucleotide is a 2'-deoxy ribonucleotide. In certain embodiments, the 2'-deoxy ribonucleotide is 2'-deoxy adenosine or 2'-deoxy guanosine. In another embodiment, the modified nucleotide is a 2'-O-methyl (e.g., 2'-O-methylcytidine, 2'-O-methylpseudouridine, 2'-O-methylguanosine, 2'-O-methyluridine, 2'-O-methyladenosine, 2'-O-methyl)ribonucleotide. In an additional embodiment, the modified nucleotide is selected from the group consisting of a 2'-fluoro, 2'-amino and 2'-thio modified ribonucleotide. In a further embodiment, the modified nucleotide is selected from the group consisting of 2'-fluoro-cytidine, 2'-fluoro-uridine, 2'-fluoro-adenosine, 2'-fluoro-guanosine, 2'-amino-cytidine, 2'-amino-uridine, 2'-amino-adenosine, 2'-amino-guanosine and 2'-amino-butyryl-pyrene-uridine. In an additional embodiment, the modified nucleotide is selected from the group consisting of 5-bromo-uridine, 5-iodo-uridine, 5-methyl-cytidine, ribothymidine, 2-aminopurine, 5-fluoro-cytidine, and 5-fluoro-uridine, 2,6-diaminopurine, 4-thio-uridine, and 5-amino-allyl-uridine.

In a further embodiment, the modified nucleotide is a backbone-modified nucleotide. In one embodiment, the backbone-modified nucleotide contains a phosphorothioate group. In another embodiment, the modified nucleotide is a locked nucleic acid (LNA).

Another embodiment is directed to a composition comprising an oligonucleotide of the invention. In certain embodiments, the composition further comprises a pharmaceutical carrier.

An additional embodiment of the invention is directed to a method of enhancing the level of exon 7-containing SMN2 mRNA relative to exon-deleted SMN2 mRNA in a cell or cell extract, comprising contacting the cell or cell extract with an oligonucleotide (e.g., an oligoribonucleotide) of the invention, such that the level of exon 7-containing SMN2 mRNA relative to exon-deleted SMN2 mRNA in the cell or cell extract is enhanced. In one embodiment, the cell or cell extract is a spinal muscular atrophy (SMA) patient-derived neuronal cell, muscle cell or fibroblast, or extract thereof. In certain embodiments, the cell or cell extract is selected from the group consisting of an embryonic stem cell, an embryonic stem cell extract, a neuronal stem cell and a neuronal stem cell extract.

A related embodiment of the invention is directed to a method of enhancing the level of exon 7-containing SMN2 mRNA relative to exon-deleted SMN2 mRNA in an organism, comprising administering to the organism an oligonucleotide of the invention (e.g., an oligoribonucleotide), such that the level of exon 7-containing SMN2 mRNA relative to exon-deleted SMN2 mRNA in the organism is enhanced. In one embodiment, the organism is a mammal. In another embodiment, the organism is a human. In certain embodiments, the human has spinal muscular atrophy (SMA).

Another embodiment of the invention is directed to a method of treating spinal muscular atrophy (SMA) in a patient, comprising administering to the patient an oligonucleotide of the invention (e.g., an oligoribonucleotide) in a dose effective to enhance the level of exon 7-containing SMN2 mRNA relative to exon-deleted SMN2 mRNA in cells of the patient, such that SMA in the patient is treated.

A further embodiment is directed to a method for inhibiting an SMN2 pre-mRNA intronic splicing silencer site in a cell or cell extract comprising contacting the cell with an oligonucleotide of the invention (e.g., an oligoribonucleotide), such that the SMN2 intronic splicing silencer site is inhibited. In a related embodiment, the instant invention is directed to a method for inhibiting an SMN2 pre-mRNA intronic splicing silencer site in an organism comprising administering to the organism an oligonucleotide of the invention, such that the SMN2 intronic splicing silencer site is inhibited. Another embodiment is directed to a method for inhibiting an SMN2 pre-mRNA intronic splicing silencer site in a subject with SMA comprising administering to the subject an oligonucleotide of the invention (e.g., an oligoribonucleotide), such that the SMN2 intronic splicing silencer site is inhibited.

An additional aspect of the invention is directed to a method for identifying a protein that interacts with the sequences set forth as herein, SEQ ID NOS:2-5, comprising contacting a cell or cell extract with the sequence under conditions sufficient for the sequence to interact with a protein in the cell or cell extract; and isolating the sequence and interacting protein, such that the protein that interacts with the target sequence is identified. In one embodiment, the method further comprises UV-crosslinking the sequence to the interacting protein. In an additional embodiment, the cell or cell extract is of mammalian origin. In certain embodiments, the cell or cell extract is of human origin.

Another aspect of the invention is directed to a method of enhancing the level of exon 7-containing SMN2 mRNA relative to exon-deleted SMN2 mRNA in a cell or cell extract, comprising contacting the cell or cell extract with an oligonucleotide or nucleotide targeted blocking agent of the invention, such that the level of exon 7-containing SMN2 mRNA relative to exon-deleted SMN2 mRNA in the cell or cell extract is enhanced. A related aspect of the invention is directed to a method of enhancing the level of exon 7-containing SMN2 mRNA relative to exon-deleted SMN2 mRNA in an organism, comprising contacting the organism with an nucleotide SNM2 blocking agent, such that the level of exon 7-containing SMN2 mRNA relative to exon-deleted SMN2 mRNA in the organism is enhanced.

In one embodiment, the blocking agent is selected from the group consisting of a small molecule, a peptide, a polynucleotide, an antibody or biologically active portion thereof, a peptidomimetic, and a non-peptide oligomer. In an additional embodiment, the blocking agent is a small molecule.

In an additional aspect, the invention is directed to a method of treating amyotrophic lateral sclerosis (ALS) in a patient, comprising administering to the patient the oligonucleotide of the invention in a dose effective to enhance the level of exon 7-containing SMN2 mRNA relative to exon-deleted SMN2 mRNA in cells of the patient.

In an additional embodiment, the oligonucleotide reagent of the invention is a ribozyme.

Other features and advantages of the invention will be apparent from the following detailed description and claims.

The core sequence of the antisense target is highlighted in yellow. ASOs are shown as horizontal bars. Green bars represent ASOs that promote SMN2 exon 7 inclusion (exon 7 skipping is 45% and less). The intensity of green color reflects the strength of ASO stimulatory effect. Grey bars represent ASOs that have no effect on SMN2 exon 7 inclusion. Pink bars represent ASOs that promoted SMN2 exon 7 skipping (exon 7 skipping is 55% and more). To emphasize that L14 caused the most dramatic increase in exon 7 skipping, it is shown as a dark pink bar. (C) Splicing pattern of endogenous SMN2 after treatment with ASOs shown in panel B. SMA type I patient fibroblasts (GM03813) were treated with 20 nM of different ASOs and the total RNA for in vivo splicing assay was isolated 24 h post transfection. The upper band corresponds to exon 7-included product; the lower band corresponds to exon 7-skipped product. The percentage of exon skipping was calculated from the total value of exon-included and exon-skipped products. The values represent mean of three independent experiments. The standard deviations were less than 5% of mean. The effect of F14 and L14 are highlighted with green and red box, respectively. (D) Splicing pattern of endogenous SMN2 after treatment with 50 nM of indicated ASOs. The chemistry of the ASOs used is shown on the right. In vivo splicing assays were performed and analyzed as described in panel C. The values represent mean of three independent experiments. The standard deviations were less than 5% of mean.

Figure 1:
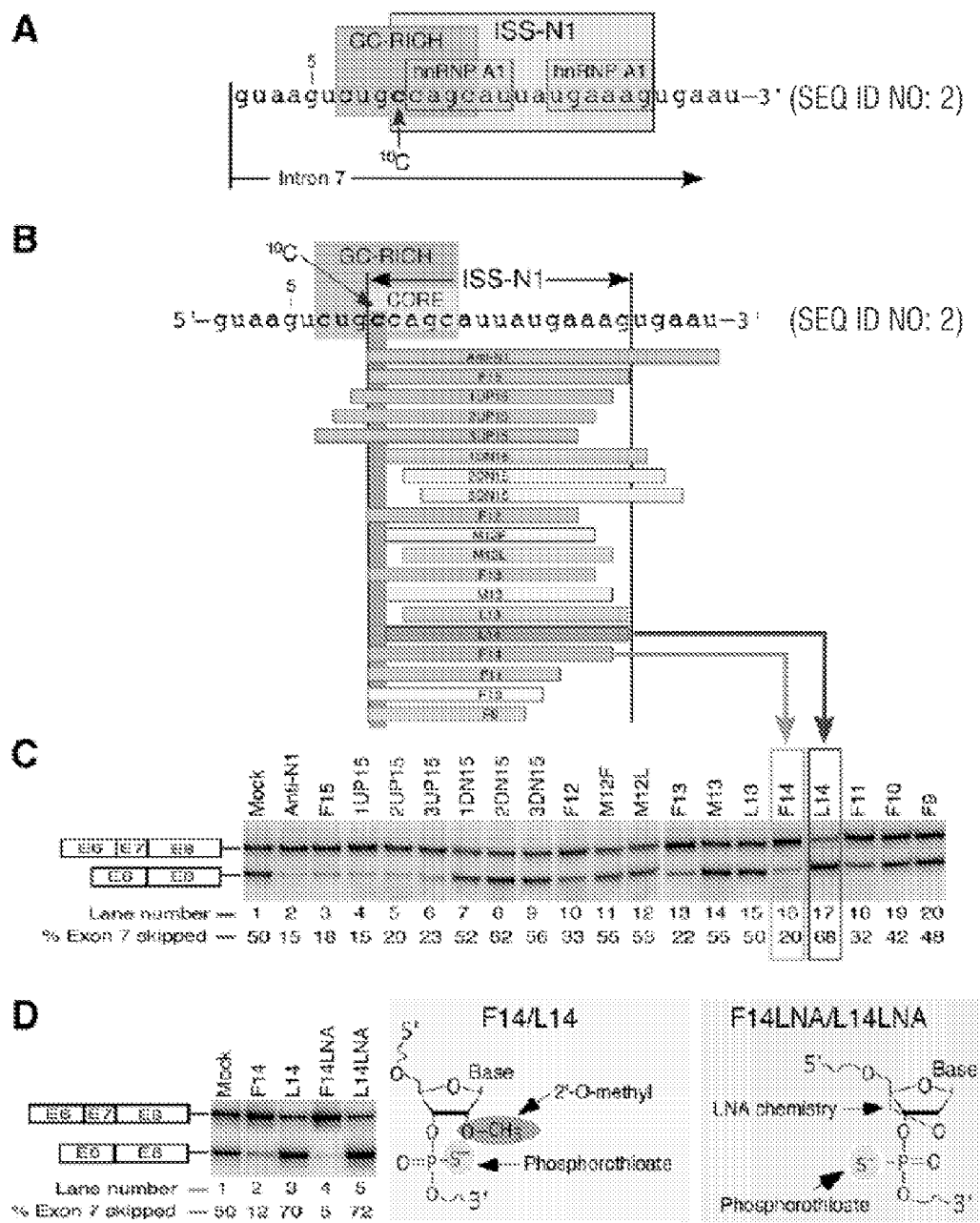
FIG. 1. An ultra-refined antisense micro-walk reveals the significance of a cytosine residue at the 10$^{th}$ position ($^{10}$C) of SMN2 exon 7. (A) Diagrammatic representation of cis-elements at the 5' end of SMN2 intron 7 (SEQ ID NO:2). ISS-N1 (SEQ ID NO:1) is highlighted in yellow with all but the first nucleotide shown in red. Two hnRNP A1 motifs are indicated as described in (Hua et al. 2008). GC-rich sequence is highlighted in green (Singh et al. 2009). Numbering of nucleotides starts from the first position of SMN2 intron 7. The location of $^{10}$C is marked by an arrow. (B) Diagrammatic representation of ASOs and their annealing positions relative to ISS-N1 region. Numbering of nucleotides starts from the first position of intron 7. Boundaries of ISS-N1 are demarcated. The first ISS-N1 residue, $^{10}$C, is highlighted in blue. The GC-rich sequence (Singh et al. 2009) is highlighted in green.
Figure 2:
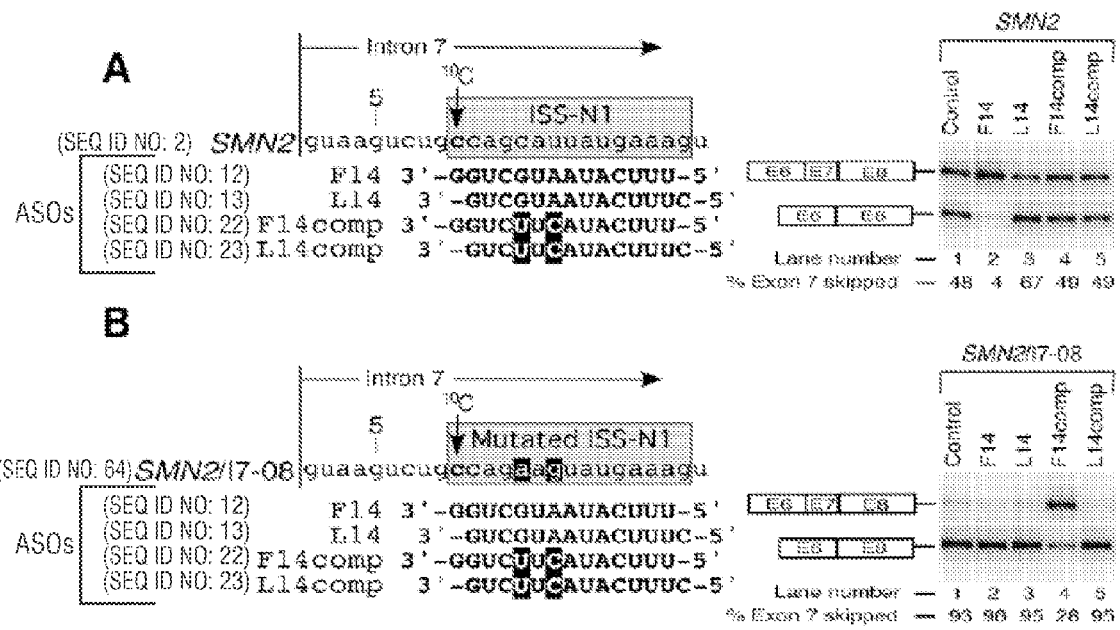

FIG. 2. Effect of ASOs are specific to their targets. (A) Diagrammatic representation of the target area in intron 7 of SMN2 minigene (SEQ ID NO:2). ISS-N1 is highlighted in light gray. Numbering of nucleotides starts from the first position of intron 7. The location of $^{10}$C is marked by an arrow. The sequences of four ASOs (F14, SEQ ID NO:12; L14, SEQ ID NO:13; F14comp, SEQ ID NO:22; L14comp, SEQ ID NO:23) and their annealing positions in ISS-N1 region are shown. Mutations are indicated in white letters and highlighted in black. Effect of ASOs on splicing of SMN2 minigene is shown on the right. HeLa cells were co-transfected with 50 nM of a given ASO and 0.1 µg of SMN2 minigene. Splicing was determined 24 h after transfection. The percentage of exon 7 skipping was calculated as described in FIG. 1C. (B) Diagrammatic representation of the target area in intron 7 of SMN2/17-08 minigene (SEQ ID NO:64). ISS-N1 is highlighted in gray. Numbering of nucleotides starts from the first position of intron 7. Location of $^{10}$C is marked by an arrow. Sequences of four ASOs and their annealing positions are shown. Mutations in ISS-N1 area as well as in the ASOs are indicated in white letters and highlighted in black. Effect of the ASOs on splicing of SMN2/17-08 minigene is shown on the right. In vivo splicing assays were performed and analyzed as described in panel A.

Figure 3:
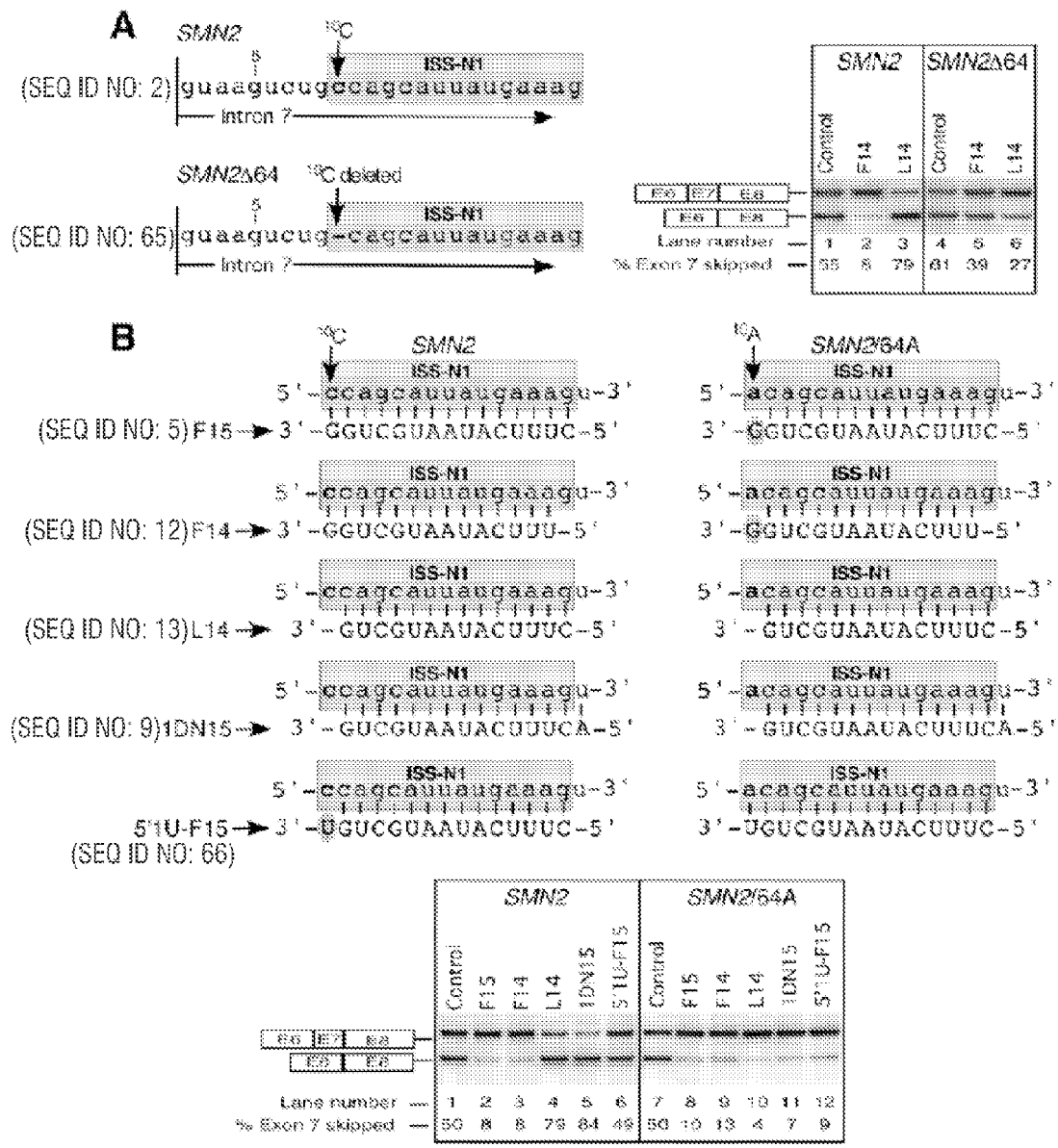

FIG. 3. Sequestration of $^{10}$C decides the outcome of antisense response. Numbering of nucleotides starts from the first intronic position. ISS-N1 sequence is highlighted in grey. The first C residue in ISS-N1 is marked as $^{10}$C. (A) Diagrammatic representation of the 5' portion of intron 7 of SMN2 minigene (SEQ ID NO:2) and its mutant, SMN2/Δ64 (SEQ ID NO:65). The location of $^{10}$C and its deletion are indicated. Effect of ASOs on splicing of wild type and mutated SMN2 minigene is shown on the right. Co-transfections and analyses were done as in (FIG. 2A). (B) Diagrammatic representation of wild type and mutated ISS-N1 targeted by different ASOs. Sequences of ASOs and their base pairing with the corresponding target are shown. F15 (SEQ ID NO:5); F14 (SEQ ID NO:12); L14 (SEQ ID NO:13); 1DN15 (SEQ ID NO:9); 5'1U-F15 (SEQ ID NO:66). Note that wild type and mutated ISS-N1 element are located within intron 7 of SMN2 and SMN2/64A minigene, respectively. Arrows mark $^{10}$C and $^{10}$A positions. The 3'-overhang of ASOs are highlighted. Effect of ASOs on splicing of SMN2 minigene and its mutant, SMN2/64A, is shown in the bottom panel. Co-transfections and splicing analyses were done as in (FIG. 2A).

Figure 4:
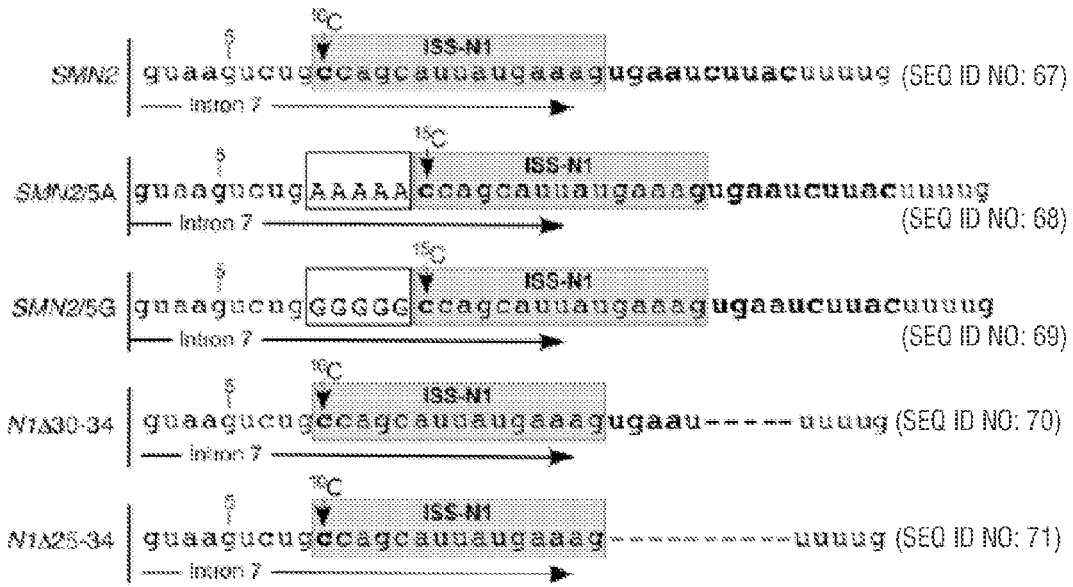
Figure 4:
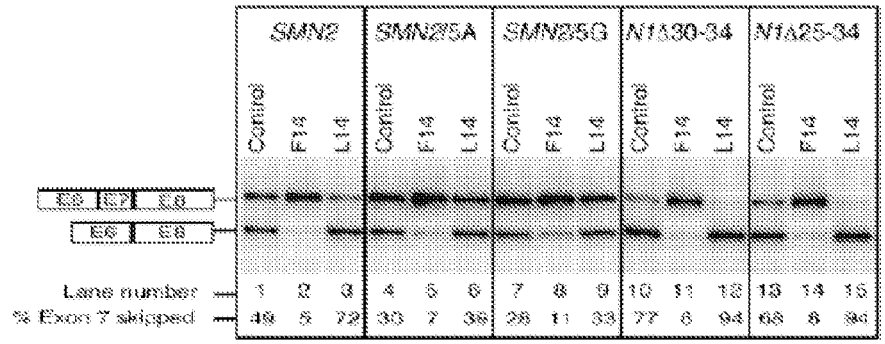

FIG. 4. Effect of the local context on antisense response of ISS-N1-targeting ASOs. (A) Diagrammatic representation of the target area in intron 7 of SMN2 minigene (SEQ ID NO:67) and its four mutants. ISS-N1 is highlighted in grey. The first C residue in ISS-N1 is marked as $^{10}$C or $^{15}$C depending on its position relative to the beginning of intron 7. Of note, numbering of intronic residues starts with the first position of intron 7. Five-nucleotide-long insertions immediately upstream of ISS-N1 in SMN2/5A (SEQ ID NO:68) or SMN2/5G (SEQ ID NO:69) minigenes are boxed and shown in capital letters. N1Δ30-34 (SEQ ID NO:70); N1Δ25-34 (SEQ ID NO:71). (B) In vivo splicing pattern of wild type and mutant SMN2 minigenes shown in panel A. The minigenes were co-transfected with an ASO of interest. Co-transfections and splicing analysis were done similarly as in (FIG. 2A).

Figure 5:
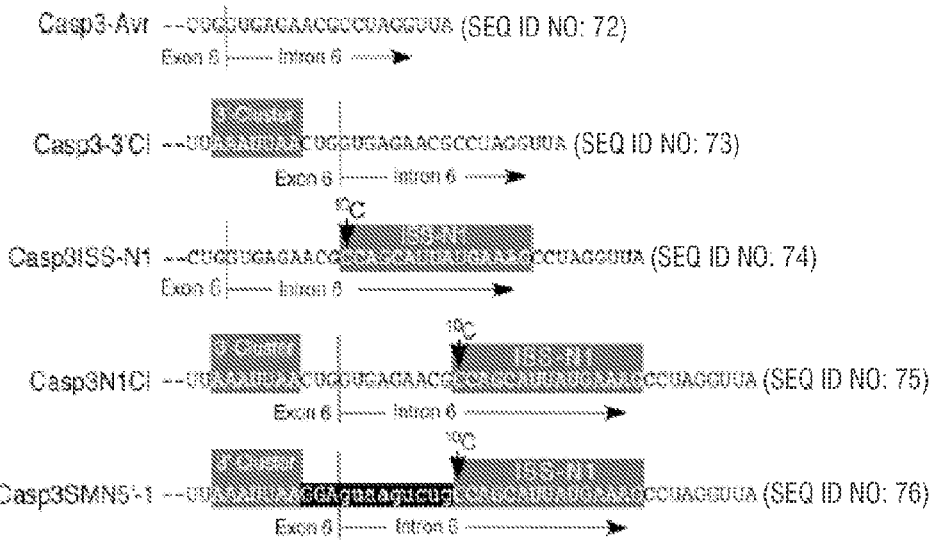
Figure 5:
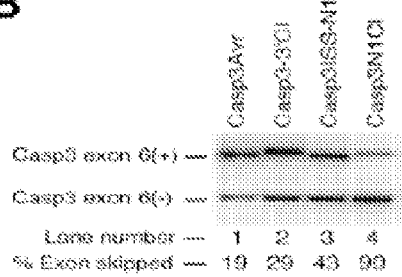
Figure 5:
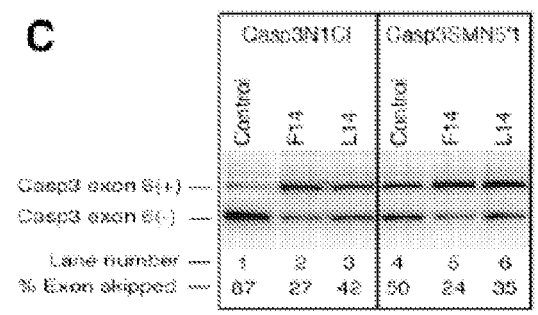
Figure 5:
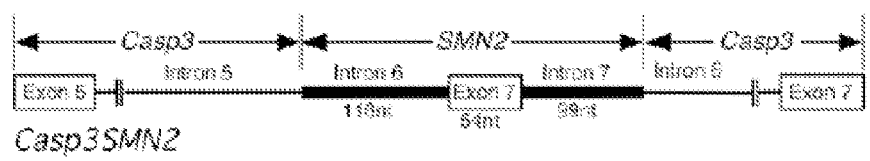
Figure 5:
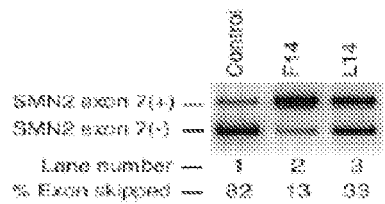

FIG. 5. Effect of the heterologous context on antisense response of ISS-N1-targeting ASOs. (A) Diagrammatic representation of exon 6/intron 6 junction in Casp3 minigene variants. 3'-Cluster and ISS-N1, which are shaded in grey, were inserted either individually or together 3-nucleotide upstream and 9-nucleotide downstream of the exon/intron junction, respectively. Casp3-Avr (SEQ ID NO:72); Casp3-3'C1 (SEQ ID NO:73); Casp3ISS-N1 (SEQ ID NO:74); CaspN1Cl (SEQ ID NO:75). In Casp3-SMN5'-1 (SEQ ID NO:76) minigene the entire region from the beginning of 3'-Cluster to the end of ISS-N1 corresponds to SMN sequence. The last three nucleotides of SMN exon 7 and the first nine nucleotides of SMN intron 7 are highlighted in black. As a result of this insertion, Casp3 exon 6 now has the 5' ss of SMN exon 7 followed by ISS-N1 element. The location of $^{10}C$ is marked by an arrow. (B) Effect of 3'-Cluster and ISS-N1 insertions on Casp3 exon 6 splicing. HeLa cells were transfected with 0.8 μg of Casp3 minigene variant and the total RNA for in vivo splicing assay was isolated 24 h post transfection. Exon 6-included and exon 6-skipped spliced products are indicated. Percentage of exon skipping was calculated from the total value of exon-included and exon-skipped products similarly as in FIG. 2. (C) In vivo splicing patterns of two Casp3 minigene variants in the presence of ASOs. Co-transfections and splicing analysis were done as in FIG. 2A. (D) In vivo splicing patterns of Casp3SMN2 minigene in the presence of ASOs. Diagram explaining the composition of this hybrid minigene is shown on the top. Co-transfections and splicing analysis were done as in panel C.

Figure 6:
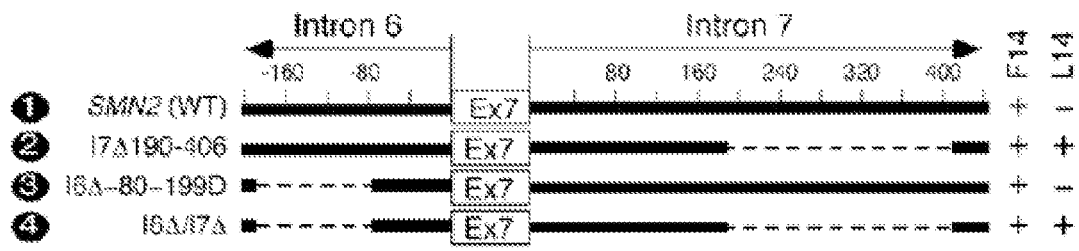
Figure 6:
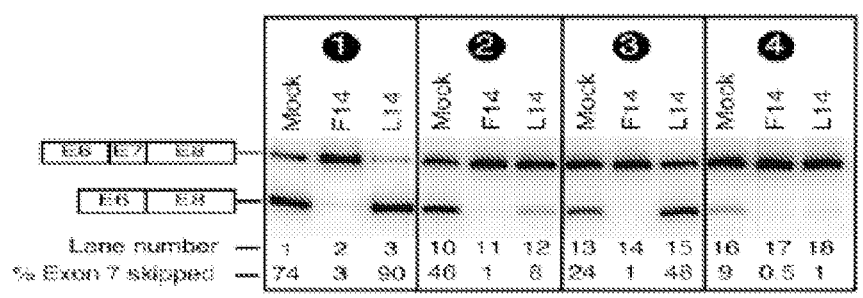

FIG. 6. Effect of deletions within intron 6 and intron 7 on antisense response of ISS-N1-targeting ASOs. (A) Diagrammatic representation of the deleted regions in intron 6 and 7 of SMN2 minigene. Deletions are represented by dotted lines. Positive numbers indicate nucleotide positions within intron 7 and start from the first position of this intron. Negative numbers indicate nucleotide positions within intron 6 and start from the last position of this intron. Names of mutants are given on the left; numbers in names reflect positions of the first and the last deleted nucleotides. A deletion mutant producing a stimulatory effect in presence of an ASO is shown as plus, whereas a mutant producing a negative effect in presence of an ASO is shown as minus. (B) In vivo splicing pattern of wild type and mutant SMN2 minigenes shown in panel A. Minigenes were co-transfected with an ASO of interest. Co-transfections and splicing analyses were done similarly as in FIG. 2A.

Figure 7:
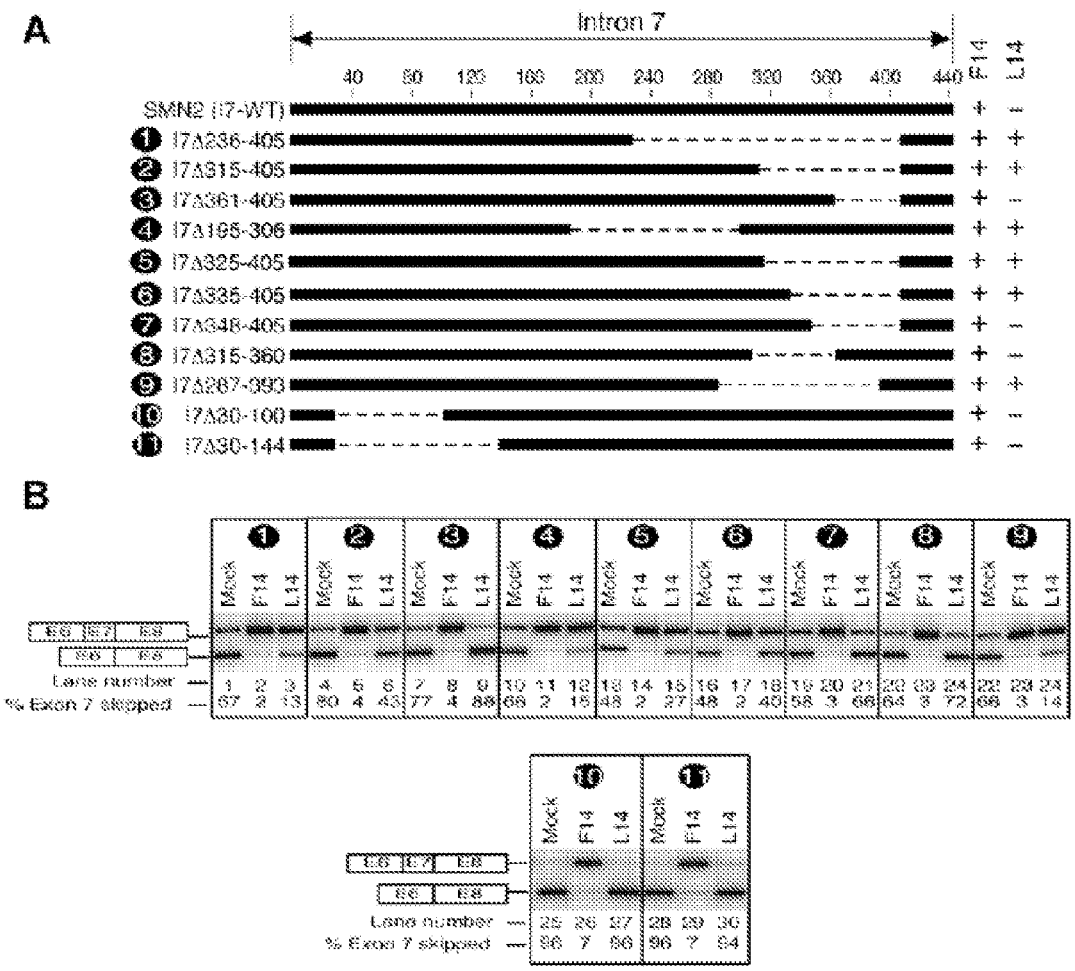

FIG. 7. Effect of deletions within intron 7 on antisense response of ISS-N1-targeting ASOs. (A) Diagrammatic representation of the deleted regions within intron 7 of SMN2 minigene. Deletions are represented by dotted lines. Numbers indicate nucleotide positions and start from the first position of intron 7. Names of mutants are given on the left; numbers in the names reflect positions of the first and the last deleted nucleotides. A deletion mutant producing a stimulatory effect in presence of an ASO is shown as plus, whereas a mutant producing a negative effect in presence of an ASO is shown as minus. (B) In vivo splicing pattern of mutant SMN2 minigenes shown in panel A. Minigenes were co-transfected with an ASO of interest. Co-transfections and splicing analysis were done similarly as in FIG. 2A.

Figure 8:
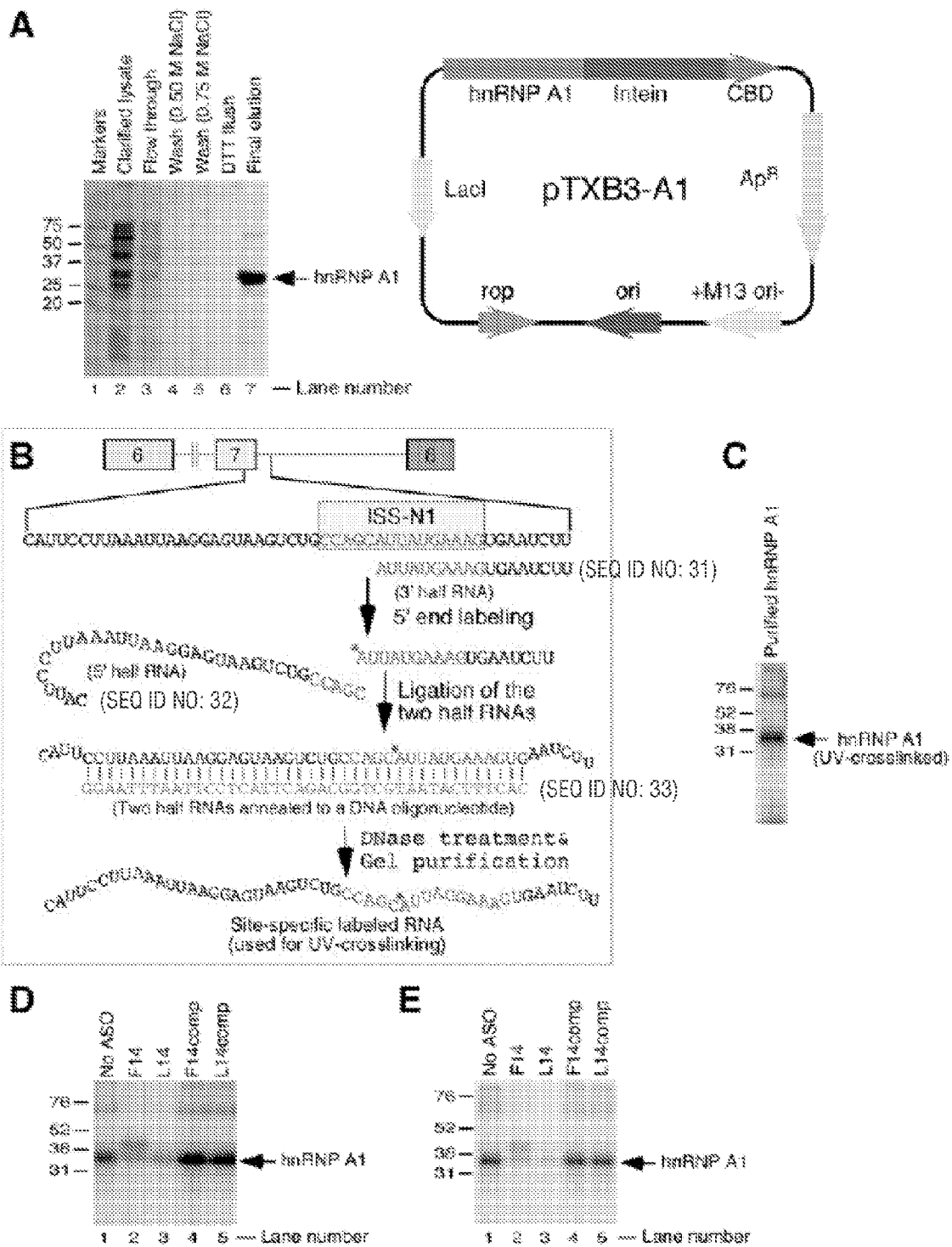

FIG. 8. Site-specific UV-crosslinking of purified recombinant hnRNP A1 with ISS-N1. (A) Purification of recombinant hnRNP A1 protein expressed from pTXB3-A1 in *E. coli* ER2566 strain. Protein was purified by binding to a chitin affinity column, followed by DTT-induced self-cleavage of the *Mycobacterium xenopi* GyrA intein. Sample aliquots were collected at different purification steps and used for SDS-polyacrylamide gel electrophoresis. Lane 1, molecular weight markers; lane 2, clarified lysate; lane 3, flow through from the column; lanes 4 & 5, wash with increasing concentration of NaCl; lane 6, DTT flush; lane 7, pooled hnRNP A1-containing fractions eluted after overnight DTT-induced intein self-cleavage at 4° C. Band corresponding to hnRNP A1 is indicated by an arrow. Right panel shows the diagrammatic representation of pTXB3-A1 construct. This construct contains hnRNP A1 ORF with a C-terminus fused in frame to the *Mycobacterium xenopi* GyrA intein/chitin binding domain (CBD). (B) Diagrammatic representation of steps for site-specific $^{32}P$-labeling of RNA probe. The sequence of probe and its relative location within SMN are given. 3' half RNA (SEQ ID NO:31); 5' half RNA (SEQ ID NO:32). ISS-N1 is highlighted in yellow and its sequence shown in red letters. Position of the $^{32}P$-radioisotope incorporation is indicated by a star. The sequence of the bridging DNA oligonucleotide (SEQ ID NO:33) is shown in green. (C) Autoradiogram showing hnRNP A1-crosslinked product. Site-specifically $^{32}P$-labeled RNA probe was UV-crosslinked with purified recombinant hnRNP A1 followed by RNase digestion and fractionation on 13% SDS-polyacrylamide gel. (D) UV-crosslinking in the presence of different ASOs under "denaturing" condition. Here, RNA probe was first refolded in the presence of a corresponding ASO to insure ASO annealing. After that the purified hnRNP A1 was added to the reaction mixture followed by UV-crosslinking Analysis of hnRNP A1-crosslinked products was done as in panel C. (E) UV-crosslinking in the presence of different ASOs under "native" condition. Here the RNA probe was denatured and refolded prior to an ASO and hnRNP A1 addition to the reaction mixture. UV-crosslinking reaction and analysis of the products were performed as in panel C.

Figure 9:
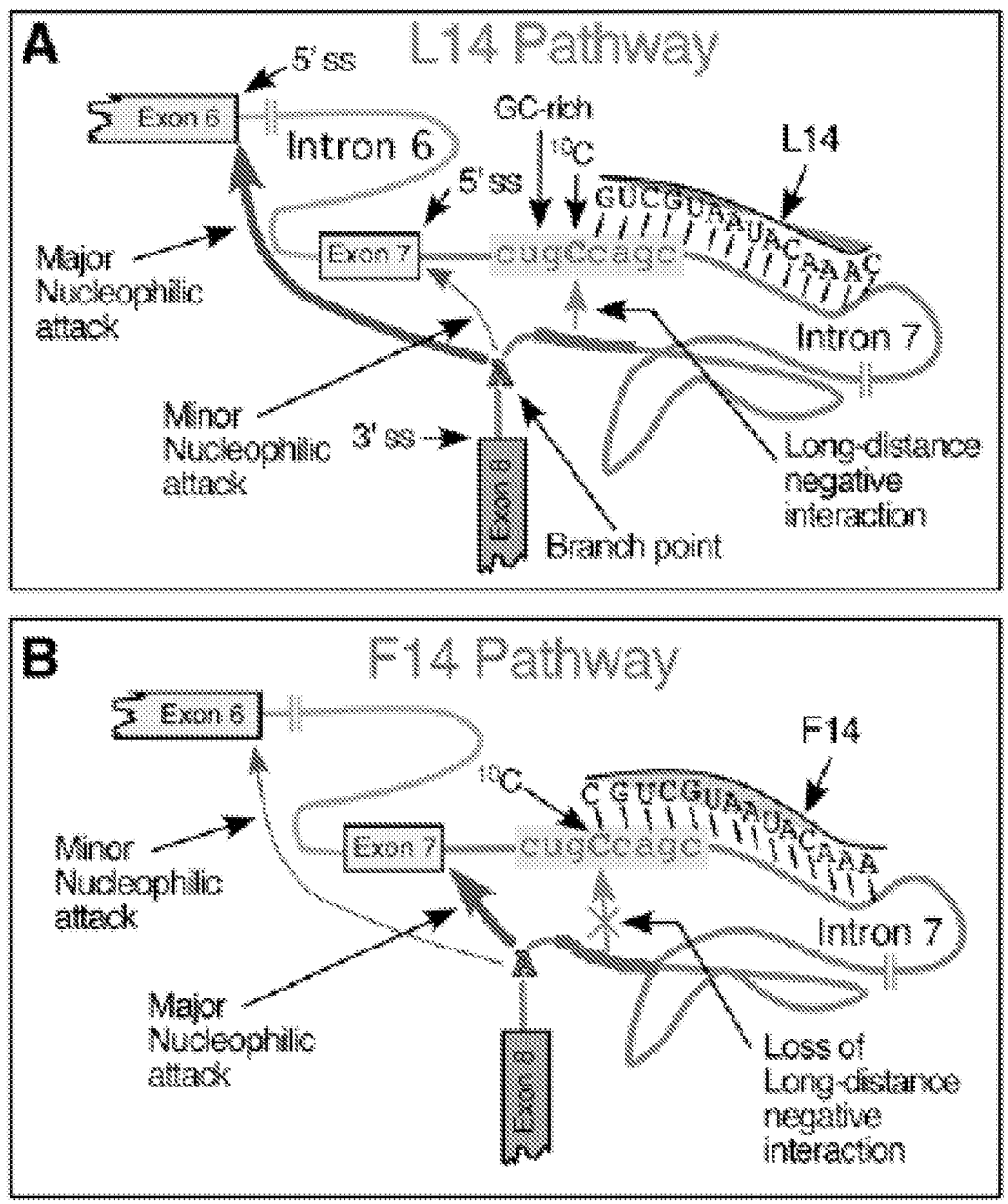

FIG. 9. Model of SMN2 exon 7 splicing modulation by $^{10}C$ in the presence of L14 and F14. (A) L14 Pathway: L14 leaves $^{10}C$ unsequestered and accessible for a long-distance interaction with intronic sequences upstream of the branch point. This arrangement interferes with the catalytic core formation at the 5' ss of exon 7. Consequently, the competing 5' ss of exon 6 becomes the favorable substrate for the transesterification reaction leading to exon 7 skipping. (B) F14 Pathway: F14 sequesters $^{10}C$ and prevents a long-distance interaction with intronic sequences upstream of the branch point. This arrangement favors catalytic core formation at the 5' ss of exon 7. Consequently, SMN2 exon 7 inclusion is promoted.

Figure 10:
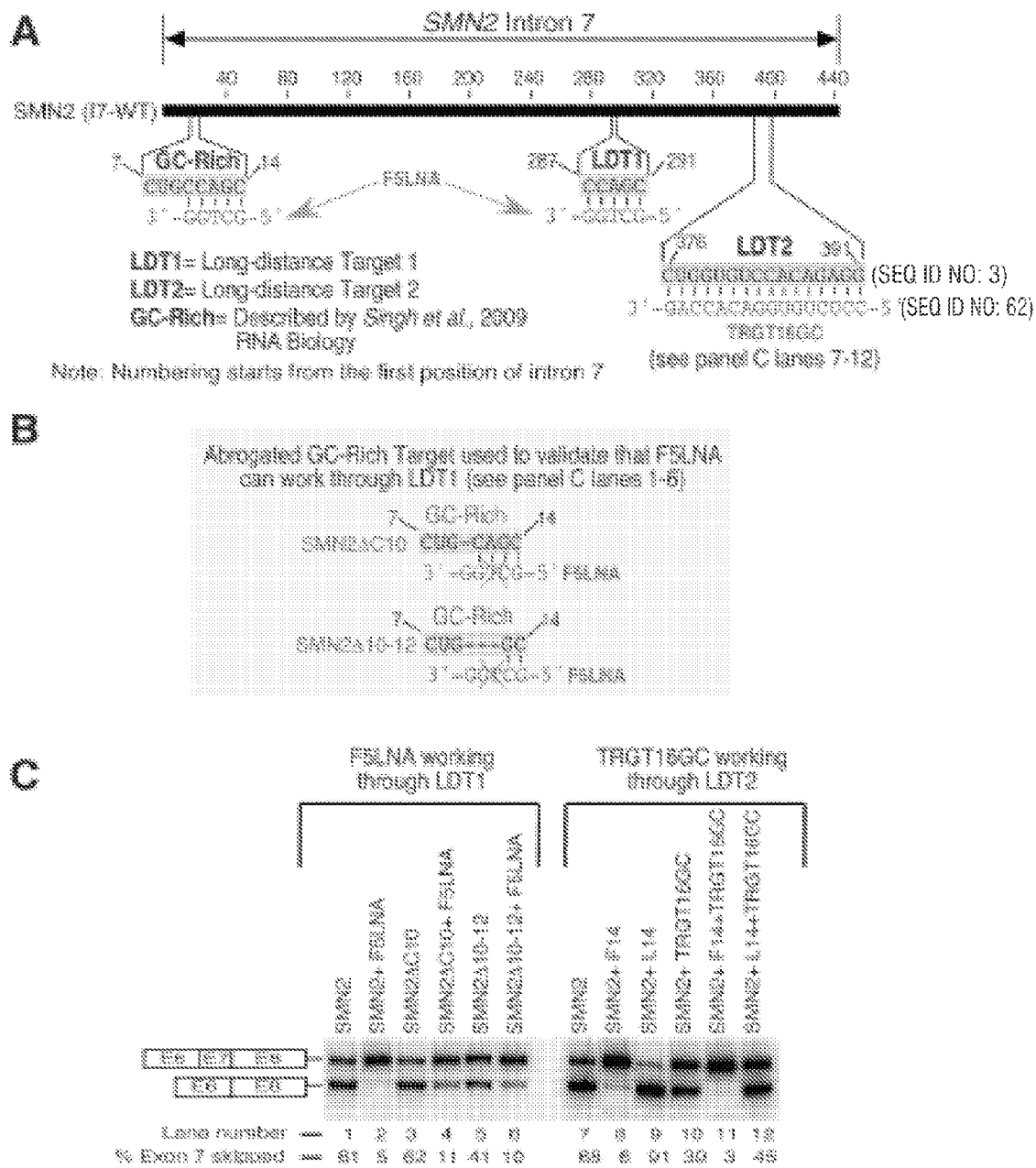

FIG. 10 is a diagram showing intron 7 and the long distance target sites for additional oligos. Long distance target 2 (LDT2) (SEQ ID NO:3); TRGT16GC (SEQ ID NO:62).

Figure 11:
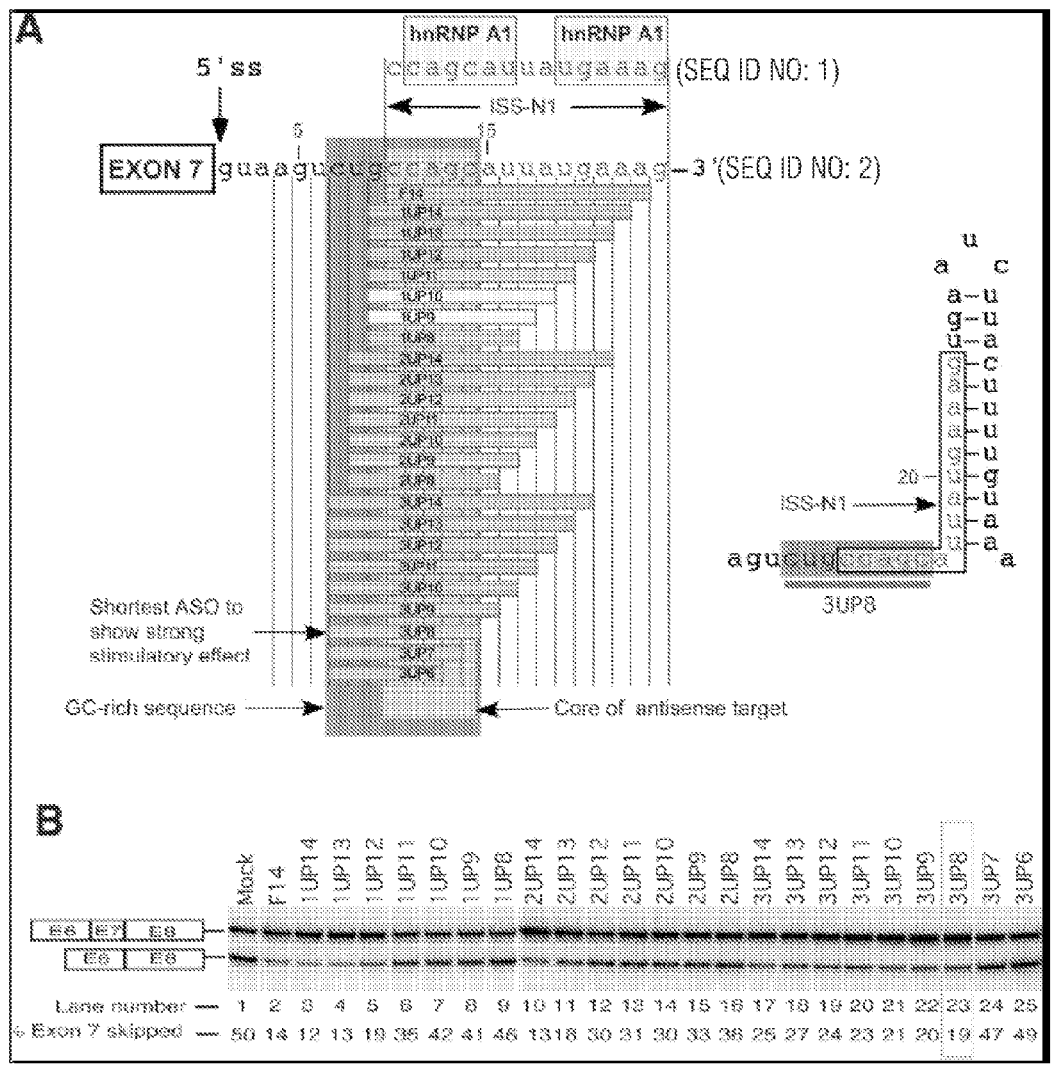

FIG. 11. Ultra-refined antisense microwalk to identify the shortest stimulatory ASO. (A) Diagrammatic representation of ASOs targeting sequences upstream of ISS-N1. Exon 7 is boxed and the first 24 residues of human SMN intron 7 (SEQ ID NO:2) are shown. Numbering starts from the first position of intron 7. The 5' ss of exon 7 is indicated by a vertical arrow. ASOs blocking different regions are shown as horizontal bars. Sequences of these ASOs are given in Table A. Boundary of ISS-N1 (SEQ ID NO:1) is demarcated. hnRNP A1 motifs are indicated. Green bars represent ASOs that promote SMN2 exon 7 inclusion. Intensity of green color reflects the strength of stimulatory effect. Tan bars represent ASOs that have no effect on SMN2 exon 7 inclusion. Area highlighted in pink represents the only GC-rich sequence in the first half of human intron 7. Area highlighted in light blue represents the core sequence of the antisense target. Right panel shows the relative positioning of ISS-N1, GC-rich sequence in the context of predicted RNA structure. Green bar represents 3UP8, the shortest ASO to stimulate SMN2 exon 7 inclusion. (B) Splicing pattern of endogenous SMN2 in SMA type I patient fibroblasts (GM03183) treated with different ASOs. Cells were transfected with 20 nM of 2OMePS ASOs and the total RNA for splicing assay was isolated 24 h post transfection. Results were analyzed as described earlier. 3UP8 was the shortest ASO to show stimulatory response (highlighted by green box).

Figure 12:
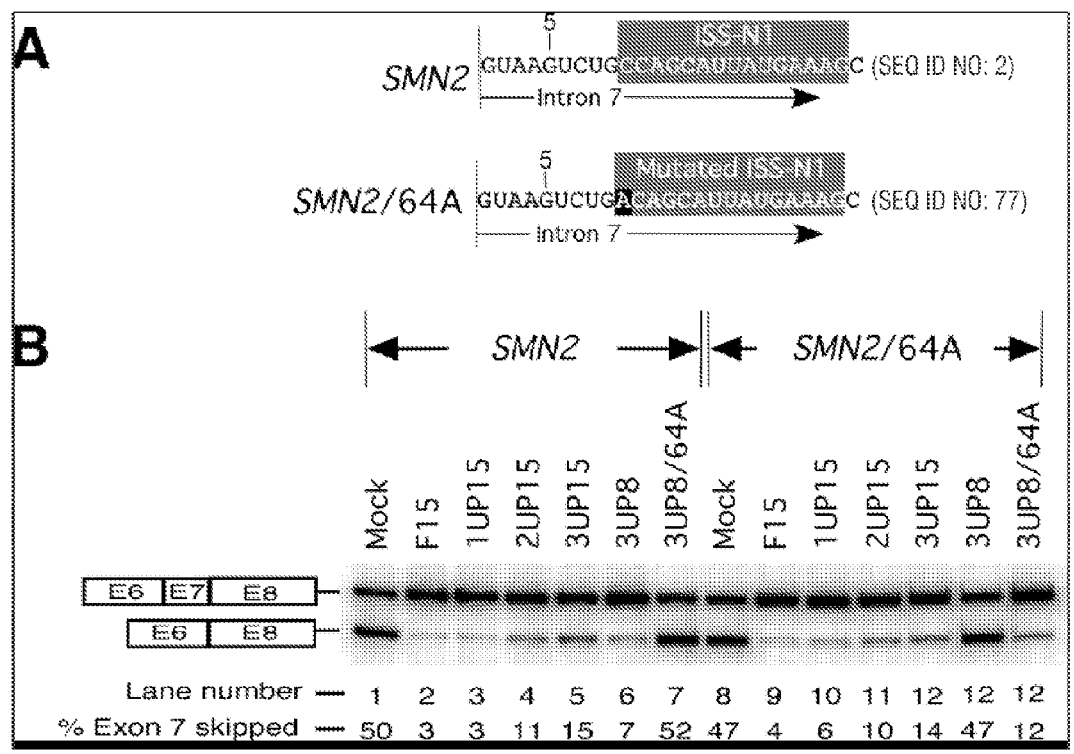

FIG. 12. Antisense effect is specific to its target sequence. (A) Diagrammatic representation of intron 7 of SMN2 minigene (SEQ ID NO:2) and its mutant, SMN2/64A (SEQ ID NO:77). Numbering starts from the first position of human SMN intron 7. ISS-N1 sequence is highlighted in gray. Mutated residue is highlighted in black. (B) Effect of ASOs on splicing of SMN2 minigene and its mutant, SMN2/64A. HeLa cells were transfected with 50 nM of a given ASO and 0.1 µg of minigene in a 24-well plate. Splicing was determined 24 h after transfection. Results were analyzed as described earlier.[35]

Figure 13:
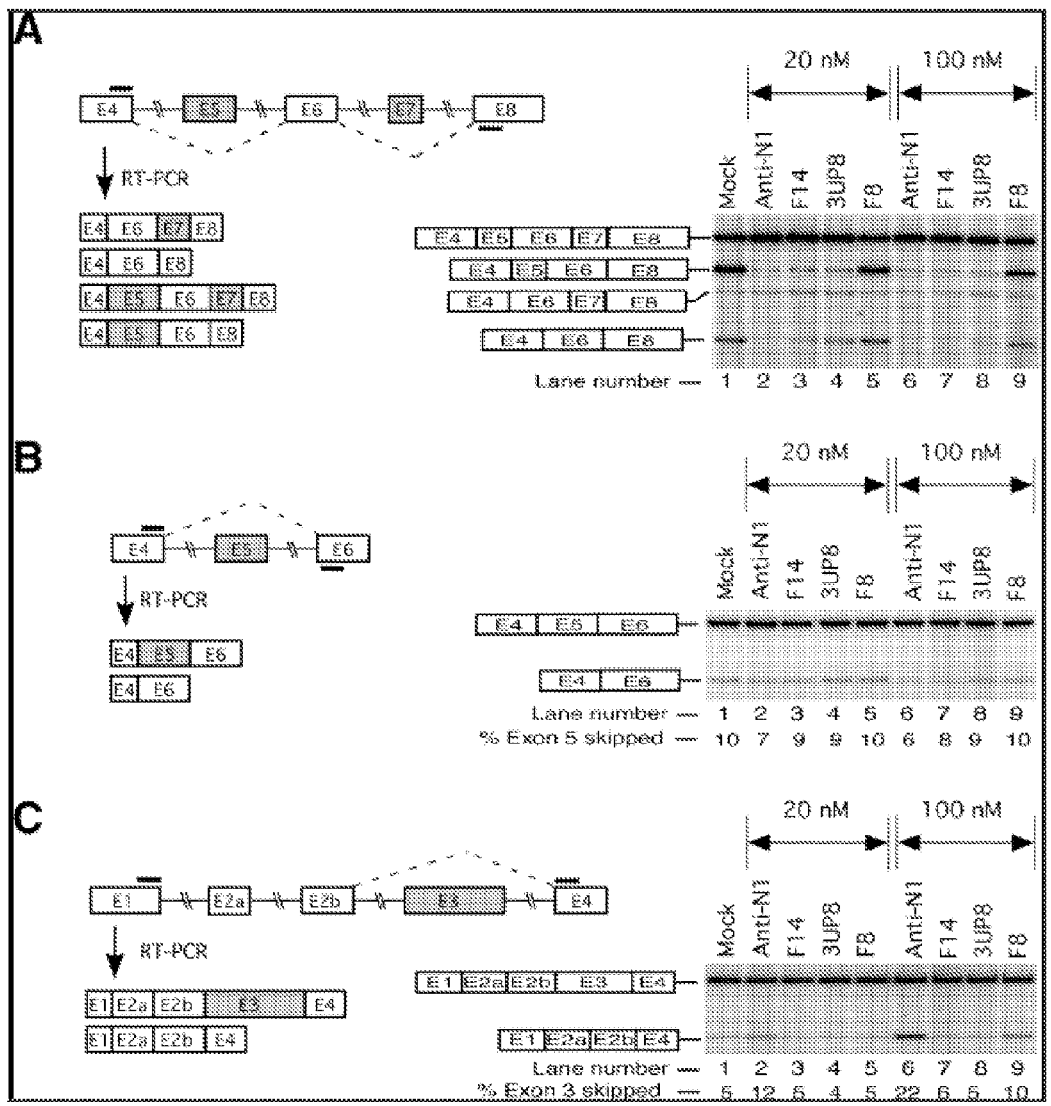

FIG. 13. Effect of ASOs on alternative splicing of different exons of endogenous SMN2. SMA type I patient fibroblasts (GM03183) were transfected with 20 or 100 nM of selected ASOs in 6-well plates. The total RNA for splicing assay was isolated 24 h post transfection. Spliced products were amplified by RT-PCR with one of the primers being end-labeled. Annealing positions of primers are shown by bars. (A) Left panel depicts the diagrammatic representation of expected spliced products. Right panel shows the results of RT-PCR. Exon 7 skipped, exon 5 skipped and co-excluded products are marked. (B) Left panel depicts the diagrammatic representation of expected spliced products due to skipping of exon 5. Right panel shows the results of RT-PCR. Exon 5 included and exon 5 skipped products are marked. (C) Left panel depicts the diagrammatic representation of expected spliced products due to skipping of exon 3. Right panel shows the results of RT-PCR. Exon 3 included and exon 3 skipped products are marked.

Figure 14:
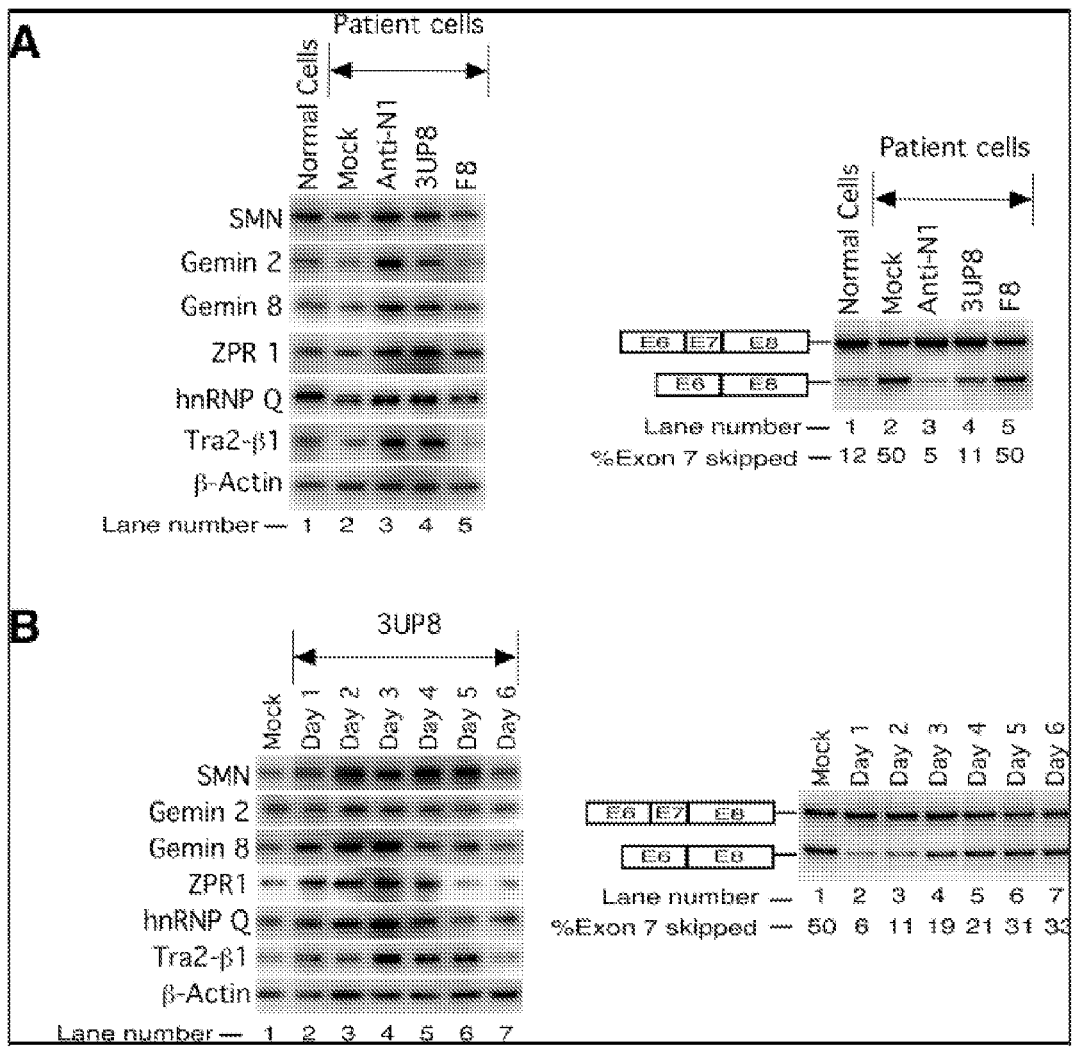

FIG. 14. Effect of the shortest stimulatory ASO (3UP8) on levels of cellular proteins in SMA patient cells. (A) Western blot showing the effect of different ASOs. SMA type I patient cells (GM03183) were transfected with 40 nM of selected ASOs and cells were harvested 48 h after transfection. Left panel represents the results of western blot of different proteins, whereas the right panel represents the results of RT-PCR. (B) Time course of 3UP8 effect on the levels of SMN and other factors. SMA type I patient cells (GM03183) were transfected with a single dose of 40 nM of 3UP8 and harvested after every 24 h for six days. Left panel represents the results of western blot of different proteins, whereas the right panel represents the results of RT-PCR.

Figure 15:
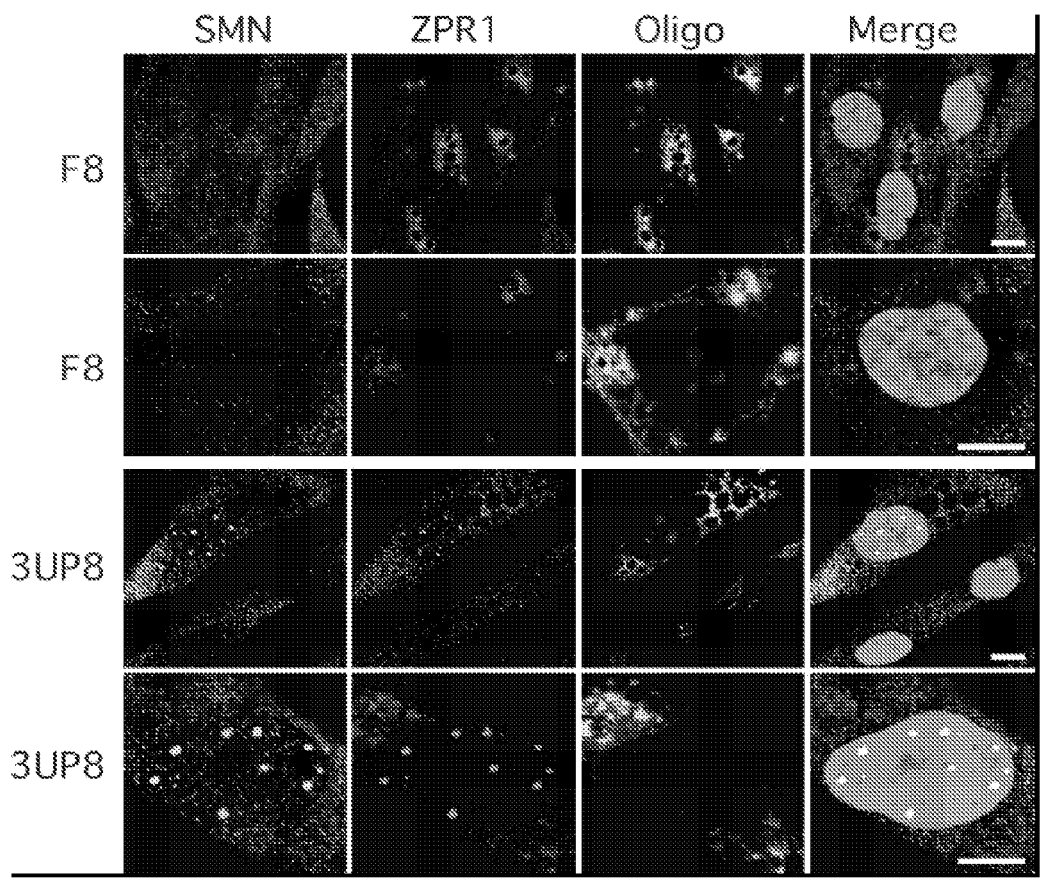

FIG. 15. Confocal images confirming that treatment with short ASO (3UP8) promotes nuclear accumulation of SMN in SMA patient cells. The fibroblasts from SMA type I patient (GM03813) were cultured on coverslips and transfected with 40 nM of F8 (control) or 3UP8 CY3-labeled ASOs. Cells were fixed 48 h after transfection and stained with anti-SMN (Green) and anti-ZPR1 (Red) antibodies. Cells transfected with ASOs were detected by Cy3 fluorescence and presented in pseudo-color (Cyan). DNA was stained with DAPI (blue). The scale bar is 10 mm.

DETAILED DESCRIPTION OF THE INVENTION

The present invention relates to the discovery that targeting of a very small regions even a single critical nucleotide within intron 7 of the SMN2 gene can enhance production of full-length SMN2 transcripts (transcripts containing exon 7) during splicing. In particular, the present inventors have identified a small target sequence and a critical single nucleotide for design of novel intronic inhibitory sequence elements. Previous targets and inhibitory sequence elements included a 15 mer named ISS-N1 (for "intronic splicing silencer"), in the SMN2 gene as a therapeutic target. This target included two hnRNP motifs that were thought to be critical for therapeutic activity of the inhibitory elements. Quite the contrary Applicants have found that much smaller targets may be used, including an 8-mer that only targets a portion of the first hnRNP motif and most surprisingly a 5-mer that includes only single base of the hnRNP A1. Instead of targeting the hnRNP A1, Applicants have identified a critical single nucleotide in intron 7 $^{10}$C. that is at the catalytic core of SMN and is critical for inhibitory activity. Applicants herein demonstrate that the inhibitory affect on unpaired $^{10}$C is dependant on a long-distance interaction involving downstream intronic sequences and represents a target design strategy for inhibiting elements that is based not a linear motif but instead on long-distance stearic interactions.

Accordingly, the invention is directed to effective use of blocking compounds, in particular, oligonucleotide reagents (e.g., modified antisense oligoribonucleotides) to inhibit this intronic splice-inhibitory sequence. The 8-mer and 5-mer and $^{10}$C. sequence motifs was identified to play a dominant role in production of exon 7-deleted SMN2 transcripts. ˆ-mer and 7mers did not produce sufficient inhibitory activity. Oligoribonucleotide reagents complementary the 5-mer and 8 mer region and those which included $^{10}$C will enhance inclusion of exon 7 during splicing of SMN2 transcript in SMA fibroblasts, thus restoring production of full-length SMN2 mRNA transcripts.

The invention is also directed to therapies that displace and/or disrupt the critical target sequences identified herein. These results demonstrated for the first time a critical single base target for long distance interaction and inhibition of SMN2 splice site inhibitory domains.

The present invention provides compositions for blocking the inhibitory effects of the SMN2 intronic splice silencing domain. In particular, the invention provides compositions comprising oligonucleotide reagents (e.g., antisense agents or dsDNA cassettes) that block the splice inhibitory effects of the intron 7 target sequences, thereby modulating splicing of the SMN2 pre-mRNA to include exon 7 in processed forms of the transcript. Agents capable of blocking the splicing effect of this region have high value as SMA therapeutics. Such agents can also be used in treatment of diseases associated with high susceptibility to oxidative stress such as exposure to Paraquat and induced Parkinson's disease, as well as amyotrophic lateral sclerosis (ALS), another neurological disease characterized by low levels of SMN protein (Veldink, J. H., et al. 2005 Neurology 65(6):820-5). The invention therefore provides small agents capable of blocking the splice-inhibitory effect of the SMN2 intron 7 which are small enough to cross the blood brain barrier, including but not limited to, e.g., agents that disrupt the interaction of an intron 7-interacting protein with the target sequences disclosed herein, agents that sequester target sequence interacting protein, agents that disrupt the structure of the target sequences herein and/or surrounding.

In exemplary embodiments, the instant invention is directed to oligonucleotide reagents capable of blocking the effect on pre-mRNA splicing of the SMN2 target sequences via direct interaction and/or hybridization. To enhance the therapeutic value of such RNA-complementary oligonucleotides, the invention is further directed to compositions comprising modified forms of such oligonucleotides, e.g., phosphorothioate-, 2'-O-methyl-, etc.-modified oligonucleotides, as such modifications have been recognized in the art as improving the stability of oligonucleotides in vivo. The instant invention also is directed to methods for identifying target sequence-interacting proteins, as such methods are enabled by the instant discovery and characterization of the critical target sequence and more specifically the single nucleotide $^{10}$C which enables long distance interaction and inhibition.

So that the invention may be more readily understood, certain terms are first defined.

The term "nucleoside" refers to a molecule having a purine or pyrimidine base covalently linked to a ribose or deoxyribose sugar. Exemplary nucleosides include adenosine, guanosine, cytidine, uridine and thymidine. The term "nucleotide" refers to a nucleoside having one or more phosphate groups joined in ester linkages to the sugar moiety. Exemplary nucleotides include nucleoside monophosphates, diphosphates and triphosphates. The terms "polynucleotide" and "nucleic acid molecule" are used interchangeably herein and refer to a polymer of nucleotides joined together by a phosphodiester linkage between 5' and 3' carbon atoms.

The term "RNA" or "RNA molecule" or "ribonucleic acid molecule" refers to a polymer of ribonucleotides. The term "DNA" or "DNA molecule" or deoxyribonucleic acid molecule" refers to a polymer of deoxyribonucleotides. DNA and RNA can be synthesized naturally (e.g., by DNA replication or transcription of DNA, respectively). RNA can be post-transcriptionally modified. DNA and RNA can also be chemically synthesized. DNA and RNA can be single-stranded (i.e., ssRNA and ssDNA, respectively) or multi-stranded (e.g., double stranded, i.e., dsRNA and dsDNA, respectively). "mRNA" or "messenger RNA" is single-stranded RNA that specifies the amino acid sequence of one or more polypeptide chains. This information is translated during protein synthesis when ribosomes bind to the mRNA.

The term "nucleotide analog" or "altered nucleotide" or "modified nucleotide" refers to a non-standard nucleotide, including non-naturally occurring ribonucleotides or deoxyribonucleotides. Preferred nucleotide analogs are modified at any position so as to alter certain chemical properties of the nucleotide yet retain the ability of the nucleotide analog to perform its intended function. Examples of positions of the nucleotide which may be derivitized include the 5 position, e.g., 5-(2-amino)propyl uridine, 5-bromo uridine, 5-propyne uridine, 5-propenyl uridine, etc.; the 6 position, e.g., 6-(2-amino)propyl uridine; the 8-position for adenosine and/or guanosines, e.g., 8-bromo guanosine, 8-chloro guanosine, 8-fluoroguanosine, etc. Nucleotide analogs also include deaza nucleotides, e.g., 7-deaza-adenosine; O- and N-modified (e.g., alkylated, e.g., N6-methyl adenosine, or as otherwise known in the art) nucleotides; and other heterocyclically modified nucleotide analogs such as those described in Herdewijn, Antisense Nucleic Acid Drug Dev., August 2000 10(4):297-310.

Nucleotide analogs may also comprise modifications to the sugar portion of the nucleotides. For example the 2' OH-group may be replaced by a group selected from H, OR, R, F, Cl, Br, I, SH, SR, $NH_2$, NHR, $NR_2$, COOR, or OR, wherein R is substituted or unsubstituted $C_1$-$C_6$ alkyl, alkenyl, alkynyl, aryl, etc. Other possible modifications include those described in U.S. Pat. Nos. 5,858,988, and 6,291,438.

The phosphate group of the nucleotide may also be modified, e.g., by substituting one or more of the oxygens of the phosphate group with sulfur (e.g., phosphorothioates), or by making other substitutions which allow the nucleotide to perform its intended function such as described in, for example, Eckstein, Antisense Nucleic Acid Drug Dev. April 2000 10(2): 117-21, Rusckowski et al. Antisense Nucleic Acid Drug Dev. October 2000 10(5):333-45, Stein, Antisense Nucleic Acid Drug Dev. October 2001 11(5): 317-25, Vorobjev et al. Antisense Nucleic Acid Drug Dev. April 2001 11(2): 77-85, and U.S. Pat. No. 5,684,143. Certain of the above-referenced modifications (e.g., phosphate group modifications) preferably decrease the rate of hydrolysis of, for example, polynucleotides comprising said analogs in vivo or in vitro.

As used herein, the term "intronic splicing silencer-N1" or "ISS-N1" refers to the 15 mer sequence 5'-CCAGCAUUAUGAAAG-3' previously known to target intron 7.

The term "oligonucleotide" refers to a short polymer of nucleotides and/or nucleotide analogs. An "oligonucleotide reagent" of the invention includes any agent, compound or composition that contains one or more oligonucleotides, and includes, e.g., reagents comprising both single stranded and/or double stranded (ds) oligonucleotide compositions, including, e.g., single stranded RNA, single stranded DNA, DNA/DNA and RNA/DNA hybrid compositions, as well as derivatized/modified compositions thereof. Such "oligonucleotide reagents" may also include amplified oligonucleotide products, e.g., polymerase chain reaction (PCR) products. An "oligonucleotide reagent" of the invention may also include art-recognized compositions designed to mimic the activity of oligonucleotides, such as peptide nucleic acid (PNA) molecules.

The term "oligoribonucleotide" refers to a short polymer of ribonucleotides and/or ribonucleotide analogs.

An "oligoribonucleotide" of the invention can include one or a few deoxyribonucleotides or deoxyribonucleotide analogs in order to enhance the stability and/or bioaccessibility of the molecule, however, the chemical nature of the entire molecule must be primarily of a ribonucleotide nature in order that ISS-N1 blocking activity occurs absent degradation of the target RNA (i.e., absent the RNase H degradation triggered by oligodeoxyribonucleotides or DNA:RNA hybridization).

Preferably, the oligonucleotide reagent molecules/agents of the invention act (or are effective) at a concentration (e.g., have an IC50) in the nanomolar range, for example, less than 500 nM, preferably less than 400 nM, more preferably less than 300, 250, 200, 150, 100, 75, 50, 25, 10, 5, 2 or 1 nM.

Preferred oligonucleotide reagent molecules/agents are modified oligonucleotides having a length of about 5 to 50 nucleotides (or nucleotide analogs), e.g., 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50 nucleotides (or nucleotide analogs). In preferred embodiments, oligonucleotide reagent molecules/agents are modified oligonucleotides having a length of about 15 to 40 nucleotides (or nucleotide analogs). In other embodiments, oligonucleotide reagent molecules/agents are modified oligonucleotides having a length of about 3 to 80 nucleotides (or nucleotide analogs), or for example, about 3-10, 10-15, 15-20, 20-25, 25-30, 30-35, 35-40, 40-45, 45-50, 50-55, 55-60, 60-65, 65-70, 70-75, 75-80 or more nucleotides (or nucleotide analogs).

The term "agent" and "compound" are used interchangeably herein.

As used herein, the term "nuclease-resistant oligonucleotide" refers to any oligonucleotide that has been modified to inhibit degradation by enzymes such as, for example, the exonucleases known to be present in the cytoplasm of a eukaryotic cell. RNA molecules (e.g., RNA oligonucleotides) are particularly at risk of degradation when combined with a composition comprising a cell extract or when introduced to a cell or organism, and a "ribonuclease-resistant" oligonucleotide is thus defined as an oligonucleotide reagent molecule/agent that is relatively resistant to ribonuclease enzymes (e.g., exonucleases), as compared to an unmodified form of the same oligonucleotide. Preferred oligonucleotide reagent molecules/agents of the invention include those that have been modified to render the oligonucleotide relatively nuclease-resistant or ribonuclease-resistant. In a preferred embodiment, the oligonucleotide reagents of the invention have been modified with a 2'-O-methyl group (e.g., 2'-O-methylcytidine, 2'-O-methylpseudouridine, 2'-O-methylguanosine, 2'-O-methyluridine, 2'-O-methyladenosine, 2'-O-methyl) and additionally comprise a phosphorothioate backbone.

The terms "2'-O-methyl modification", "phosphorothioate modification" and "locked nucleic acid" (LNA; oligonucleotides comprising at least one 2'-C,4'-C-oxy-methylene-linked bicyclic ribonucleotide monomer), as used herein, possess their art-recognized meanings.

The term "antisense" refers generally to any approach reliant upon agents, e.g., single-stranded oligonucleotides, that are sufficiently complementary to a target sequence to associate with the target sequence in a sequence-specific manner (e.g., hybridize to the target sequence). Exemplary uses of antisense in the instant application involve use of an oligoribonucleotide agent that hybridizes to a target pre-mRNA molecule and blocks an activity/effect (e.g., splicing pattern) of the targeted pre-mRNA sequence, but antisense approaches commonly are used to target DNA or RNA for transcriptional inhibition, translational inhibition, degradation, etc. Antisense is a technology that can be initiated by the hand of man, for example, to modulate splicing and/or silence the expression of target genes.

As used herein, the term "antisense oligonucleotide" refers to a nucleic acid (in preferred embodiments, an RNA) (or analog thereof), having sufficient sequence complementarity to a target RNA (i.e., the RNA for which splice site selection is modulated) to block a region of a target RNA (e.g., pre-mRNA) in an effective manner. In exemplary embodiments of the instant invention, such blocking of the ISS-N1 domain in SMN2 pre-mRNA serves to modulate splicing, either by masking a binding site for a native protein that would otherwise modulate splicing and/or by altering the structure of the targeted RNA. In preferred embodiments of the instant invention, the target RNA is a target pre-mRNA (e.g., SMN2 pre-mRNA). An antisense oligonucleotide having a "sequence sufficiently complementary to a target RNA sequence to modulate splicing of the target RNA" means that the antisense agent has a sequence sufficient to trigger the masking of a binding site for a native protein that would otherwise modulate splicing and/or alters the three-dimensional structure of the targeted RNA. Likewise, an oligonucleotide reagent having a "sequence sufficiently complementary to a target RNA sequence to modulate splicing of the target RNA" means that the oligonucleotide reagent has a sequence sufficient to trigger the masking of a binding site for a native protein that would otherwise modulate splicing and/or alters the three-dimensional structure of the targeted RNA As used herein, the terms "ISS-N1 blocking agent," "ISS-N1 blocker," and "ISS-N1 blocking compound" refer to any agent (e.g., oligonucleotide, oligoribonucleotide, small molecule, etc.) that is capable of inhibiting the effect of the SMN2 ISS-N1 site (e.g., lessen the inhibition of SMN2 exon 7 inclusion during splicing that is caused by the ISS-N1 site).

As used herein, the term "antisense strand" as it pertains to an oligonucleotide reagent refers to a strand that is substantially complementary to a section of about 10-50 nucleotides, e.g., about 15-30, 16-25, 18-23 or 19-22 nucleotides of the pre-mRNA targeted for modulation of splicing. The antisense strand has sequence sufficiently complementary to the desired target pre-mRNA sequence to direct target-specific modulation of RNA splicing (e.g., complementarity sufficient to trigger the formation of a desired target mRNA through modulation of splicing via, e.g., altered recruitment of the splicing machinery or process).

As used herein, the "5' end", as in the 5' end of an antisense strand, refers to the 5' terminal nucleotides, e.g., between one and about 5 nucleotides at the 5' terminus of the antisense strand. As used herein, the "3' end", as in the 3' end of a sense strand, refers to the region, e.g., a region of between one and about 5 nucleotides, that is complementary to the nucleotides of the 5' end of the complementary antisense strand.

An oligonucleotide reagent "that directs altered RNA splicing of a gene" is an oligonucleotide that has a sequence sufficiently complementary to the target mRNA encoded by a gene to trigger altered splicing of the target mRNA by the splicing machinery or process, or, alternatively, is an oligonucleotide reagent that displaces and/or disrupts the sequence of ISS-N1.

As used herein, the term "isolated sequence" (e.g., "isolated oligonucleotide" or "isolated oligoribonucleotide") refers to sequences which are substantially free of other cellular material, or culture medium when produced by recombinant techniques, or substantially free of chemical precursors or other chemicals when chemically synthesized.

As used herein, the term "SMA" refers to spinal muscular atrophy, a human autosomal recessive disease that is often characterized by underexpression of SMN protein in affected individuals.

The term "substituted", particularly with respect to an alkyl, alkoxy, thioalkoxy, or alkylamino group, refers to replacement of a hydrogen atom on carbon with a heteroatom-containing substituent, such as, for example, halogen, hydroxy, alkoxy, thiol, alkylthio, amino, alkylamino, imino, oxo (keto), nitro, cyano, or various acids or esters such as carboxylic, sulfonic, or phosphonic. It may also refer to replacement of a hydrogen atom on a heteroatom (such as an amine hydrogen) with an alkyl, carbonyl or other carbon containing group.

As used herein, the term "target" refers to a RNA region, and specifically, to a region identified by SEQ ID NO:1 through 5 at the 5'-termini of the mRNA of the SMN2 intron 7 region which is responsible for the deletion of exon 7 and is associated with SMN.

The term "target sequence" refers to a portion of the target RNA against which the oligonucleotide analog is directed, that is, the sequence to which the oligonucleotide analog will hybridize by Watson-Crick base pairing of a complementary sequence.

The term "targeting sequence" is the sequence in the oligonucleotide analog that is complementary (meaning, in addition, substantially complementary) to the target sequence in the RNA genome. The entire sequence, or only a portion, of the analog compound may be complementary to the target sequence. For example, in an analog having 20 bases, only 12-14 may be targeting sequences. Typically, the targeting sequence is formed of contiguous bases in the analog, but may alternatively be formed of non-contiguous sequences that when placed together, e.g., from opposite ends of the analog, constitute sequence that spans the target sequence.

Target and targeting sequences are described as "complementary" to one another when hybridization occurs in an antiparallel configuration. A targeting sequence may have "near" or "substantial" complementarity to the target sequence and still function for the purpose of the present invention, that is, still be "complementary." Preferably, the oligonucleotide analog compounds employed in the present invention have at most one mismatch with the target sequence out of 10 nucleotides, and preferably at most one mismatch out of 20. Alternatively, the antisense oligomers employed have at least 90% sequence homology, and preferably at least 95% sequence homology, with the exemplary targeting sequences as designated herein. For purposes of complementary binding to an RNA target, and as discussed below, a guanine base may be complementary to either an adenine or uracil RNA base.

An oligonucleotide analog "specifically hybridizes" to a target polynucleotide if the oligomer hybridizes to the target under physiological conditions, with a $T_m$ substantially greater than 45° C., preferably at least 50° C., and typically 60° C.-80° C. or higher. Such hybridization preferably corresponds to stringent hybridization conditions. At a given ionic strength and pH, the $T_m$ is the temperature at which 50% of a target sequence hybridizes to a complementary polynucleotide. Again, such hybridization may occur with "near" or "substantial" complementary of the antisense oligomer to the target sequence, as well as with exact complementarity.

A "nuclease-resistant" oligomeric molecule (oligomer) refers to one whose backbone is substantially resistant to nuclease cleavage, in non-hybridized or hybridized form; by common extracellular and intracellular nucleases in the body; that is, the oligomer shows little or no nuclease cleavage under normal nuclease conditions in the body to which the oligomer is exposed.

A "heteroduplex" refers to a duplex between an oligonucleotide analog and the complementary portion of a target RNA. A "nuclease-resistant heteroduplex" refers to a heteroduplex formed by the binding of an antisense oligomer to its complementary target, such that the heteroduplex is substantially resistant to in vivo degradation by intracellular and extracellular nucleases, such as RNAse H, which are capable of cutting double-stranded RNA/RNA or RNA/DNA complexes.

"Treatment" of an individual or a cell is any type of intervention provided as a means to alter the natural course of the individual or cell. Treatment includes, but is not limited to, administration of e.g., a pharmaceutical composition, and may be performed either prophylactically, or subsequent to the initiation of a pathologic event or contact with an etiologic agent. The related term "improved therapeutic outcome" relative to a patient diagnosed as infected with a particular virus, refers to a slowing or diminution in the growth of virus, or viral load, or detectable symptoms associated with infection by that particular virus.

As used herein the term "compound" includes any reagent which is tested using the assays of the invention to determine whether it modulates splice site modulation, e.g., oligonucleotide reagent-mediated splicing modulation. More than one compound, e.g., a plurality of compounds, can be tested at the same time for their ability to modulate splicing in a screening assay.

In one embodiment, test compounds comprise any selection of the group consisting of a small molecule (e.g., an organic molecule having a molecular weight of about 1000 Da or less), a peptide, a polynucleotide, an antibody or biologically active portion thereof, a peptidomimetic, and a non-peptide oligomer.

A gene "involved" in a disorder includes a gene, the normal or aberrant expression or function of which effects or causes a disease or disorder or at least one symptom of said disease or disorder.

Various methodologies of the invention include a step that involves comparing a value, level, feature, characteristic, property, etc. to a "suitable control", referred to interchangeably herein as an "appropriate control". A "suitable control" or "appropriate control" is any control or standard familiar to one of ordinary skill in the art useful for comparison purposes. In one embodiment, a "suitable control" or "appropriate control" is a value, level, feature, characteristic, property, etc. determined prior to performing an oligonucleotide reagent methodology, as described herein. For example, a transcription rate, mRNA level and/or splicing pattern, translation rate, protein level, biological activity, cellular characteristic or property, genotype, phenotype, etc. can be determined prior to introducing an oligonucleotide reagent (e.g., an oligonucleotide, compound, etc., that alters splicing of target pre-mRNA in a sequence-specific manner) of the invention into a cell or organism. In another embodiment, a "suitable control" or "appropriate control" is a value, level, feature, characteristic, property, etc. determined in a cell or organism, e.g., a control or normal cell or organism, exhibiting, for example, normal traits. In yet another embodiment, a "suitable control" or "appropriate control" is a predefined value, level, feature, characteristic, property, etc.

Various aspects of the invention are described in further detail in the following subsections.

I. Oligonucleotide Reagents and Splice Site Alteration

The present invention is directed to oligonucleotide reagents, e.g., antisense oligonucleotides, suitable for use in blocking a domain of a target RNA (in exemplary embodiments, a pre-mRNA is blocked, thereby modulating splice site selection of the mRNA splicing machinery) both in vitro and in vivo. In vivo methodologies are useful for both general splice site modulatory purposes as well as in therapeutic applications in which blocking of a target mRNA domain (e.g., enhancement of splice site selection via oligonucleotide reagent-mediated inhibition of a splice site inhibitor domain) is desirable. Oligonucleotide reagents of the invention are of any size and/or chemical composition sufficient to block a target RNA (e.g., pre-mRNA), in particular exemplary embodiments, the reagent is of any size and/or chemical composition sufficient to inhibit the intron 7 splice silencing domain of SMN2. In exemplary embodiments, the oligonucleotide reagents of the invention are oligonucleotides of between about 5-300 nucleotides (or modified nucleotides), preferably between about 10-100 nucleotides (or modified nucleotides; e.g., ribonucleotides or modified ribonucleotides), for example, between about 15-35, e.g., about 15-20, 20-25, 25-30, 30-35 (31, 32, 33, 34, 35), or 35-40 nucleotides (or modified nucleotides; e.g., ribonucleotides or modified ribonucleotides). Oligonucleotide reagents are preferably sufficiently-complementary to target RNA sequences, in particular embodiments, the short intron 7 novel domain sequence of the SMN2 pre-mRNA. In exemplary embodiments of the invention, oligonucleotide reagents comprise oligonucleotides that contain phosphorothioate and 2'-O-methyl (e.g., 2'-O-methylcytidine, 2'-O-methylpseudouridine, 2'-O-methylguanosine, 2'-O-methyluridine, 2'-O-methyladenosine, 2'-O-methyl) modifications. Many other forms of oligonucleotide modification may be used to generate oligonucleotide reagents of the instant invention, including, for example, locked nucleic acids (oligonucleotides comprising at least one 2'-C,4'-C-oxy-methylene-linked bicyclic ribonucleotide monomer), with one of skill in the art recognizing other modifications capable of rendering an oligonucleotide reagent effective for inducing inclusion of a target exon during RNA splicing (especially as relates to in vivo stability of the oligonucleotide reagents—refer to "Modifications" section below).

An oligonucleotide reagent can be, for example, about 5, 10, 15, 20, 25, 30, 35, 40, 45, or 50 or more nucleotides in length. An oligonucleotide reagent of the invention can be constructed using chemical synthesis and enzymatic ligation reactions using procedures known in the art. For example, an oligonucleotide reagent (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, e.g., phosphorothioate derivatives and acridine substituted nucleotides can be used. Examples of modified nucleotides which can be used to generate the antisense nucleic acid include 5-fluorouracil, 5-bromouracil, 5-chlorouracil, 5-iodouracil, hypoxanthine, xanthine, 4-acetylcytosine, 5-(carboxyhydroxylmethyl)uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl)uracil, (acp3)w, and 2,6-diaminopurine. Alternatively, the oligonucleotide reagent can be produced biologically using an expression vector into which a nucleic acid has been sub-cloned, e.g., in an antisense orientation (i.e., RNA transcribed from the inserted nucleic acid will be of an antisense orientation to a target nucleic acid of interest, described further in the following subsection).

The oligonucleotide reagents of the invention are typically administered to a subject or generated in situ such that they hybridize with or bind to cellular pre-mRNA and/or genomic DNA comprising an intron 7 splice silencing sequence identified herein to thereby inhibit exclusion of an exon during splicing. The hybridization can be by conventional nucleotide complementarity to form a stable duplex, or, for example, in the case of an oligonucleotide reagent which binds to DNA duplexes, through specific interactions in the major groove of the double helix. Examples of a route of administration of oligonucleotide reagents of the invention include direct injection at a tissue site or infusion of the antisense nucleic acid into an appropriately-associated body fluid, e.g., cerebrospinal fluid. Alternatively, oligonucleotide reagents can be modified to target selected cells and then administered systemically. For example, for systemic administration, oligonucleotide reagents can be modified such that they specifically bind to receptors or antigens expressed on a selected cell surface, e.g., by linking the oligonucleotide reagents to peptides or antibodies which bind to cell surface receptors or antigens. The oligonucleotide reagents can also be delivered to cells using the vectors described herein. To achieve sufficient intracellular concentrations of the oligonucleotide reagents, vector constructs in which the oligonucleotide reagent is placed under the control of a strong pol II or pol III promoter are preferred.

An oligonucleotide reagent of the invention can be an α-anomeric nucleic acid molecule. An α-anomeric nucleic acid molecule forms specific double-stranded hybrids with complementary RNA in which, contrary to the usual α-units, the strands run parallel to each other (Gaultier et al., 1987, Nucleic Acids Res. 15:6625-6641). The oligonucleotide reagent can also comprise a 2'-o-methylribonucleotide (Inoue et al., 1987, Nucleic Acids Res. 15:6131-6148) or a chimeric RNA-DNA analogue (Inoue et al., 1987, FEBS Lett. 215: 327-330).

In various embodiments, the oligonucleotide reagents of the invention can be modified at the base moiety, sugar moiety or phosphate backbone to improve, e.g., the stability, hybridization, or solubility of the molecule. For example, the deoxyribose phosphate backbone of the nucleic acid molecules can be modified to generate peptide nucleic acid molecules (see Hyrup et al., 1996, Bioorganic & Medicinal Chemistry 4(1): 5-23). As used herein, the terms "peptide nucleic acids" or "PNAs" refer to nucleic acid mimics, e.g., DNA mimics, in which the deoxyribose phosphate backbone is replaced by a pseudopeptide backbone and only the four natural nucleobases are retained. The neutral backbone of PNAs has been shown to allow for specific hybridization to DNA and RNA under conditions of low ionic strength. The synthesis of PNA oligomers can be performed using standard solid phase peptide synthesis protocols as described in Hyrup et al. (1996), supra; Perry-O'Keefe et al. (1996) Proc. Natl. Acad. Sci. USA 93:14670-675.

PNAs can be used in therapeutic and diagnostic applications. For example, PNAs can be used as antisense or antigene agents for sequence-specific modulation of gene expression by, e.g., inducing transcription or translation arrest or inhibiting replication. PNAs can also be used, e.g., in the analysis of single base pair mutations in a gene by, e.g., PNA directed PCR clamping; as artificial restriction enzymes when used in combination with other enzymes, e.g., S1 nucleases (Hyrup (1996), supra; or as probes or primers for DNA sequence and hybridization (Hyrup, 1996, supra; Perry-O'Keefe et al., 1996, Proc. Natl. Acad. Sci. USA 93:14670-675). In certain embodiments of the instant invention, PNAs can also be generated to target the critical intron 7 sequences identified herein.

In another embodiment, PNAs can be modified, e.g., to enhance their stability or cellular uptake, by attaching lipophilic or other helper groups to PNA, by the formation of PNA-DNA chimeras, or by the use of liposomes or other techniques of drug delivery known in the art. For example, PNA-DNA chimeras can be generated which can combine the advantageous properties of PNA and DNA. Such chimeras allow DNA recognition enzymes, e.g., RNASE H and DNA polymerases, to interact with the DNA portion while the PNA portion would provide high binding affinity and specificity. PNA-DNA chimeras can be linked using linkers of appropriate lengths selected in terms of base stacking, number of bonds between the nucleobases, and orientation (Hyrup, 1996, supra). The synthesis of PNA-DNA chimeras can be performed as described in Hyrup (1996), supra, and Finn et al. (1996) Nucleic Acids Res. 24(17):3357-63. For example, a DNA chain can be synthesized on a solid support using standard phosphoramidite coupling chemistry and modified nucleoside analogs. Compounds such as 5'-(4-methoxytrityl) amino-5'-deoxy-thymidine phosphoramidite can be used as a link between the PNA and the 5' end of DNA (Mag et al., 1989, Nucleic Acids Res. 17:5973-88). PNA monomers are then coupled in a step-wise manner to produce a chimeric molecule with a 5' PNA segment and a 3' DNA segment (Finn et al., 1996, Nucleic Acids Res. 24(17): 3357-63). Alternatively, chimeric molecules can be synthesized with a 5' DNA segment and a 3' PNA segment (Peterser et al., 1975, Bioorganic Med. Chem. Lett. 5: 1119-11124).

In certain embodiments of the present invention, a PNA compound that binds to a short intron 7 SMN2 target sequence can be generated additionally to contain one or more charged groups. Such tethering of charged groups to anti-intron 7 SMN2 target compounds can improve the delivery and/or activity of the anti-intron 7 SMN2 compounds of the invention, or also can be used to minimize non-specific effects potentially associated with alternative other formulations of the oligonucleotide reagents of the instant invention. In one embodiment, the oligonucleotide reagents of the invention can be generated as phosphono-PNA molecules (pPNAs), wherein one or more phosphate groups are attached to and/or incorporated into the backbone of the oligonucleotide reagent (refer to Efimov, V., et al. 2003 Nucleosides, Nucleotides & Nucleic Acids 22(5-8): 593-599, incorporated in its entirety herein by reference).

In further embodiments, the oligonucleotide reagents of the invention can be generated as GripNA™ compounds. GripNA™ molecules are a form of negatively charged PNA, which exhibit greater sequence specificity compared to conventional oligonucleotide reagents (e.g., antisense/gene silencing reagents) (refer to "Custom GripNA™ Synthesis Service" handbook (version B2, available through ActiveMotif at www.activemotif.com) and to U.S. Pat. No. 6,962,906, incorporated in its entirety herein by reference).

In additional embodiments, the oligonucleotide reagents of the invention can be generated as steroid-conjugated PNAs. For example, a steroid (e.g., glucocorticoid) dexamethasone can be linked to a PNA of the instant invention, as described in Rebuffat, A. G., et al. (FASEB J. 2002 16(11): 1426-8, the entire contents of which are incorporated herein by reference). The oligonucleotide reagents of the invention can also be produced as tricycle-DNA molecules ((tc)-DNAs) that are splice site-targeted, as described in Ittig, D., et al. (Nucleic Acids Res. 2004 32(1):346-53, the entire contents of which are incorporated herein by reference).

The oligonucleotide reagents of the invention can also be formulated as morpholino oligonucleotides. In such embodiments, the riboside moiety of each subunit of an oligonucleotide of the oligonucleotide reagent is converted to a morpholine moiety (morpholine=$C_4H_9NO$; refer to Heasman, J. 2002 Developmental Biology 243, 209-214, the entire contents of which are incorporated herein by reference).

The preceding forms of modifications can improve the delivery and/or activity of the oligonucleotide reagents of the invention, or also can be used to minimize non-specific effects potentially associated with alternative formulations of the oligonucleotide reagents of the instant invention.

In other embodiments, the oligonucleotide can include other appended groups such as peptides (e.g., for targeting host cell receptors in vivo), or agents facilitating transport across the cell membrane (see, e.g., Letsinger et al., 1989, Proc. Natl. Acad. Sci. USA 86:6553-6556; Lemaitre et al., 1987, Proc. Natl. Acad. Sci. USA 84:648-652; PCT Publication No. WO 88/09810) or the blood-brain barrier (see, e.g., PCT Publication No. WO 89/10134). In addition, oligonucleotides can be modified with hybridization-triggered cleavage agents (see, e.g., Krol et al., 1988, Bio/Techniques 6:958-976) or intercalating agents (see, e.g., Zon, 1988, Pharm. Res. 5:539-549). To this end, the oligonucleotide can be conjugated to another molecule, e.g., a peptide, hybridization triggered cross-linking agent, transport agent, hybridization-triggered cleavage agent, etc.

The invention also includes molecular beacon nucleic acid molecules having at least one region which is complementary to a nucleic acid molecule of the invention, such that the molecular beacon is useful for quantitating the presence of the nucleic acid molecule of the invention in a sample. A "molecular beacon" nucleic acid is a nucleic acid molecule comprising a pair of complementary regions and having a fluorophore and a fluorescent quencher associated therewith. The fluorophore and quencher are associated with different portions of the nucleic acid in such an orientation that when the complementary regions are annealed with one another, fluorescence of the fluorophore is quenched by the quencher. When the complementary regions of the nucleic acid molecules are not annealed with one another, fluorescence of the fluorophore is quenched to a lesser degree. Molecular beacon nucleic acid molecules are described, for example, in U.S. Pat. No. 5,876,930.

In another embodiment, oligonucleotide reagents of the invention contain sequences which naturally flank the small intron 7 target sequence (i.e., sequences located at the 5' and 3' ends of the intron 7 critical sequence) in the genomic DNA of an organism. In various embodiments, the isolated oligonucleotide agent can contain about 100 kB, 50 kB, 25 kB, 15 kB, 10 kB, 5 kB, 4 kB, 3 kB, 2 kB, 1 kB, 0.5 kB or 0.1 kB of nucleotide sequences which naturally flank the intron 7 critical target sequence in genomic DNA of the targeted cell. Moreover, an oligonucleotide reagent can be substantially free of other cellular material or culture medium when produced by recombinant techniques, or substantially free of chemical precursors or other chemicals when chemically synthesized.

The target RNA (e.g., pre-mRNA) blocking reaction guided by oligonucleotide reagents of the invention is highly sequence specific. In general, oligonucleotide reagents containing nucleotide sequences perfectly complementary to a portion of the target RNA are preferred for blocking of the target RNA. However, 100% sequence complementarity between the oligonucleotide reagent and the target RNA is not required to practice the present invention. Thus, the invention may tolerate sequence variations that might be expected due to genetic mutation, strain polymorphism, or evolutionary divergence. For example, oligonucleotide reagent sequences with insertions, deletions, and single point mutations relative to the target sequence may also be effective for inhibition. Alternatively, oligonucleotide reagent sequences with nucleotide analog substitutions or insertions can be effective for blocking.

Greater than 70% sequence identity (or complementarity), e.g., 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or even 100% sequence identity, between the oligonucleotide reagent and the target RNA, e.g., target pre-mRNA, is preferred.

In addition, variants of the short target intron 7 sequence which retain the function of same can be used in the methods of the invention. For example, a series of mutants of may be and tested for their ability to inhibit alternative splicing. In one embodiment, such variant sequences are at least about 95% identical in sequence to SEQ ID NO:3 or 4 over the entire length of the same. In another embodiment, such variant sequences are at least about 90% identical in the sequence over the entire length of the same.

Sequence identity, including determination of sequence complementarity for nucleic acid sequences, may be determined by sequence comparison and alignment algorithms known in the art. To determine the percent identity of two nucleic acid sequences (or of two amino acid sequences), the sequences are aligned for optimal comparison purposes (e.g., gaps can be introduced in the first sequence or second sequence for optimal alignment). The nucleotides (or amino acid residues) at corresponding nucleotide (or amino acid) positions are then compared. When a position in the first sequence is occupied by the same residue as the corresponding position in the second sequence, then the molecules are identical at that position. The percent identity between the two sequences is a function of the number of identical positions shared by the sequences (i.e., % homology=# of identical positions/total # of positions X 100), optionally penalizing the score for the number of gaps introduced and/or length of gaps introduced.

The comparison of sequences and determination of percent identity between two sequences can be accomplished using a mathematical algorithm. In one embodiment, the alignment generated over a certain portion of the sequence aligned having sufficient identity but not over portions having low degree of identity (i.e., a local alignment). A preferred, non-limiting example of a local alignment algorithm utilized for the comparison of sequences is the algorithm of Karlin and Altschul (1990) Proc. Natl. Acad. Sci. USA 87:2264-68, modified as in Karlin and Altschul (1993) Proc. Natl. Acad. Sci. USA 90:5873-77. Such an algorithm is incorporated into the BLAST programs (version 2.0) of Altschul, et al. (1990) J. Mol. Biol. 215:403-10.

In another embodiment, the alignment is optimized by introducing appropriate gaps and percent identity is determined over the length of the aligned sequences (i.e., a gapped alignment). To obtain gapped alignments for comparison purposes, Gapped BLAST can be utilized as described in Altschul et al., (1997) Nucleic Acids Res. 25(17):3389-3402. In another embodiment, the alignment is optimized by introducing appropriate gaps and percent identity is determined over the entire length of the sequences aligned (i.e., a global alignment). A preferred, non-limiting example of a mathematical algorithm utilized for the global comparison of sequences is the algorithm of Myers and Miller, CABIOS (1989). Such an algorithm is incorporated into the ALIGN program (version 2.0) which is part of the GCG sequence alignment software package. When utilizing the ALIGN program for comparing amino acid sequences, a PAM120 weight residue table, a gap length penalty of 12, and a gap penalty of 4 can be used.

Alternatively, the oligonucleotide reagent may be defined functionally as a nucleotide sequence (or oligonucleotide sequence) a portion of which is capable of hybridizing with the target RNA (e.g., 400 mM NaCl, 40 mM PIPES pH 6.4, 1 mM EDTA, 50° C. or 70° C. hybridization for 12-16 hours; followed by washing). Additional preferred hybridization conditions include hybridization at 70° C. in 1×SSC or 50° C. in 1×SSC, 50% formamide followed by washing at 70° C. in 0.3×SSC or hybridization at 70° C. in 4×SSC or 50° C. in 4×SSC, 50% formamide followed by washing at 67° C. in 1×SSC. The hybridization temperature for hybrids anticipated to be less than 50 base pairs in length should be 5-10° C. less than the melting temperature (Tm) of the hybrid, where Tm is determined according to the following equations. For hybrids less than 18 base pairs in length, $Tm° C.=2(\# of A+T bases)+4(\# of G+C bases)$. For hybrids between 18 and 49 base pairs in length, $Tm° C.=81.5+16.6(\log 10[Na+])+0.41(\% G+C)-(600/N)$, where N is the number of bases in the hybrid, and [Na+] is the concentration of sodium ions in the hybridization buffer ([Na+] for 1×SSC=0.165 M). Additional examples of stringency conditions for polynucleotide hybridization are provided in Sambrook, J., E. F. Fritsch, and T. Maniatis, 1989, Molecular Cloning: A Laboratory Manual, Cold Spring Harbor Laboratory Press, Cold Spring Harbor, N.Y., chapters 9 and 11, and Current Protocols in Molecular Biology, 1995, F. M. Ausubel et al., eds., John Wiley & Sons, Inc., sections 2.10 and 6.3-6.4, incorporated herein by reference. The length of the identical nucleotide sequences may be at least about 10, 12, 15, 17, 20, 22, 25, 27, 30, 32, 35, 37, 40, 42, 45, 47 or 50 bases.

Modifications

In a preferred aspect, the oligonucleotide reagents (e.g, oligoribonucleotides, such as anti-short intron 7 target oligoribonucleotides) of the present invention are modified to improve stability in serum or growth medium for cell cultures, or otherwise to enhance stability during delivery to SMA subjects and/or cell cultures. In order to enhance the stability, the 3'-residues may be stabilized against degradation, e.g., they may be selected such that they consist of purine nucleotides, particularly adenosine or guanosine nucleotides. Alternatively, substitution of pyrimidine nucleotides by modified analogues, e.g., substitution of uridine by 2'-deoxythymidine can be tolerated without affecting the efficiency of oligonucleotide reagent-induced modulation of splice site selection. For example, the absence of a 2' hydroxyl may significantly enhance the nuclease resistance of the oligonucleotide reagents in tissue culture medium.

In an especially preferred embodiment of the present invention the oligonucleotide reagents, e.g., anti-short intron 7 antisense molecules, may contain at least one modified nucleotide analogue. The nucleotide analogues may be located at positions where the target-specific activity, e.g., the splice site selection modulating activity is not substantially effected, e.g., in a region at the 5'-end and/or the 3'-end of the oligonucleotide (in preferred embodiments, oligoribonucleotide) molecule. Particularly, the ends may be stabilized by incorporating modified nucleotide analogues.

Preferred nucleotide analogues include sugar- and/or backbone-modified ribonucleotides (i.e., include modifications to the phosphate-sugar backbone). For example, the phosphodiester linkages of natural RNA may be modified to include at least one of a nitrogen or sulfur heteroatom. In preferred backbone-modified ribonucleotides the phosphoester group connecting to adjacent ribonucleotides is replaced by a modified group, e.g., of phosphothioate group. In preferred sugar-modified ribonucleotides, the 2' OH-group is replaced by a group selected from H, OR, R, halo, SH, SR, $NH_2$, NHR, $NR_2$ or ON, wherein R is $C_1$-$C_6$ alkyl, alkenyl or alkynyl and halo is F, Cl, Br or I.

Also preferred are nucleobase-modified ribonucleotides, i.e., ribonucleotides, containing at least one non-naturally occurring nucleobase instead of a naturally occurring nucleobase. Bases may be modified to block the activity of adenosine deaminase. Exemplary modified nucleobases include, but are not limited to, uridine and/or cytidine modified at the 5-position, e.g., 5-(2-amino)propyl uridine, 5-bromo uridine; adenosine and/or guanosines modified at the 8 position, e.g., 8-bromo guanosine; deaza nucleotides, e.g., 7-deaza-adenosine; O— and N-alkylated nucleotides, e.g., N6-methyl adenosine are suitable. It should be noted that the above modifications may be combined. Oligonucleotide reagents of the invention also may be modified with chemical moieties (e.g., cholesterol) that improve the in vivo pharmacological properties of the oligonucleotide reagents.

A further preferred oligonucleotide modification includes Locked Nucleic Acids (LNAs) in which the 2'-hydroxyl group is linked to the 3' or 4' carbon atom of the sugar ring thereby forming a bicyclic sugar moiety. The linkage is preferably a methelyne ($—CH_2—$)$_n$ group bridging the 2' oxygen atom and the 4' carbon atom wherein n is 1 or 2. LNAs and preparation thereof are described in WO 98/39352 and WO 99/14226, the entire contents of which are incorporated by reference herein.

Within the oligonucleotide reagents (e.g., oligoribonucleotides) of the invention, as few as one and as many as all nucleotides of the oligonucleotide can be modified. For example, a 20-mer oligonucleotide reagent (e.g., oligoribonucleotide) of the invention may contain 1, 2, 3, 4, 5, 6, 7, 8, 9, 10, 11, 12, 13, 14, 15, 16, 17, 18, 19 or 20 modified nucleotides. In preferred embodiments, the modified oligonucleotides (e.g., oligoribonucleotides) of the invention will contain as few modified nucleotides as are necessary to achieve a desired level of in vivo stability and/or bioaccessibility while maintaining cost effectiveness.

RNA molecules and oligonucleotide reagents may be produced enzymatically or by partial/total organic synthesis, any modified ribonucleotide can be introduced by in vitro enzymatic or organic synthesis. In one embodiment, an RNA molecule, e.g., oligonucleotide reagent, is prepared chemically. Methods of synthesizing RNA and DNA molecules are known in the art, in particular, the chemical synthesis methods as described in Verma and Eckstein (1998) Annul Rev. Biochem. 67:99-134. RNA can be purified from a mixture by extraction with a solvent or resin, precipitation, electrophoresis, chromatography, or a combination thereof. Alternatively, the RNA may be used with no or a minimum of purification to avoid losses due to sample processing. Alternatively, the RNA molecules, e.g., oligonucleotide reagents, can also be prepared by enzymatic transcription from synthetic DNA templates or from DNA plasmids isolated from recombinant bacteria. Typically, phage RNA polymerases are used such as T7, T3 or SP6 RNA polymerase (Milligan and Uhlenbeck (1989) Methods Enzymol. 180:51-62). The RNA may be dried for storage or dissolved in an aqueous solution. The solution may contain buffers or salts to inhibit annealing, and/or promote stabilization of the single strands.

In preferred embodiments of the invention, the target RNA of an oligonucleotide reagent specifies the amino acid sequence of SMN protein. As used herein, the phrase "specifies the amino acid sequence" of a SMN means that the mRNA sequence is translated into a SMN amino acid sequence according to the rules of the genetic code.

By blocking domains within RNAs (e.g., pre-mRNAs) capable of being translated into such proteins, valuable information regarding the function of said oligonucleotide reagent and/or proteins and therapeutic benefits of said blocking may be obtained.

Splice forms and expression levels of surveyed RNAs and proteins may be assessed by any of a wide variety of well known methods for detecting splice forms and/or expression of a transcribed nucleic acid or protein. Non-limiting examples of such methods include RT-PCR of spliced forms of RNA followed by size separation of PCR products, nucleic acid hybridization methods e.g., Northern blots and/or use of nucleic acid arrays; nucleic acid amplification methods; immunological methods for detection of proteins; protein purification methods; and protein function or activity assays.

RNA expression levels can be assessed by preparing mRNA/cDNA (i.e. a transcribed polynucleotide) from a cell, tissue or organism, and by hybridizing the mRNA/cDNA with a reference polynucleotide which is a complement of the assayed nucleic acid, or a fragment thereof. cDNA can, optionally, be amplified using any of a variety of polymerase chain reaction or in vitro transcription methods prior to hybridization with the complementary polynucleotide; preferably, it is not amplified. Expression of one or more transcripts can also be detected using quantitative PCR to assess the level of expression of the transcript(s).

In one embodiment, oligonucleotide reagents are synthesized either in vivo, in situ, or in vitro. Endogenous RNA polymerase of the cell may mediate transcription in vivo or in situ, or cloned RNA polymerase can be used for transcription in vivo or in vitro. For transcription from a transgene in vivo or an expression construct, a regulatory region (e.g., promoter, enhancer, silencer, splice donor and acceptor, polyadenylation) may be used to transcribe the oligonucleotide reagent. Production of oligonucleotide reagents may be targeted by specific transcription in an organ, tissue, or cell type; stimulation of an environmental condition (e.g., infection, stress, temperature, chemical inducers); and/or engineering transcription at a developmental stage or age. A transgenic organism that expresses an oligonucleotide reagent from a recombinant construct may be produced by introducing the construct into a zygote, an embryonic stem cell, or another multipotent cell derived from the appropriate organism.

II. Methods of Introducing RNAs, Vectors, and Host Cells

An oligonucleotide reagent construct of the present invention can be delivered to cells ex vivo or in vivo, for example, as an expression plasmid which, when transcribed in the cell, produces RNA, which is complementary to at least a unique portion of the cellular pre-mRNA which encodes an SMN protein.

Alternatively, the oligonucleotide reagent can be an oligonucleotide which is generated ex vivo and which, when introduced into the cell, causes inhibition of expression by hybridizing with the pre-mRNA, mRNA and/or genomic sequences of the SMN2 gene. Such oligonucleotides are preferably modified oligonucleotides, which are resistant to endogenous nucleases, e.g. exonucleases and/or endonucleases, and are therefore stable in vivo. Exemplary nucleic acid molecules for use as antisense oligonucleotides are phosphoramidate, phosphothioate and methylphosphonate analogs of oligonucleotide (see also U.S. Pat. Nos. 5,176,996, 5,294,564 and 5,256,775, which are herein incorporated by reference).

Oligonucleotide sequences can be introduced into cells as is known in the art. Transfection, electroporation, fusion, liposomes, colloidal polymeric particles and viral and non-viral vectors as well as other means known in the art may be used to deliver the oligonucleotide sequences to the cell. The method of delivery selected will depend at least on the cells to be treated and the location of the cells and will be known to those skilled in the art. Localization can be achieved by liposomes, having specific markers on the surface for directing the liposome, by having injection directly into the tissue containing the target cells, by having depot associated in spatial proximity with the target cells, specific receptor mediated uptake, viral vectors, or the like.

In certain embodiments, ribozymes can be used to deliver oligonucleotide reagents of the invention directed against short intron 7 target sequences (including functional variants of the same) to a necessary site within a given intron. Ribozyme design is an art-recognized process, described, e.g., in U.S. Pat. No. 6,770,633, the entire contents of which are incorporated by reference herein.

Physical methods of introducing nucleic acids include injection of a solution containing the RNA, bombardment by particles covered by the RNA, soaking the cell or organism in a solution of the RNA, or electroporation of cell membranes in the presence of the RNA. A viral construct packaged into a viral particle would accomplish both efficient introduction of an expression construct into the cell and transcription of RNA encoded by the expression construct. Other methods known in the art for introducing nucleic acids to cells may be used, such as lipid-mediated carrier transport, chemical-mediated transport, such as calcium phosphate, and the like. Thus the RNA may be introduced along with components that perform one or more of the following activities: enhance RNA uptake by the cell, inhibit annealing of single strands, stabilize the single strands, or other-wise increase inhibition of the target gene.

As described supra and in the art, oligonucleotide reagents may be delivered using, e.g., methods involving liposome-mediated uptake, lipid conjugates, polylysine-mediated uptake, nanoparticle-mediated uptake, and receptor-mediated endocytosis, as well as additional non-endocytic modes of delivery, such as microinjection, permeabilization (e.g., streptolysin-O permeabilization, anionic peptide permeabilization), electroporation, and various non-invasive non-endocytic methods of delivery that are known in the art (refer to Dokka and Rojanasakul, Advanced Drug Delivery Reviews 44, 35-49, incorporated in its entirety herein by reference).

Oligonucleotide reagents may be directly introduced into the cell (i.e., intracellularly); or introduced extracellularly into a cavity, interstitial space, into the circulation of an organism, introduced orally, or may be introduced by bathing a cell or organism in a solution containing the RNA using methods known in the art for introducing nucleic acid (e.g., DNA) into cells in vivo. Vascular or extravascular circulation, the blood or lymph system, and the cerebrospinal fluid are sites where the RNA may be introduced.

The present invention also provides vectors comprising an expression control sequence operatively linked to the oligonucleotide sequences of the invention. The present invention further provides host cells, selected from suitable eukaryotic and prokaryotic cells, which are transformed with these vectors as necessary. Such transformed cells allow the study of the function and the regulation of malignancy and the treatment therapy of the present invention.

Vectors are known or can be constructed by those skilled in the art and should contain all expression elements necessary to achieve the desired transcription of the sequences. Other beneficial characteristics can also be contained within the vectors such as mechanisms for recovery of the oligonucleotides in a different form. Phagemids are a specific example of such beneficial vectors because they can be used either as plasmids or as bacteriophage vectors. Examples of other vectors include viruses such as bacteriophages, baculoviruses and retroviruses, DNA viruses, liposomes and other recombination vectors. The vectors can also contain elements for use in either prokaryotic or eukaryotic host systems. One of ordinary skill in the art will know which host systems are compatible with a particular vector. The vectors can be introduced into cells or tissues by any one of a variety of known methods within the art. Such methods can be found generally described in Sambrook et al., Molecular Cloning: A Laboratory Manual, Cold Springs Harbor Laboratory, New York (1989, 1992), in Ausubel et al., Current Protocols in Molecular Biology, John Wiley and Sons, Baltimore, Md. (1989), Chang et al., Somatic Gene Therapy, CRC Press, Ann Arbor, Mich. (1995), Vega et al., Gene Targeting, CRC Press, Ann Arbor, Mich. (1995), Vectors: A Survey of Molecular Cloning Vectors and Their Uses, Butterworths, Boston Mass. (1988) and Gilboa et al., BioTechniques 4:504-512 (1986) and include, for example, stable or transient transfection, lipofection, electroporation and infection with recombinant viral vectors. Viral vectors that have been used for gene therapy protocols include, but are not limited to, retroviruses, other RNA viruses such as poliovirus or Sindbis virus, adenovirus, adeno-associated virus, herpes viruses, SV 40, vaccinia and other DNA viruses. Replication-defective murine retroviral vectors are the most widely utilized gene transfer vectors. Murine leukemia retroviruses are composed of a single strand RNA completed with a nuclear core protein and polymerase (pol) enzymes encased by a protein core (gag) and surrounded by a glycoprotein envelope (env) that determines host range. The genomic structure of retroviruses include gag, pol, and env genes enclosed at the 5' and 3' long terminal repeats (LTRs). Retroviral vector systems exploit the fact that a minimal vector containing the 5' and 3' LTRs and the packaging signal are sufficient to allow vector packaging and infection and integration into target cells providing that the viral structural proteins are supplied in trans in the packaging cell line.

Recombinant methods known in the art can also be used to achieve oligonucleotide reagent-induced inhibition of splicing in a target nucleic acid. For example, vectors containing oligonucleotide reagents can be employed to express, e.g., an antisense oligonucleotide to inhibit splicing of an exon of a targeted pre-mRNA.

Examples of methods to introduced oligonucleotide sequences into cells encompass both non-viral and viral methods, as well as in vivo and ex vivo methods and include, for example:

Direct Injection: Naked DNA can be introduced into cells in vivo by directly injecting the DNA into the cells (see e.g., Acsadi et al. (1991) Nature 332:815-818; Wolff et al. (1990) Science 247:1465-1468). For example, a delivery apparatus (e.g., a "gene gun") for injecting DNA into cells in vivo can be used. Such an apparatus is commercially available (e.g., from BioRad).

Cationic Lipids: Naked DNA can be introduced into cells in vivo by complexing the DNA with cationic lipids or encapsulating the DNA in cationic liposomes. Examples of suitable cationic lipid formulations include N-[-1-(2,3-dioleoyloxy) propyl]N,N,N-triethylammonium chloride (DOTMA) and a 1:1 molar ratio of 1,2-dimyristyloxy-propyl-3-dimethylhydroxyethylammonium bromide (DMRIE) and dioleoyl phosphatidyletanolamine (DOPE) (see e.g., Logan, J. J. et al. (1995) Gene Therapy 2:38-49; San, H. et al. (1993) Human Gene Therapy 4:781-788).

Receptor-Mediated DNA Uptake: Naked DNA can also be introduced into cells in vivo by complexing the DNA to a cation, such as polylysine, which is coupled to a ligand for a cell-surface receptor (see for example Wu, G. and Wu, C. H. (1988) J. Biol. Chem. 263:14621; Wilson et al. (1992) J. Biol. Chem. 267:963-967; and U.S. Pat. No. 5,166,320). Binding of the DNA-ligand complex to the receptor facilitates uptake of the DNA by receptor-mediated endocytosis. A DNA-ligand complex linked to adenovirus capsids which naturally disrupt endosomes, thereby releasing material into the cytoplasm can be used to avoid degradation of the complex by intracellular lysosomes (see for example Curiel et al. (1991) Proc. Natl. Acad. Sci. USA 88:8850; Cristiano et al. (1993) Proc. Natl. Acad. Sci. USA 90:2122-2126). Carrier mediated gene transfer may also involve the use of lipid-based compounds which are not liposomes. For example, lipofectins and cytofectins are lipid-based positive ions that bind to negatively charged DNA and form a complex that can ferry the DNA across a cell membrane. Another method of carrier mediated gene transfer involves receptor-based endocytosis. In this method, a ligand (specific to a cell surface receptor) is made to form a complex with a gene of interest and then injected into the bloodstream. Target cells that have the cell surface receptor will specifically bind the ligand and transport the ligand-DNA complex into the cell.

Retroviruses: Defective retroviruses are well characterized for use in gene transfer for gene therapy purposes (for a review see Miller, A. D. (1990) Blood 76:271). A recombinant retrovirus can be constructed having a nucleotide sequences of interest incorporated into the retroviral genome. Additionally, portions of the retroviral genome can be removed to render the retrovirus replication defective. The replication defective retrovirus is then packaged into virions which can be used to infect a target cell through the use of a helper virus by standard techniques. Protocols for producing recombinant retroviruses and for infecting cells in vitro or in vivo with such viruses can be found in Current Protocols in Molecular Biology, Ausubel, F. M. et al. (eds.) Greene Publishing Associates, (1989), Sections 9.10-9.14 and other standard laboratory manuals. Examples of suitable retroviruses include pLJ, pZIP, pWE and pEM which are well known to those skilled in the art. Examples of suitable packaging virus lines include ΨCrip, ΨCre, Ψ2 and ΨAm. Retroviruses have been used to introduce a variety of genes into many different cell types, including epithelial cells, endothelial cells, lymphocytes, myoblasts, hepatocytes, bone marrow cells, in vitro and/or in vivo (see for example Eglitis, et al. (1985) Science 230:1395-1398; Danos and Mulligan (1988) Proc. Natl. Acad. Sci. USA 85:6460-6464; Wilson et al. (1988) Proc. Natl. Acad. Sci. USA 85:3014-3018; Armentano et al. (1990) Proc. Natl. Acad. Sci. USA 87:6141-6145; Huber et al. (1991) Proc. Natl. Acad. Sci. USA 88:8039-8043; Ferry et al. (1991) Proc. Natl. Acad. Sci. USA 88:8377-8381; Chowdhury et al. (1991) Science 254:1802-1805; van Beusechem et al. (1992) Proc. Natl. Acad. Sci. USA 89:7640-7644; Kay et al. (1992) Human Gene Therapy 3:641-647; Dai et al. (1992) Proc. Natl. Acad. Sci. USA 89:10892-10895; Hwu et al. (1993) J. Immunol. 150:4104-4115; U.S. Pat. No. 4,868,116; U.S. Pat. No. 4,980,286; PCT Application WO 89/07136; PCT Application WO 89/02468; PCT Application WO 89/05345; and PCT Application WO 92/07573). Retroviral vectors require target cell division in order for the retroviral genome (and foreign nucleic acid inserted into it) to be integrated into the host genome to stably introduce nucleic acid into the cell. Thus, it may be necessary to stimulate replication of the target cell.

Adenoviruses: The genome of an adenovirus can be manipulated such that it encodes and expresses a gene product of interest but is inactivated in terms of its ability to replicate in a normal lytic viral life cycle. See for example Berkner et al. (1988) BioTechniques 6:616; Rosenfeld et al. (1991) Science 252:431-434; and Rosenfeld et al. (1992) Cell 68:143-155. Suitable adenoviral vectors derived from the adenovirus strain Ad type 5 d1324 or other strains of adenovirus (e.g., Ad2, Ad3, Ad7 etc.) are well known to those skilled in the art. Recombinant adenoviruses are advantageous in that they do not require dividing cells to be effective gene delivery vehicles and can be used to infect a wide variety of cell types, including airway epithelium (Rosenfeld et al. (1992) cited supra), endothelial cells (Lemarchand et al. (1992) Proc. Natl. Acad. Sci. USA 89:6482-6486), hepatocytes (Herz and Gerard (1993) Proc. Natl. Acad. Sci. USA 90:2812-2816) and muscle cells (Quantin et al. (1992) Proc. Natl. Acad. Sci. USA 89:2581-2584). Additionally, introduced adenoviral DNA (and foreign DNA contained therein) is not integrated into the genome of a host cell but remains episomal, thereby avoiding potential problems that can occur as a result of insertional mutagenesis in situations where introduced DNA becomes integrated into the host genome (e.g., retroviral DNA). Moreover, the carrying capacity of the adenoviral genome for foreign DNA is large (up to 8 kilobases) relative to other gene delivery vectors (Berkner et al. cited supra; Haj-Ahmand and Graham (1986) J. Virol. 57:267). Most replication-defective adenoviral vectors currently in use are deleted for all or parts of the viral E1 and E3 genes but retain as much as 80% of the adenoviral genetic material.

Adeno-Associated Viruses: Adeno-associated virus (AAV) is a naturally occurring defective virus that requires another virus, such as an adenovirus or a herpes virus, as a helper virus for efficient replication and a productive life cycle. (For a review see Muzyczka et al. Curr. Topics in Micro. and Immunol. (1992) 158:97-129). It is also one of the few viruses that may integrate its DNA into non-dividing cells, and exhibits a high frequency of stable integration (see for example Flotte et al. (1992) Am. J. Respir. Cell. Mol. Biol. 7:349-356; Samulski et al. (1989) J. Virol. 63:3822-3828; and McLaughlin et al. (1989) J. Virol. 62:1963-1973). Vectors containing as little as 300 base pairs of AAV can be packaged and can integrate. Space for exogenous DNA is limited to about 4.5 kb. An AAV vector such as that described in Tratschin et al. (1985) Mol. Cell. Biol. 5:3251-3260 can be used to introduce DNA into cells. A variety of nucleic acids have been introduced into different cell types using AAV vectors (see for example Hermonat et al. (1984) Proc. Natl. Acad. Sci. USA 81:6466-6470; Tratschin et al. (1985) Mol. Cell. Biol. 4:2072-2081; Wondisford et al. (1988) Mol. Endocrinol. 2:32-39; Tratschin et al. (1984) J. Virol. 51:611-619; and Flotte et al. (1993) J. Biol. Chem. 268:3781-3790).

The efficacy of a particular expression vector system and method of introducing nucleic acid into a cell can be assessed by standard approaches routinely used in the art. For example, DNA introduced into a cell can be detected by a filter hybridization technique (e.g., Southern blotting) and RNA produced by transcription of introduced DNA can be detected, for example, by Northern blotting, RNase protection or reverse transcriptase-polymerase chain reaction (RT-PCR). The gene product can be detected by an appropriate assay, for example by immunological detection of a produced protein, such as with a specific antibody, or by a functional assay to detect a functional activity of the gene product.

In a preferred embodiment, a retroviral expression vector encoding an oligonucleotide of the invention is used in vivo, to thereby inhibit the activity of the short target intron 7 splice inhibiting domain of SMN2, and thus promote SMN2 exon 7 inclusion in vivo. Such retroviral vectors can be prepared according to standard methods known in the art.

A modulatory agent, such as a chemical compound, can be administered to a subject as a pharmaceutical composition. Such compositions typically comprise the modulatory agent and a pharmaceutically acceptable carrier. As used herein the term "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions is contemplated. Supplementary active compounds can also be incorporated into the compositions. Pharmaceutical compositions can be prepared as described herein.

Cells targeted or used in the methods of the instant invention are preferably mammalian cells, in particular, human cells. Cells may be from the germ line or somatic, totipotent or pluripotent, dividing or non-dividing, parenchyma or epithelium, immortalized or transformed, or the like. The cell may be a stem cell or a differentiated cell. Cell types that are differentiated include adipocytes, fibroblasts, myocytes, cardiomyocytes, endothelium, neurons, glia, blood cells, megakaryocytes, lymphocytes, macrophages, neutrophils, eosinophils, basophils, mast cells, leukocytes, granulocytes, keratinocytes, chondrocytes, osteoblasts, osteoclasts, hepatocytes, and cells of the endocrine or exocrine glands. Neurons and muscle cells (e.g., myocytes, myoblasts, myotubes, myofibers, and the like) are preferred target cells of the invention.

Depending on the particular target gene and the dose of oligonucleotide reagent material delivered, this process may modulate function of the target gene. In exemplary embodiments of the instant invention, exon 7-containing SMN protein production is enhanced in a treated cell, cell extract, organism or patient, with an enhancement of exon 7-containing SMN protein levels of at least about 1.1-, 1.2-, 1.5-, 2-, 3-, 4-, 5-, 7-, 10-, 20-, 100-fold and higher values being exemplary. Enhancement of gene expression refers to the presence (or observable increase) in the level of protein and/or mRNA product from a target RNA. Specificity refers to the ability to act on the target RNA without manifest effects on other genes of the cell. The consequences of modulation of the target RNA can be confirmed by examination of the outward properties of the cell or organism (as presented below in the examples) or by biochemical techniques such as RNA solution hybridization, nuclease protection, Northern hybridization, reverse transcription, gene expression monitoring with a microarray, antibody binding, enzyme linked immunosorbent assay (ELISA), Western blotting, radioimmunoassay (RIA), other immunoassays, and fluorescence activated cell analysis (FACS).

For oligonucleotide reagent-mediated modulation of an RNA in a cell line or whole organism, gene expression is conveniently assayed by use of a reporter or drug resistance gene whose protein product is easily assayed. Such reporter genes include acetohydroxyacid synthase (AHAS), alkaline phosphatase (AP), beta galactosidase (LacZ), beta glucoronidase (GUS), chloramphenicol acetyltransferase (CAT), green fluorescent protein (GFP), horseradish peroxidase (HRP), luciferase (Luc), nopaline synthase (NOS), octopine synthase (OCS), and derivatives thereof. Multiple selectable markers are available that confer resistance to ampicillin, bleomycin, chloramphenicol, gentamycin, hygromycin, kanamycin, lincomycin, methotrexate, phosphinothricin, puromycin, and tetracyclin. Depending on the assay, quantitation of the amount of gene expression allows one to determine a degree of modulation which is greater than 10%, 33%, 50%, 90%, 95% or 99% as compared to a cell not treated according to the present invention. Lower doses of injected material and longer times after administration of oligonucleotide reagents may result in modulation in a smaller fraction of cells (e.g., at least 10%, 20%, 50%, 75%, 90%, or 95% of targeted cells). Quantitation of gene expression in a cell may show similar amounts of modulation at the level of accumulation of target mRNA or translation of target protein. As an example, the efficiency of modulation may be determined by assessing the amount of gene product in the cell; pre-mRNA or mRNA may be detected with a hybridization probe having a nucleotide sequence outside the region used for the oligonucleotide reagent, or translated polypeptide may be detected with an antibody raised against the polypeptide sequence of that region.

The oligonucleotide reagent may be introduced in an amount which allows delivery of at least one copy per cell. Higher doses (e.g., at least 5, 10, 100, 500 or 1000 copies per cell) of material may yield more effective modulation; lower doses may also be useful for specific applications.

III. Methods of Treatment

The present invention provides for both prophylactic and therapeutic methods of treating a subject at risk of (or susceptible to) a disorder or having a disorder associated with aberrant or unwanted target gene expression or activity (e.g., in exemplary embodiments, underexpression of SMN protein). "Treatment", or "treating" as used herein, is defined as the application or administration of a therapeutic agent (e.g., an oligonucleotide reagent (e.g., oligoribonucleotide) or vector or transgene encoding same, a small molecule short intron 7 splice inhibiting blocking agent, etc.) to a patient, or application or administration of a therapeutic agent to an isolated tissue or cells (including fetal cells) from a patient, who has a disease or disorder, a symptom of disease or disorder or a predisposition toward a disease or disorder, with the purpose to cure, heal, alleviate, relieve, alter, remedy, ameliorate, improve or affect the disease or disorder, the symptoms of the disease or disorder, or the predisposition toward disease.

With regards to both prophylactic and therapeutic methods of treatment, such treatments may be specifically tailored or modified, based on knowledge obtained from the field of pharmacogenomics. "Pharmacogenomics", as used herein, refers to the application of genomics technologies such as gene sequencing, statistical genetics, and gene expression analysis to drugs in clinical development and on the market. More specifically, the term refers the study of how a patient's genes determine his or her response to a drug (e.g., a patient's "drug response phenotype", or "drug response genotype"). Thus, another aspect of the invention provides methods for tailoring an individual's prophylactic or therapeutic treatment with either the target gene molecules of the present invention or target gene modulators according to that individual's drug response genotype. Pharmacogenomics allows a clinician or physician to target prophylactic or therapeutic treatments to patients who will most benefit from the treatment and to avoid treatment of patients who will experience toxic drug-related side effects.

1. Prophylactic Methods

In one aspect, the invention provides a method for preventing in a subject, a disease or condition associated with an aberrant or unwanted target gene expression or activity, by administering to the subject a therapeutic agent (e.g., an oligonucleotide reagent (e.g., oligoribonucleotide) or vector or transgene encoding same, a small molecule short intron 7 splice inhibiting blocking agent, etc.). Subjects at risk for a disease which is caused or contributed to by aberrant or unwanted target gene expression or activity can be identified by, for example, any or a combination of diagnostic or prognostic assays as described herein. Administration of a prophylactic agent can occur prior to the manifestation of symptoms characteristic of the target gene aberrancy, such that a disease or disorder is prevented or, alternatively, delayed in its progression. Depending on the type of target gene aberrancy, for example, a target gene, target gene agonist or target gene antagonist agent can be used for treating the subject. The appropriate agent can be determined based on screening assays described herein.

2. Therapeutic Methods

Another aspect of the invention pertains to methods of modulating target gene expression, protein expression or activity for therapeutic purposes. Accordingly, in an exemplary embodiment, the modulatory method of the invention involves contacting a cell capable of expressing target gene with a therapeutic agent (e.g., an oligonucleotide reagent (e.g., oligoribonucleotide) or vector or transgene encoding same, a small molecule short intron7 target blocking agent, etc.) that is specific for the target gene or protein (e.g., is specific for the pre-mRNA encoded by said gene and/or specifying the amino acid sequence of said protein) such that expression or one or more of the activities of target protein is modulated. These modulatory methods can be performed in vitro (e.g., by culturing the cell with the agent) or, alternatively, in vivo (e.g., by administering the agent to a subject). As such, the present invention provides methods of treating an individual afflicted with a disease or disorder characterized by aberrant or unwanted expression or activity of a target gene polypeptide or nucleic acid molecule. Modulation of target gene activity is desirable in situations in which target gene is abnormally unregulated and/or in which altered target gene activity is likely to have a beneficial effect.

In one embodiment, cells from a subject having spinal muscular atrophy are contacted with an oligonucleotide reagent of the invention to inhibit splicing of the SMN2 exon 7. Exemplary oligonucleotide reagents include sequences complementary to the short intron 7 target sequence and variants thereof (e.g., as shown herein). In another embodiment, cells from a subject having another disorder that would benefit from inhibition of alternative splicing are contacted with an oligonucleotide reagent of the invention. Target sequences related to the target sequences disclosed herein are present in human intronic sequences. For example, there is a sequence partially homologous to the ISS-N1 sequence located in human CFTR (intron 10). Additional exemplary genes that can be targeted by oligonucleotide reagents of the invention (e.g., sequences complementary to the target sequences and variants thereof (e.g., as shown herein) include, but are not limited to, CFTR, FAS, Caspases, Diablo, NF1, Bcl2, Tau, ApoA-11, p53, Tra2, Cox-1 and Survivin.

3. Delivery of Oligonucleotide Reagents to the Nervous System

The oligonucleotide reagents of the invention can be delivered to the nervous system of a subject by any art-recognized method. For example, peripheral blood injection of the oligonucleotide reagents of the invention can be used to deliver said reagents to peripheral neurons via diffusive and/or active means. Alternatively, the oligonucleotide reagents of the invention can be modified to promote crossing of the blood-brain-barrier (BBB) to achieve delivery of said reagents to neuronal cells of the central nervous system (CNS). Specific recent advancements in oligonucleotide reagent technology and delivery strategies have broadened the scope of oligonucleotide reagent usage for neuronal disorders (Forte, A., et al. 2005. Curr. Drug Targets 6:21-29; Jaeger, L. B., and W. A. Banks 2005. Methods Mol. Med. 106:237-251; Vinogradov, S. V., et al. 2004. Bioconjug. Chem. 5:50-60; the preceding are incorporated herein in their entirety by reference). For example, the oligonucleotide reagents of the invention can be synthesized to comprise phosphorothioate oligodeoxynucleotides (P-ODN) directed against the short intron 7 target sequence, or may be generated as peptide nucleic acid (PNA) compounds. P-ODN and PNA reagents have each been identified to cross the BBB (Jaeger, L. B., and W. A. Banks 2005. Methods Mol. Med. 106:237-251). Treatment of a subject with, e.g., a vasoactive agent, has also been described to promote transport across the BBB (ibid.). Tethering of the oligonucleotide reagents of the invention to agents that are actively transported across the BBB may also be used as a delivery mechanism.

In certain embodiments, the oligonucleotide reagents of the invention can be delivered by transdermal methods (e.g., via incorporation of the oligonucleotide reagent(s) of the invention into, e.g., emulsions, with such oligonucleotide reagents optionally packaged into liposomes). Such transdermal and emulsion/liposome-mediated methods of delivery are described for delivery of antisense oligonucleotides in the art, e.g., in U.S. Pat. No. 6,965,025, the contents of which are incorporated in their entirety by reference herein.

The oligonucleotide reagents of the invention may also be delivered via an implantable device (e.g., pacemaker or other such implantable device). Design of such a device is an art-recognized process, with, e.g., synthetic implant design described in, e.g., U.S. Pat. No. 6,969,400, the contents of which are incorporated in their entirety by reference herein.

4. Pharmacogenomics

The therapeutic agents (e.g., an oligonucleotide reagent or vector or transgene encoding same) of the invention can be administered to individuals to treat (prophylactically or therapeutically) disorders associated with aberrant or unwanted target gene activity. In conjunction with such treatment, pharmacogenomics (i.e., the study of the relationship between an individual's genotype and that individual's response to a foreign compound or drug) may be considered. Differences in metabolism of therapeutics can lead to severe toxicity or therapeutic failure by altering the relation between dose and blood concentration of the pharmacologically active drug. Thus, a physician or clinician may consider applying knowledge obtained in relevant pharmacogenomics studies in determining whether to administer a therapeutic agent as well as tailoring the dosage and/or therapeutic regimen of treatment with a therapeutic agent.

5. Pharmaceutical Compositions

The invention pertains to uses of the above-described agents for therapeutic treatments as described infra. Accordingly, the modulators of the present invention (e.g., oligonucleotides, small molecules and the like) can be incorporated into pharmaceutical compositions suitable for administration. Such compositions typically comprise the nucleic acid molecule, protein, antibody, or modulatory compound and a pharmaceutically acceptable carrier. As used herein the language "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

A pharmaceutical composition of the invention is formulated to be compatible with its intended route of administration. Examples of routes of administration include parenteral, e.g., intravenous, intradermal, subcutaneous, intraperitoneal, intramuscular, oral (e.g., inhalation), transdermal (topical), and transmucosal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals. Toxicity and therapeutic efficacy of such compounds can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds that exhibit large therapeutic indices are preferred. Although compounds that exhibit toxic side effects may be used, care should be taken to design a delivery system that targets such compounds to the site of affected tissue in order to minimize potential damage to uninfected cells and, thereby, reduce side effects. The data obtained from the cell culture assays and animal studies can be used in formulating a range of dosage for use in humans. The dosage of such compounds lies preferably within a range of circulating concentrations that include the ED50 with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the EC50 (i.e., the concentration of the test compound which achieves a half-maximal response) as determined in cell culture. Such information can be used to more accurately determine useful doses in humans. Levels in plasma may be measured, for example, by high performance liquid chromatography.

The pharmaceutical compositions can be included in a container, pack, or dispenser together with instructions for administration.

This invention is further illustrated by the following examples which should not be construed as limiting. The contents of all references, patents and published patent applications cited throughout this application are incorporated herein by reference.

EXAMPLES

Example 1

Modulation of aberrant splicing using antisense oliogonucleotides (ASOs) is an emerging technology with tremendous therapeutic potential. An ASO-based approach could be also employed to determine unique interactions that are difficult to uncover using traditional means of deletion and substitution mutations. Here we report a novel finding of an antisense microwalk in which we examined the position-specific role of intronic residues downstream of the 5' splice site (5' ss) of SMN2 exon 7, skipping of which is associated with Spinal Muscular Atrophy (SMA), a leading genetic cause of infant mortality. Our results revealed the inhibitory role of a cytosine residue at the $10^{th}$ intronic position ($^{10}$C), which is neither conserved nor associated with any known splicing motif. Significance of $^{10}$C emerged from the splicing pattern of SMN2 exon 7 in presence of a 14-mer ASO (L14) that sequestered two adjacent hnRNP A1 motifs downstream of $^{10}$C and yet promoted SMN2 exon 7 skipping. Another 14-mer ASO (F14) that sequestered both, $^{10}$C and adjacent hnRNP A1 motifs, led to a strong stimulation of SMN2 exon 7 inclusion. The inhibitory role of $^{10}$C was found to be tightly linked to its unpaired status and specific positioning immediately upstream of a RNA:RNA helix formed between the targeting ASO and its intronic target. Employing a heterologous context as well as changed contexts of SMN2 intron 7, we show that the inhibitory effect of unpaired $^{10}$C is dependent upon a long-distance interaction involving downstream intronic sequences. Our report furnishes one of the rare examples in which an ASO-based approach could be applied to unravel the critical role of an intronic position that may not belong to a linear motif and yet play significant role through long-distance interactions.

Alternative splicing is an essential process in the generation of protein diversity and has been a major contributory force to genome evolution (Xing and Lee 2007). Current estimates suggest that 95-100% of human genes with two or more exons are alternatively spliced affecting all major aspects of cellular metabolism (Nilsen and Graveley 2010). Splicing is catalyzed by a spliceosome that represents one of the most complex macromolecular machines known (Nilsen 2003; Matlin and Moore 2007). Control of alternative splicing rests on non-spliceosomal factors that bind to pre-mRNA sequences called exonic or intronic splicing enhancers (ESEs or ISEs) and silencers (ESSs or ISSs) (Lin and Fu 2007; Martinez-Contreras et al. 2007; David and Manley 2008). Enhancer and silencer motifs promote or suppress splice-site (ss) selection, respectively. Methods to identify splicing motifs are continuing to evolve (Chasin 2007; Singh 2007a; Hertel 2008; Wang and Burge 2008; Yu et al. 2008). An additional regulatory role is provided by RNA structures that enforce accessibility to splicing elements, as well as bring two distantly located cis-elements in close proximity (Graveley 2005; Buratti et al. 2007; Singh et al. 2007, Shepard and Hertel 2008; Warf et al. 2009). Unraveling the mechanism by which splicing factors, RNA regulatory sequences and structural motifs coordinate to regulate alternative splicing is an area of growing interest for evolving strategies to cure many human diseases associated with defective splicing (Garcia-Blanco 2006; Tazi et al. 2009; Cooper et al. 2009; Ward and Cooper 2010).

Despite a tremendous progress in our understanding of pre-mRNA splicing, validation of splicing motifs in the context of an endogenous gene has remained a daunting task. Antisense oligonucleotide (ASO)-based approaches offer an extraordinary potential to address this issue with additional implication to therapy of human diseases (Hua et al. 2008; Bauman et al. 2009). Refinements of ASO-based strategies have capability to provide information regarding the accessibility and the role of certain regions within RNA sequence. For example, ASO scanning arrays have been employed to probe alternative folding of RNA sequences (Ooms et al. 2004). The most exciting future application of an ASO-based approach includes identification of the critical role of an individual residue in pre-mRNA splicing using endogenous context. Such studies would address the role of the nonlinear motifs with implications to high-order interactions and structural rearrangements.

Humans have two nearly identical copies of the Survival Motor Neuron (SMN) gene: SMN1 and SMN2 (Lefebvre et al. 1995). The two SMN genes code for identical proteins; however, SMN2 predominantly generates a short transcript due to skipping of exon 7, producing a truncated SMN that is highly unstable (Vitte et al. 2007). The inability of SMN2 to compensate for the loss of SMN1 results in spinal muscular atrophy (SMA), a debilitating disease of children and infants (Wirth et al. 2006). Since SMN2 is almost universally present in SMA patients, correction of SMN2 exon 7 splicing holds the promise for cure. Due to anticipated target specificity, a large number of studies have focused on ASO-based approaches to restore SMN2 exon 7 inclusion (Bauman et al. 2009). Among these studies, our earlier reported intronic splicing silencer N1 (ISS-N1) has emerged as a leading target in a systematic antisense microwalk (Singh et al. 2006; Hua et al. 2008). Consistently, a recent report has independently confirmed the high therapeutic potential of ISS-N1 by demonstrating that blocking ISS-N1 with an ASO substantially elevated the SMN levels in brain of SMA mice (Williams et al. 2009).

ISS-N1 is a mixed composition sequence spanning from the $10^{th}$ to $24^{th}$ position of intron 7 (Singh et al. 2006; FIG. 1A). Due to its strategic location and strong negative impact, ISS-N1 has been termed as the master checkpoint (Buratti et al. 2006). The 15-nucleotide-long ISS-N1 harbors two putative hnRNP A1 motifs that have been proposed to be responsible for its inhibitory impact (Hua et al. 2008; FIG. 1A). Using an ultra-refined antisense micro-walk, we have recently shown that ISS-N1 overlaps with an 8-nucleotide-long GC-rich sequence spanning from the $7^{th}$ to $14^{th}$ position of intron 7 (Singh et al. 2009; FIG. 1A). We have also shown that sequestering of this GC-rich sequence with an 8-mer ASO fully restores SMN2 exon 7 inclusion in SMA patient cells (Singh et al. 2009). Interestingly, the stimulatory effect of the 8-mer ASO comes without full sequestration of any of the validated hnRNP A1 binding sites. Thus, our results open a possibility of the role of an additional negative element and/or structural motif associated with the GC-rich sequence in the vicinity of the 5' splice site (5' ss). We have earlier reported the inhibitory role of a RNA structure (terminal stem-loop 2 or TSL2) sequestering the 5' ss of SMN2 exon 7 (Singh et al. 2007). It remains to be seen if a factor interacting with TSL2 makes a secondary contact with the downstream GC-rich sequence or vice-versa.

Given the large number of ASOs tested (against ISS-N1), ISS-N1 stands out among other splicing-correcting antisense targets reported thus far. Nevertheless, not all size combinations of ASOs targeting ISS-N1 and its neighboring sequences have been examined. Consequently, the published results do not address the role of specific residues that fall beyond the traditional definition of motifs associated with the known splicing factors. Here we take advantage of an additional antisense microwalk to reveal the critical role of a cytosine residue at the $10^{th}$ position of human SMN2 intron 7 in conferring the nature of the antisense response. We refer this residue as $^{10}$C here after. $^{10}$C represents the first residue of ISS-N1 but does not belong to any of the known motifs, including hnRNP A1. Our study revealed a rare finding in which two identical size ASOs whose target differed by a single nucleotide (one ASO sequestered $^{10}$C, whereas other did not) produced an opposite effect on SMN2 exon 7 splicing. We confirmed that unsequestered $^{10}$C plays a strong negative role when combined with an ASO targeting a 14-nucleotide sequence immediately downstream of [10]C. We also show that the inhibitory effect of unsequestered [10]C. is dependent upon a long-distance interaction involving downstream intronic sequences. Our findings underscore the potential of an ASO-based approach in unraveling the paramount significance of a single intronic nucleotide due to its location relative to other splicing cis-elements within an entire intron.

Identification of a Master Position within the Core of the Antisense Target

Substantial evidence and independent validations confirm that ISS-N1 is an ideal target for an ASO-mediated correction of aberrant splicing associated with a major genetic disease (Singh et al. 2006, 2009; Hua et al. 2008; Williams et al. 2009). Based on a stimulatory effect of ASOs targeting ISS-N1 and the GC-rich sequence, we have established that the first five residues of ISS-N1 constitute the core of antisense target (Singh et al. 2009). [10]C occupies the first position of this core and is strategically located in the middle of the GC-rich sequence (FIG. 1). The significance of [10]C emerges from the fact that it may participate in high-order interaction because it does not fall within the confines of the recently described hnRNP A1 motifs proposed to be a cause for the negative effect associated with ISS-N1 (Hua et al. 2008; Singh et al. 2009).

To further examine the role of [10]C as an integral part of the antisense target we performed an additional ultra-refined antisense micro-walk. We used ASOs of varying sizes that blocked different portions of ISS-N1 with or without sequestering [10]C. Of note, since ISS-N1 is a 15-nucleotide-long element, we confined our comparison of antisense effect to 15-mer or shorter ASOs (Anti-N1 being the only exception). Annealing positions of ASOs are diagrammatically shown in FIG. 1B. Sequences of all ASOs used in this study are given in Table 1. For the sake of simplicity, we used an antisense nomenclature comprised of a letter(s) followed by a number that represents the size of an ASO. F series ASOs possess the identical 3' ends with the first position of ISS-N1 being complementary to the 3'-terminal nucleotides of ASOs. L series ASOs possess the identical 5' ends with the last position of ISS-N1 being complementary to the 5'-terminal nucleotides of ASOs. M series ASOs block sequences in the middle of ISS-N1. Other ASOs containing UP and DN letters sequester residues upstream and downstream of ISS-N1, respectively. Here, we performed antisense screening at a relatively low ASO concentration of 20 nM. Our earlier reported ASOs that sequestered [10]C served as positive controls (FIG. 1B, green bars). SEQ ID NO: 4-25 respectively.

TABLE 1

Anti-N1:
    SEQ ID NO: 4
    5'AUUCACUUUCAUAAUGCUGG3'

F15:
    SEQ ID NO: 5
    5'CUUUCAUAAUGCUGG3'

1UP15:
    SEQ ID NO: 6
    5'UUUCAUAAUGCUGGC3'

2UP15:
    SEQ ID NO: 7
    5'UUCAUAAUGCUGGCA3'

3UP15:
    SEQ ID NO: 8
    5'UCAUAAUGCUGGCAG3'

TABLE 1-continued

1DN15:
    SEQ ID NO: 9
    5'ACUUUCAUAAUGCUG3'

2DN15:
    SEQ ID NO: 10
    5'CACUUUCAUAAUGCG3'

3DN15:
    SEQ ID NO: 11
    5'UCACUUUCAUAAUGC3'

F14:
    SEQ ID NO: 12
    5'UUUCAUAAUGCUGG3'

L14:
    SEQ ID NO: 13
    5'CUUUCAUAAUGCUG3'

F13:
    SEQ ID NO: 14
    5'UUCAUAAUGCUGG3'

L13:
    SEQ ID NO: 15
    5'CUUUCAUAAUGCU3'

M13:
    SEQ ID NO: 16
    5'UUUCAUAAUGCUG3'

F12:
    SEQ ID NO: 17
    5'UCAUAAUGCUGG3'

M12F:
    SEQ ID NO: 18
    5'UUCAUAAUGCUG3'

M12L:
    SEQ ID NO: 19
    5'UUUCAUAAUGCU3'

F11:
    SEQ ID NO: 20
    5'CAUAAUGCUGG3'

F10:
    SEQ ID NO: 21
    5'AUAAUGCUGG3'

F9:
    SEQ ID NO:
    5'UAAUGCUGG3'

F14comp:
    SEQ ID NO: 22
    5'UUUCAUACUUCUGG3'

L14comp:
    SEQ ID NO: 23
    5'CUUUCAUACUUCUG3'

F14LNA:
    SEQ ID NO: 24
    5'TTTCAUAATGCTGG3'

FL14LNA:
    SEQ ID NO: 25
    5'CTTTCATAATGCTG3'

As shown in FIG. 1C, ASOs that did not sequester [10]C failed to produce any stimulatory response on SMN2 exon 7 inclusion and in some instances even caused an increase in SMN2 exon 7 skipping. The most striking example was L14, particularly when the effect of this ASO was compared to the effect of F14. Note that both ASOs are 14-nucleotide-long, the GC content of their targets is the same, and their annealing positions differ by only one nucleotide, $^{10}$C. Yet F14 and L14 produce opposite effects on exon 7 splicing: F14 that sequestered $^{10}$C efficiently restored SMN2 exon 7 inclusion, while L14 that did not block $^{10}$C increased exon 7 skipping (FIG. 1C). Antagonistic effects of F14 and L14 were verified by three different batches of ASOs synthesized at different times. Also, we performed experiments at various concentrations ranging from 1 nM to 1 µM. Stimulatory effect of F14 increased with the increasing concentrations of F14, whereas the inhibitory effect of L14 increased with the increasing concentrations of L14 (not shown). Of note, L14 sequestered both hnRNP A1 motifs within ISS-N1 and yet promoted SMN2 exon 7 skipping. Other short ASOs that did not sequester $^{10}$C had less pronounced negative effects. For example, L13 and M13 that are only one-nucleotide shorter than L14, showed substantially reduced if any negative effects on SMN2 exon 7 splicing. Similar results were observed with M12F and M12L that annealed to the twelve-nucleotide-long sequences in the middle of ISS-N1. We also tested 15-mer ASOs that did not sequester $^{10}$C but targeted sequences immediately downstream of $^{10}$C. These 15-mer ASOs produced inhibitory response albeit at higher concentrations (not shown).

Next, we wished to verify that the antagonistic effects of F14 and L14 on splicing of SMN2 exon 7 were not specific to the chemistry of ASOs. Note that in our ultra-refined microwalk described above, the ASOs had uniform phosphorothioate backbone and 2'-O-methyl modifications (FIG. 1D). For comparison, we chose F14 and L14 with locked nucleic acid (LNA) chemistry in which an extra-bridge that connects 2'-oxygen and 4'-carbon of ribose sugar is added (FIG. 1D). LNAs display unprecedented hybridization affinity toward complementary single-stranded RNA and have been widely used in a variety of applications (Veedu and Wengel 2009). In LNAs used in our experiments, we also replaced uracyl residues with thymidine residues. Such replacement has a potential to improve base pairing with adenosine residues. To increase the intracellular stability of LNAs, we incorporated uniform phosphorothioate backbone. LNAs corresponding to F14 and L14 were named as F14LNA and L14LNA, respectively. As shown in FIG. 1D, F14LNA and L14LNA retained their characteristic antagonistic effects. These results validated the fact that sequestering of $^{10}$C is essential for producing the stimulatory response irrespective of the chemistry of ASO. In addition, our results showed that inhibitory effect of unsequestered $^{10}$C does not depend on the chemistry of the duplex formed between an ASO and its ISS-N1 target.

Antisense Effect is Specific to Base Paring with Target

Having discovered that two antisense targets differing by a single nucleotide could produce antagonistic effect upon annealing to their cognate ASOs, we next examined the efficacy and specificity of these ASOs using SMN2 minigene system. For this, HeLa cells were co-transfected with the minigene (0.1 µg) and an ASO of interest (50 nM) and the effect on splicing was accessed by RT-PCR. To avoid the off-target effect, we deliberately chose a lower range of minigene and ASO concentrations that we have determined to be optimum for modulation of SMN2 exon 7 splicing (Singh et al. 2009). As shown in FIG. 2A, the antisense effect on splicing of SMN2 minigene was consistent with the results for the endogenous SMN2 in SMA patient fibroblasts: F14 increased exon 7 inclusion, while L14 increased exon 7 skipping. These results validate the necessity of sequestration of $^{10}$C for the stimulatory response of ASOs targeting ISS-N1. Our results also suggest that sequences upstream of exon 6 do not modulate the response of ASOs targeting ISS-N1. When F14 and L14 were mutated giving rise to ASOs we called F14comp and L14comp, their effect on SMN2 exon 7 splicing was obviated (FIG. 2A). These results suggest that the positive effect of F14 and negative effect L14 on splicing of exon 7 are dependent on ASO base pairing with their respective target sites.

To further validate that the opposite effects of F14 and L14 are not due to interactions with non-specific targets, we performed a key experiment in which ASOs were co-transfected with our earlier described mutant minigene, SMN2/17-08. This minigene has C-to-A and U-to-G substitutions at the $5^{th}$ and the $7^{th}$ positions of ISS-N1, respectively. We have shown that these substitutions have capability to weaken the RNA:RNA duplex formed between Anti-N1 and ISS-N1 (Singh et al. 2006). Consistently, both F14 and L14 lost their respective antisense effects when co-transfected with SMN2/17-08 (FIG. 2B), confirming their target specificity. At the same time, F14comp and L14comp, which showed perfect complementarity with the mutated ISS-N1 within SMN2/17-08, produced the respective antisense effect similar to the outcome of F14 and L14 sequestration of the wild type ISS-N1 (FIG. 2B). These results also underscore that the inhibitory effect of untargeted $^{10}$C is not linked to the sequence of duplex formed between an ASO and its target within ISS-N1 region.

Site-Specific Mutations Confirm the Negative Impact of Unpaired $^{10}$C

We next wished to investigate a possible mechanism behind the negative effect of L14 on SMN2 exon 7 splicing. We began addressing this issue by employing a SMN2 mutant minigene (SMN2Δ64) in which $^{10}$C was deleted bringing the target of L14 one nucleotide closer to the 5' ss. As shown in FIG. 3A, the deletion of $^{10}$C somewhat increased exon 7 skipping as compared to the wild type SMN2, indicating that the negative effect of ISS-N1 could be retained without $^{10}$C. Interestingly, when co-transfected with SMN2Δ64, L14 showed a strong stimulatory response on exon 7 inclusion (FIG. 3A). This result validated the inhibitory nature of unsequestered $^{10}$C in the context of the L14:target duplex (L14-duplex) and underscored a rare finding that deletion of a single intronic position upstream of a target sequence could reverse the impact of antisense response. Interestingly, F14 maintained its stimulatory effect in SMN2Δ64 despite a one-nucleotide overhang at the 3' end due to the deletion of $^{10}$C. However, improvement of exon 7 inclusion in the presence of F14 was milder than the one produced by L14, probably due to the fact that the RNA:RNA duplex formed by L14 and its target was longer by one nucleotide.

To further confirm that the inhibitory effect of L14 is due to untargeted $^{10}$C in the context of L14-duplex, we used 5'1U-F15. This ASO is identical to L14 except it has an additional uracyl residue added at its 3'-end. Note that this residue does not base pair with $^{10}$C but is capable of sterically preventing the accessibility of $^{10}$C (FIG. 3B). As shown in FIG. 3B, 5'1U-F15 completely overcame the inhibitory response of L14. However, it was unable to produce a stimulatory response since it did not effectively sequester $^{10}$C.

To test whether the inhibitory effect of L14-duplex is specifically linked to the type of residue at the $10^{th}$ intronic position, we used SMN2/64A minigene in which $^{10}$C residue was replaced with an adenosine residue ($^{10}$A). This mutation did not change the splicing pattern of SMN2 (FIG. 3B) allowing more accurate comparison of the antisense response with and without the sequestration of the $10^{th}$ intronic nucleotide. Surprisingly, L14 produced a strong stimulatory effect in the context of $^{10}$A confirming that the inhibitory effect of L14-duplex in the wild type context is solely linked to an untargeted cytosine residue at the $10^{th}$ intronic position. Consistent with the neutral role of the unpaired $^{10}$A, ASOs such as F15, F14 and 1DN15 also produced stimulatory effect on exon 7 inclusion in SMN2/64A minigene. The effects of these ASOs were similar to 5'1U-F15 that sequestered the $^{10}$A (FIG. 3B).

Effect of the Immediate Context on the Antisense Response

In order to examine the role of the immediate context of target sequence on the antisense response, we used our previously described SMN2 minigene mutants (Singh et al. 2006). In SMN2/5A and SMN2/5G five adenosine and guanosine residues were inserted before ISS-N1, respectively. Such arrangement will place $^{10}$C away from the 5' ss and alter the nature of a presumptive long-distance and/or short-distance interactions that are specific to a nucleotide located at a particular position. When transfected in HeLa cells, SMN2/5A and SMN2/5G showed somewhat less skipping of exon 7 as compared to the wild type SMN2 minigene (FIG. 4B). Upon treatment with F14, both SMN2/5A and SMN2/5G showed increased exon 7 inclusion, suggesting that the effect of F14 is exclusively based on the blocking of a linear cis-element comprised of two putative hnRNP A1 binding sites. Our results also confirmed that the effect of F14 is not sensitive to the precise location of target site with respect to the 5' ss. On the other hand, L14 produced a decreased negative effect, suggesting that a combination of unsequestered $^{15}$C and L14-duplex is less inhibitory than a combination of unsequestered $^{10}$C and L14-duplex. Overall our results support that relative positioning of an antisense target with respect to the 5' ss may be important for determining the impact of an unsequestered residue preceding an RNA:RNA duplex formed between the target and an ASO.

To further understand the impact of the local context on the antisense response, we used N1Δ30-34 and N1Δ25-34 minigenes in which five and ten residues were deleted immediately downstream of ISS-N1, respectively (FIG. 4A). These deletions are likely to break any secondary structure overlapping ISS-N1. When transfected in HeLa cells, transcripts derived from both of the above mutants displayed increased exon 7 skipping (FIG. 4B). In both of these mutants, F14 and L14 produced strong stimulatory and inhibitory effect, respectively. Since these mutants retain the relative positioning of ISS-N1 with respect to the 5' ss, the antisense response was very similar to the one in the wild type context. These results also suggest that the inhibitory effect of the combination of an untargeted $^{10}$C and the downstream L14-duplex might not be affected by the sequences immediately downstream of ISS-N1. However, our results do not rule out the role of further downstream intronic sequences that may interact with the untargeted $^{10}$C during the catalytic core formation.

Effect of the Heterologous Context on the Antisense Response

Studies in a heterologous system provide valuable information regarding portability of a cis-element in question. Linear cis-elements are easily portable in a heterologous context, whereas complex cis-elements involving long-distance interactions are generally not portable. We have previously shown that ISS-N1 is a portable cis-element because its insertion at the identical location within intron 6 of Caspase 3 (Casp3) minigene promotes skipping of Casp3 exon 6 (Singh et al. 2006). Indeed, when transfected in Hela cells, Casp3ISS-N1 minigene showed 43% of Casp3 exon 6 skipping as compared to 19% observed in Casp3Avr minigene that lacks ISS-N1 (FIGS. 5A and B). 3'-Cluster is another negative element located upstream of the 5' ss of SMN2 exon 7 (Singh et al. 2004a). Interestingly, insertion of this element at the similar location relative to the 5' ss (3 nucleotide upstream of the exon/intron junction, FIG. 5A) in Casp3 exon 6 (Casp3-3'Cl minigene) caused moderate increase in skipping of this exon (FIG. 5B). When both 3'-Cluster and ISS-N1 were inserted in Casp3 minigene (Casp3N1C1 mutant, FIG. 5A), skipping of Casp3 exon 6 increased to 90% (FIG. 5B). Note that in Casp3N1C1 mutant we tried to recreate "SMN2" arrangement of ISS-N1 and 3'-Cluster relative to each other and the 5' ss. For this purpose ISS-N1 and 3'-Cluster were inserted 9 and 3 nucleotides down- and up-stream of the 5' ss of Casp3 exon 6, respectively (FIG. 5A). Since Casp3N1C1 showed the highest amount of exon skipping (FIG. 5B), we decided to use this minigene to test the effect of ISS-N1 targeting by F14 and L14 on splicing of the "heterologous" exon. As shown in FIG. 5C, when Casp3N1C1 was co-transfected with F14, inclusion of Casp3 exon 6 increased significantly. Surprisingly, L14 also produced a moderate stimulatory response despite the unsequestered $^{10}$C (FIG. 5C). We observed similar results using Casp3-SMN5'-1 minigene in which twelve residues between 3'-Cluster and ISS-N1 (last three exonic and first nine intronic residues) were replaced with SMN sequence (FIG. 5A). The replaced residues combined with the 3'-Cluster and ISS-N1 introduced the 5' ss "environment" of SMN2 exon 7 in Casp3 minigene. Yet, in Casp3 context the combination of the unsequestered $^{10}$C and L14-duplex was unable to produce an inhibitory effect observed in SMN2. These results suggested a possible role of additional sequences in conferring the negative effect associated with unsequestered $^{10}$C.

Absence of negative effect of L14 in heterologous context could be due to the lack of cooperative interactions among cis-elements that define both, the 3' and 5' ss of SMN2 exon 7. To address this issue, we created a hybrid minigene (Casp3SMN2) in which we replaced the entire middle exon and flanking intronic sequences of Casp3 splicing cassette with 269 nucleotides of SMN2 containing entire exon 7, 116 nucleotides of upstream intron 6 and 99 nucleotides of downstream intron 7 (FIG. 5D). Thus, Casp3SMN2 provided an opportunity to evaluate the effect of F14 and L14 in a "semi-heterologous" system in which large portions of wild type context defining the 3' and 5' ss of SMN2 exon 7 were present. At the same time, Casp3SMN2 minigene retained the Casp3 context that defines the 5' ss of upstream and 3' ss of downstream exons. As shown in FIG. 5D, when Casp3SMN2 was co-transfected with either F14 or L14, both ASOs promoted exon 7 inclusion. These results indicated that the inhibitory effect of unsequestered $^{10}$C is linked to a long-distance interaction that could not be formed in the context of Casp3SMN2. Our results also suggested that the splicing factors directly interacting with exon 7 and the flanking intronic sequences are not involved in producing inhibitory effect associated with unsequestered $^{10}$C upstream of L14-duplex.

Inhibitory Effect of $^{10}$C is Linked to an Intra-Intronic Long-Distance Interaction Based on the corroborative evidence of experiments described in FIGS. 3-5, the most plausible mechanism of inhibitory effect of unsequestered $^{10}$C would be involvement of a long-distance interaction(s). To explore such possibility, we generated SMN2 minigene mutants with large deletions within intron 6 and intron 7 farther away from the 3' and 5' ss of exon 7. These mutants were then used to test the effect of F14 and L14 on exon 7 splicing. As shown in FIG. 6, when the 3' portion of intron 7 was deleted (I7 Δ190-406) the negative effect of L14 on exon 7 splicing was abrogated and it became almost as effective in restoring the inclusion of exon 7 as F14. However, in SMN2 mutant with a deletion in intron 6 (I6 Δ-80-199D) L14 still retained its inhibitory effect on exon 7 splicing (FIG. 6). Interestingly, when I6 Δ-80-199D deletion was combined with I7 Δ 190-406 deletion (mutant I6 Δ/I7 Δ), L14 again lost its inhibitory effect despite the unsequestered $^{10}$C (FIG. 6B). These results are in line with the effect of F14 and L14 on exon 7 splicing in the hybrid Casp3SMN2 minigene that lacks similar regions of intron 6 and intron 7 (FIG. 5D). The observation that L14 lost its ability to increase exon 7 skipping when the region between positions 188 and 407 of intron 7 was missing provided the first indication of a potential long-distance interaction between untargeted $^{10}$C and a sequence upstream of the 3' ss of exon 8. In other words, our results suggest that the inhibitory effect of untargeted $^{10}$C upstream of L14-duplex is intimately linked to sequences upstream of the 3' ss of exon 8.

Next we wanted to determine if a specific sequence upstream of the 3' ss of exon 8 was involved in long-distance interactions with untargeted $^{10}$C. Since the deletion in the 3' portion of intron 7 that abolished the negative impact of untargeted $^{10}$C in the context of L14-duplex was rather large (from $190^{th}$ and $406^{th}$ positions), we generated several SMN2 mutants with smaller overlapping deletions in this area and co-transfected them with F14 and L14. Based on the results shown in FIG. 7, F14 treatment effectively restored inclusion of SMN2 exon 7 in all mutants, while the response to L14 appeared to depend upon size and location of deletion within intron 7. For example, several sets of overlapping deletions in the 3' region of intron 7 resulted into the loss of inhibitory effect and/or gain of stimulatory effect on exon 7 inclusion when the deletion size was 72 nucleotides or more (FIG. 7). In particular, when mutants SMN2-I7 Δ 195-306 and SMN2-I7 Δ 287-393 with deletions of 112 and 107 nucleotides, respectively, were co-transfected with L14, exon 7 inclusion increased ~2.5 times as compared to "mock" co-transfection (FIG. 7B). At the same time, L14 produced no stimulatory effect on mutant with equally large (115-nucleotide long) deletion in the 5' portion of intron 7 (SMN2-I7 Δ 30-144) (FIG. 7B). Since ISS-N1 harbors the only target site for L14 within entire SMN2, the loss of inhibitory effect of L14 in deletion mutants could be directly linked to the loss of a long-distance interaction associated with the deleted sequences. Based on our results we conclude that long-distance interaction are area specific and not sequence specific. Our results of SMN2 intron 7 deletions do not support a straightforward mechanism of loss of L14 inhibitory effect as a consequence of the reduced size of intron 7. Further supporting this argument, a much larger downstream intron (~1.6 kb) in the heterologous context of Casp3SMN2 fusion minigene did not recapitulate the inhibitory effect of an untargeted $^{10}$C upstream of L14-duplex (FIG. 5D).

Antagonistic Effect of ASOs is not Linked to the Differential Displacement of hnRNP A1 hnRNP A1 motifs located within ISS-N1 have been linked to skipping of SMN2 exon 7 (Hua et al. 2008). Since F14 and L14 produce an opposite effect on exon 7 splicing, we wished to test whether these ASOs display any disparity in their ability to prevent binding of hnRNP A1 to ISS-N1. For this purpose we performed in vitro experiments using a purified recombinant hnRNP A1 protein. The purification of hnRNP A1 was done using an IMPACT (Intein Mediated Purification with an Affinity Chitin-binding Tag) system that allows a single-column purification of an *Escherichia coli* expressed protein without vector-derived amino acids or affinity tags. As shown in the FIG. 8A, we were able to obtain a nearly homogenous (more than 90% pure) hnRNP A1 preparation.

We then used site-specific UV-crosslinking to probe the interaction of the purified hnRNP A1 with ISS-N1. The 50-nucleotide long RNA probe used for UV-crosslinking contained the last 18 residues of exon 7 and the first 32 residues of intron 7 of SMN2, including the ISS-N1 region (FIG. 8B). To capture a direct interaction of hnRNP A1 with ISS-N1, a single radioactive $^{32}$P-moeity was introduced between the $5^{th}$ and the $6^{th}$ residue of ISS-N1. These residues fall within the first hnRNP A1 motif of ISS-N1 (FIG. 1A). The conditions of UV-crosslinking experiments were optimized to obtain the sufficient amount of hnRNP A1-crosslinked product following RNase digestion. The results of site-specific UV-crosslinking confirmed that purified hnRNPA1 binds at the site containing radioactive moiety (FIG. 8C). Having established that hnRNP A1 can be site-specifically crosslinked to ISS-N1, we sought to investigate whether a sequestration of ISS-N1 with F14 or L14 is able to prevent hnRNP A1 binding. For this purpose the site-specifically labeled RNA probe was denatured and refolded in the presence of either F14 or L14 prior to addition of hnRNP A1 and UV-crosslinking. As controls we used the mutant ASOs, F14comp and L14comp. As described earlier, these ASOs produce no antisense effect due to the mismatch mutations (FIG. 2). As shown in FIG. 8D, F14 and L14 were equally efficient in preventing the binding of hnRNP A1 to ISS-N1 as indicated by the substantial decrease in the amount of hnRNP A1-crosslinked product as compared to "No ASO" and F14comp/L14comp controls.

In the next experiment the site-specifically labeled RNA probe was refolded prior to addition of the ASOs and hnRNP A1. Since the ASOs were added to the reaction mixture after the RNA probe was refolded, this experiment validated the accessibility of the target under the native conditions. Also it tested the affinity of hnRNP A1 for its "native" target in the presence of ASOs. Here again we used F14comp and L14comp as control ASOs. As shown in FIG. 8E, again F14 and L14 were equally efficient in preventing hnRNP A1 binding, whereas control ASOs had no effect. Our results also confirmed that sequestration of $^{10}$C was not required for the displacement of hnRNP A1.

An Untargeted Cytosine Decides the Outcome of the Target-Specific Antisense Response ISS-N1 has emerged as one of the best-studied intronic antisense targets for splicing correction in a major human disease. The 15-nucleotide long ISS-N1 has the distinction of harboring two putative hnRNP A1 motifs covering its last 14 residues (Hua et al. 2008). The first five residues of ISS-N1 together with the three upstream residues constitute an 8-nucleotide-long GC-rich motif (FIG. 1A). Sequestration of either GC-rich motif or first fourteen nucleotides of ISS-N1 has the capability to fully restore SMN2 exon 7 inclusion in SMA patient cells at low nanomolar concentrations (Singh et al. 2006, 2009). Based on these findings, the first five residues of ISS-N1 constitute the core of the above two antisense targets (Singh et al. 2009). Although, the GC-rich sequence is the shortest known target for effective splicing correction in a patient cell line, the mechanism by which sequestration of this sequence restores SMN2 exon 7 inclusion is not known. Upon annealing to its target, an ASO has a capability to break the local context by introducing a double helical structure that affects the orientation of residues upstream and downstream of the helix. Hence, an ASO-based approach provides a unique opportunity to test the significance of certain residues at specific positions even though these positions are not directly targeted by an ASO. Here we report a rare finding in which an untargeted cytosine residue at the $10^{th}$ intronic position ($^{10}$C) decides the outcome of the antisense response of ASOs that target sequences immediately downstream of $^{10}$C. A critical role of $^{10}$C was found to stem from its unique location within the GC-rich motif at a precise distance from the 5' ss of exon 7.

The significance of unsequestered $^{10}$C in conferring the outcome of ISS-N1-targeting by ASOs was best captured by F14 and L14. Targets of F14 and L14 differ by a single nucleotide. While F14 sequestered $^{10}$C and produced an expected strong stimulatory response on SMN2 exon 7 inclusion, L14 that did not target $^{10}$C triggered SMN2 exon 7 skipping. The negative effect of L14 was highly surprising, since L14 fully sequestered both of the hnRNP A1 motifs. The opposite effects of F14 and L14 were observed in the context of both, the endogenous gene and the minigene containing genomic sequences from SMN2 exon 6 through exon 8. This confirmed that a specific promoter sequence and/or any region upstream of exon 6 do not drive the antisense effect.

To validate the target specificity of F14 and L14, we took advantage of our meticulously designed mutant minigenes. In the absence of any off-target effect, it is expected that the lack of annealing of ASOs with the mutated target would eliminate the antisense response. Indeed, validating the target specificity, F14 and L14 lost their ability to affect exon 7 splicing in the mutated SMN2/17-08 minigene. In a counter experiment, mutant F14 and L14 that reinstated the base pairing with the mutated ISS-N1 fully restored the original antisense effects. These results confirmed that the antisense effects were driven by duplexes formed between ASOs and their respective intended targets. However, in case of L14, the inhibitory effect was linked to an untargeted $^{10}$C since the deletion of $^{10}$C reversed the effect of L14 on SMN2 exon 7 splicing (FIG. 3A). Further support for the inhibitory role of untargeted $^{10}$C came from SMN2/64A mutant in which $^{10}$C was replaced by $^{10}$A. Since this C-to-A change did not affect SMN2 exon 7 splicing pattern, $^{10}$A provided an ideal substitution to probe the role of an untargeted residue immediately upstream of L14-duplex. L14 was able to fully restore exon 7 inclusion in SMN2/64A. This surprising result constitutes one of the rare findings in which a target-specific antisense response was reversed by an otherwise neutral single nucleotide substitution at the untargeted position. Our results also confirmed that the specific location of untargeted $^{10}$C upstream of L14-duplex with respect to the 5' ss is responsible for the inhibitory effect of L14. Supporting this argument, moving the target sequence away from the 5' ss significantly decreased the inhibitory response of L14 (FIG. 4).

Unique Antisense Response is Modulated by a Context-Specific Long-Distance Interaction We used Casp3 minigene containing ISS-N1 to compare the impact of F14 and L14 in the context of a heterologous system. We have earlier shown that insertion of ISS-N1 downstream of the 5' ss of Casp3 exon 6 promotes skipping of this exon. As expected, F14 fully restored Casp3 exon 6 inclusion. However, L14 also produced a noticeable stimulatory response, clearly suggesting that the inhibitory effect of unsequestered $^{10}$C upstream of L14 duplex is not dependent upon a linear cis-element (FIG. 5). These results provided the first evidence implicating the role of a long-distance interaction that is generally hard (if not impossible) to predict by available algorithms. Our subsequent experiments with a series of deletion mutations in the second half of intron 7 furnished the strong proof in support of such interaction (FIGS. 6, 7). Our results suggested that an unsequestered $^{10}$C in presence of L14-duplex interacts with intron 7 sequences upstream of the 3' ss of exon 8. It is conceivable that the annealing of L14 changes the local structure so that $^{10}$C becomes particularly "accessible" for interactions due to for example flipping. However, further experiments are required to confirm this possibility. One can hypothesize that a long-distance interaction with accessible $^{10}$C might interfere with a catalytic core formation at the 5' ss of exon 7. Consequently, the competing 5' ss of exon 6 becomes the favorable substrate for the transesterification reaction leading to exon 7 skipping (FIG. 9). On the other hand, $^{10}$C sequestered in F14-duplex would be no longer available for interactions, leading to usage of the 5' ss of exon 7 (FIG. 9).

Recent updates reaffirm that spliceosome complexes are massive, dynamic ribonucleoprotein assemblies that undergo extensive remodeling and exchange of components as spliceosomes are constructed, activated and recycled (Smith et al. 2008; Wahl et al. 2009; Newman and Nagai 2010). Prp8 is the largest spliceosomal protein that plays a significant role in formation of catalytic core of spliceosome by establishing contacts with the 5' ss, 3' ss and branch point (Grainger and Beggs 2005). It is possible that specific orientation of untargeted $^{10}$C prevents recruitment of Prp8 and/or its interacting partners that include RNA helicases with unwinding activity of RNA:RNA duplexes. Independent reports suggest that the structural rearrangement within spliceosome must release branch point-binding complexes for the first transesterification reaction to take place (Golas et al. 2005; Lardelli et al. 2010). Hence, it is probable that the specific orientation of the untargeted $^{10}$C affects release of the branch point-binding complexes. Role of specific orientation of the untargeted $^{10}$C is somewhat supported by the observation that 5'1U-F15 ASO that has a 3' uridine overhang eliminates the inhibitory effect associated with L14-duplex (FIG. 3B). Since the overhang is positioned opposite to $^{10}$C, one may hypothesize that either a non-canonical base pairing with $^{10}$C partially alters the orientation of $^{10}$C or the overhang sterically shields $^{10}$C making it inaccessible. As a consequence, the inhibitory effect of untargeted $^{10}$C is reduced. Irrespective of the possible mechanism, our results clearly indicate that the inhibitory effect of unsequestered $^{10}$C is not linked to differential recruitment of hnRNP A1 to ISS-N1 region since L14 and F14 were equally efficient in displacing this inhibitory factor from ISS-N1 (FIG. 8). The discovery of the prominent role of $^{10}$C in this study combined with our recent report regarding splicing modulation by an 8-mer ASO targeting GC-rich sequence, we are tempted to suggest that effect of these ASOs are realized at least in part due to direct remodeling of catalytic core and not merely due to displacement of an inhibitory factor.

Despite the fact that human U2 introns have no preference for a particular residue at the $10^{th}$ intronic position (Burge et al. 1999), a majority (five out of eight) of human SMN introns contain C residue at the $10^{th}$ intronic position. Four of these $^{10}$Cs are also conserved between human and mice SMN introns. In regard to $^{10}$C of ISS-N1, the entire GC-rich sequence is not conserved between human and mouse. It remains to be seen if evolutionary preference for $^{10}$Cs in most human SMN introns is merely a coincidence or a part of a yet to be identified regulatory network. Although, not all $^{10}$C-containing SMN introns are associated with skipping of exons, it cannot be ruled out that the specific residues at the $10^{th}$ intronic position may augment/delay the process of catalytic core formation and intron removal. Our finding that the stimulatory effect in presence of the untargeted $^{10}$C was not at par with the sequestered $^{10}$C in all contexts supports this hypothesis.

The number of reported regulatory elements in the vicinity of the 5' ss of SMN2 exon 7 continues to grow (Singh 2007b; Hua et al. 2008; Gladman and Chandler 2009). Majority of these cis-elements are absent in mouse Smn and seem to be specific to humans. Linear cis-elements and RNA secondary structures define most of these regulatory elements. Deletions and substitution mutations have been able to validate the role of all of the SMN cis-elements elements described so far. In this study, use of an ASO-based approach was able to establish the significance of a single cytosine residue at the $10^{th}$ intronic position that falls within a unique GC-rich sequence. Since several of $^{10}C$ deletion/substitution mutations did not change the splicing pattern of SMN2 exon 7 and yet reversed the antisense response, it became obvious that $^{10}C$ is an integral part of the regulatory network involving long-distance and/or secondary interactions. Role of such interactions have been implicated in several systems (Bartel et al. 1991; Matsuura et al. 2001; Singh et al. 2004c). Future experiments would address the detailed mechanistic aspects that define the very unique 5' ss of a critical exon, skipping of which is associated with a major human disease.

Materials and Methods

Minigenes and Expression Vectors

Minigene splicing cassettes pSMN2 A 16, SMN2/17-8, SMN2/5A, SMN2/5G, N1 Δ 30-34, N1 Δ 25-34, Casp3Avr, Casp3ISS-N1 and SMN2/64A were described earlier (Singh et al. 2004b, 2006, 2009). Mutations, deletions and insertions within minigenes were introduced by PCR using Phusion High-Fidelity DNA polymerase (New England Biolabs). Minigene splicing cassettes Casp3-3'Cl and Casp3ISS-N13'Cl were generated by inserting TTAAATTAA sequence in Casp3Avr and Casp3ISS-N1, respectively, using AvrII restriction site. The exact locations of TTAAATTAA sequence is shown in FIG. 5A. In Casp3-SMN5'-1 minigene the entire SMN sequence from the $43^{rd}$ position of exon 7 to $24^{th}$ position of intron 7 was inserted in Casp3Avr minigene using two-step high fidelity PCR as described earlier (Singh et al. 2007). The same PCR approach was used to generate Casp3SMN2 hybrid minigene, in which the last 116 residues of intron 5 and the entire exon 6 of Casp3 were substituted with the last 116 nucleotides of intron 6, the entire exon 7 and the first 99 nucleotides of intron 7 of SMN2 (FIG. 5D). All minigene constructs were verified by sequencing. All oligonucleotides for cloning and sequencing were obtained from Integrated DNA Technologies.

To generate a bacterial expression vector for human hnRNPA1 recombinant protein, hnRNPA1 coding sequence was inserted in frame with the downstream *Mycobacterium xenopi* GyrA intein/chitin binding domain in pTXB3 plasmid (New England Biolabs). hnRNPA1 sequence was amplified from an hnRNPA1 expression vector provided by Dr. Benoit Chabot (LaBranche et al. 1998). For cloning purposes position 51 in hnRNP A1 coding sequence was mutated by a two-step PCR amplification. The 5' portion of hnRNPA1 was amplified with a pair of primers 5' RNPA-imp2 (GTGGTG-GTA*CCATGG*CCTCTAAGTCAGAGTCTCCTAAAGA-GCCCGAACAG) (SEQ ID NO:26) and 3'RNPA-U mut (CCCTCCAATaAAGAGCTTCCTCAGCTGT-TCGGGCTC), (SEQ ID NO:27) where NcoI restriction site is underlined, and an A to T mutation at position 51 is indicated by a small-case letter. This mutation is translationally silent but destroys a SapI restriction site in a wild type hnRNP A1. As a part of our cloning strategy a GCC codon was added at the beginning of hnRNP A1 sequence in 5' RNPA-imp2 primer (indicated in italic). This codon helps to create an NcoI restriction site, which itself contains an ATG sequence used for translation initiation. To amplify the 3' portion of hnRNPA1 sequence, we used a pair of primers 5'RNPA-U mut (AGGAAGCTCTTtATTGGAGGGT-TGAGCTTTGAAAC) (SEQ ID NO:28) and 3'RNPA-imp (CTGGTGGTT GCTCTTCCGCAAAATCTTCTGCCACTGCCATAGCT-AC) (SEQ ID NO:29) with an A to T mutation at position 51 indicated by a small-case letter and SapI restriction site is underlined. The 3'RNPA-imp primer deletes the termination codon of hnRNP A1 and introduces the SapI restriction site followed by the first codon of *Mycobacterium xenopi* GyrA intein fused to the last codon of hnRNPA1. This primer design guarantees that after intein-mediated cleavage of the fusion protein (see protein purification procedure) the recombinant hnRNPA1 will have no additional amino acids at its C-terminus. The 5' and 3' portions of hnRNPA1 were gel-purified and ligated in the second step PCR reaction using the primers 5' RNPA-imp2 and 3'RNPA-imp. The PCR product corresponding to the full-length hnRNP A1 was gel-purified, digested with NcoI and Sap I and cloned between the corresponding sites of pTXB3 vector. The resulting hnRNP A1 bacterial expression vector, pTXB3-A1, was confirmed by sequencing. As a result of the cloning strategy, the hnRNP A1 protein expressed from pTXB3-A1 contains one extra amino acid appended to the N-terminus.

Cell Culture

The *E. coli* strain ER2566 (New England Biolabs) was used for expression of the recombinant hnRNP A1 protein. The strain was grown in LB medium supplemented with 100 μg/ml of ampicillin. HeLa cells obtained from the American Type Culture Collection were cultured in Dulbecco's modified Eagle's medium (DMEM) supplemented with 10% fetal bovine serum (FBS). Primary fibroblast cell line from SMA type I patient (Repository number GM03813) was obtained from Coriell Cell Repositories. These cells were maintained in MEM supplemented with 2 mM GlutaMAX-I and 15% FBS. All tissue culture media and supplements were purchased from Invitrogen.

Antisense Oligonucleotides

RNA antisense oligonucleotides (ASOs) were synthesized by Dharmacon Inc. or by TriLink Biotechnologies. ASOs incorporated 2'-O-methyl modification and phosphorothioate backbone (2OMePS) as described earlier (Singh et al. 2006). LNAs containing uniform phosphorothioate backbone were synthesized by Exiqon.

Transfections and In Vivo Splicing Assays

Transient transfections of cells with plasmid DNA and/or with ASOs were performed using Lipofectamine 2000 (Invitrogen) following the manufacturer's recommendations. Briefly, cells were plated 24 h prior to transfection so that their density on the day of transfection was ~80%. Oligonucleotide concentration varied and specified in figure legends. Depending on the experiment the amount of the plasmid used for transfection was either 0.1 or 0.8 μg. In a given experiment, the total amount of ASO was maintained constant by adding the control oligonucleotide (5'UUGCCUUUCU3'). (SEQ ID NO:30) The transfection efficiency of an ASO was measured in a parallel experiment with the fluorescent labeled control ASO along with the experimental ASO. Total RNA was isolated at the indicated time points using Trizol reagent (Invitrogen). To generate cDNA reverse-transcription was carried out using SuperScript III Reverse Transcriptase (Invitrogen) and Oligo (dT) primer (Invitrogen). Minigene-specific spliced products were identified using Taq DNA polymerase (Invitrogen) and the following pairs of primers: P1 and P2 for SMN2 minigene (Singh et al. 2004b); P1 and P56 for Casp3Avr-based minigenes (Singh et al. 2006), and N-24 and P2 for endogenous SMN (Singh et al. 2006). PCR reactions were performed in the presence of a trace amount of [a-$^{32}$P] dATP (3000 Ci/mmole, Perkin-Elmer). Analysis and quantifications of spliced products were performed using a FPL-5000 Image Reader and Multi Gauge software (Fuji Photo Film Inc.). Results were confirmed by at least three independent experiments. Standard deviation was less than 5% of mean.

Purification of hnRNP A1 Protein

*E. coli* ER2566 was transformed with pTXB3-A1 expression plasmid and plated on LB-agar plates containing ampicillin. A single freshly grown colony from the LB plate was inoculated into 5 ml of LB medium with ampicillin and grown overnight at 37° C. The entire 5 ml of the overnight culture was then used to inoculate 500 ml of fresh LB medium with ampicillin, and bacterial growth continued until the $OD_{600}$ of the culture reached 0.8. At this moment the culture was shifted to 30° C., and the protein expression was induced with 0.2 mM IPTG for 5 h. All subsequent steps were carried out at 4° C. The cells were harvested by centrifugation at 6,000 rpm for 10 min (Sorvall Legend RT+ centrifuge, Thermo Scientific), and the cell pellet was re-suspended in 10 ml of ice-cold column buffer (CB) [20 mM Na-HEPES, pH 8.5, 1 mM EDTA, 500 mM NaCl] supplemented with Protease Inhibitor Cocktail (Roche). Cells were lysed by sonication on ice at 5 watts for five 10 s bursts, with 60 s intervals (Microson™ Ultra sonic cell disruptor, Misonix Inc.) followed by centrifugation at 12,000 rpm for 15 min to remove cell debris. For affinity chromatography, the lysate was diluted to 50 ml with ice-cold CB and slowly loaded on a chitin (New England Biolabs) column (BioRad; 10 ml plastic column with a 5 ml bed volume) equilibrated at 4° C. with 50 ml of CB. The column was then washed with 100 ml of CB, followed by another wash with 50 ml of CB, in which NaCl concentration was increased from 500 to 700 mM. The hnRNPA1 protein was released by inducing an on-column intein self-cleavage in the presence of DTT. To induce intein self-cleavage, the column was quickly flushed with 15 ml of CB containing 50 mM DTT. The column flow was stopped, and the column was left overnight at 4° C. The freed hnRNPA1 protein was eluted from the column with CB. Elution fractions of 1 ml were collected, and the hnRNPA1 protein was recovered in the first nine fractions. The pooled fractions were de-salted using NAP columns (GE Healthcare) and stored in 50% glycerol at −80° C. The eluted protein was analyzed by electrophoresis in 10% SDS-polyacrylamide gels, stained with Coomassie blue. Protein concentration was determined against BSA standards run on a SDS-polyacrylamide gel.

Generation of Site-Specifically Labeled RNA Probe

All synthetic RNA oligonucleotides used to generate a site-specifically $^{32}$P-labeled probe were obtained from Dharmacon Inc. The 3' portion of the probe, 5DN-18 (AUUAUGAAAGUGAAUCUU) (SEQ ID NO:31), was 5'-end-labeled using [γ-$^{32}$P] ATP (3000 Ci/mmole, Perkin-Elmer) and T4 polynucleotide kinase (New England BioLabs) followed by phenol:chloroform extraction and ethanol precipitation. The 5'-end-labeled 5DN-18 fragment was then ligated to the 5' portion of the probe, TSL2-U1-32 (CAUUCCUUAAAUUAAGGAGUAAGUCUGCCAGC) (SEQ ID NO:32) using T4 DNA ligase (New England Biolabs) and a bridging DNA oligonucleotide (GGAATT-TAATTCCTCATTCAGACGGTCGTAATACTTTCAC). (SEQ ID NO:33) The bridging oligonucleotide was complementary to 28- and 12-nucleotide-long segments on the 5' and 3' portions of the probe, respectively (FIG. 8B). Briefly, two RNA fragments were hybridized to the bridging DNA by mixing 50 pmoles of 5DN-18, 50 pmoles TSL2-U1-32 and 100 pmoles of bridging DNA, and 2 μL 10×DNA ligation buffer (New England Biolabs) in a 16 μL reaction mixture. The mixture was heated at 75° C. for 2 min and shifted to 37° C. At this point 20 units of Superase (Ambion) were added to the reaction mixture, and the incubation proceeded for three hours. The hybridized substrates were then ligated by adding 20 nmoles of ATP and 400 unit of T4 DNA ligase (New England Biolabs). The ligation was carried out for 4 hours at 37° C. The ligated RNA product was gel purified in a denaturing 16% polyacrylamide gel containing 8 M urea. The RNA product was eluted overnight at 37° C. using the 'crush and soak' method (Singh et al. 2006), and precipitated with ethanol.

UV-Crosslinking

For UV-crosslinking under native condition, the site-specifically $^{32}$P-labeled RNA probe was first denatured at 90° C. for 3 min and refolded at 37° C. for 1 hour. 50 ng of the refolded probe was then used in a 50 μL crosslinking reaction containing 20 mM Tris-Cl pH 7.6, 200 mM KCl, and 2 mM $MgCl_2$. When needed, 0.6 μM of an ASO of interest was used in crosslinking reaction. Initial experiments were done in native condition in which RNA probe was first refolded by heating at 90° C. for 3 min followed by slow cooling to room temperature. Next, refolded RNA probe and the ASO were incubated at 37° C. for 1 hour before 2.5 μg of hnRNP A1 was added, the reaction was then moved to ambient temperature, and the incubation continued for another 10 min. The UV-crosslinking of RNA-protein complexes was carried out on ice at a distance of 0.5 cm for 15 min using a hand-held UV-transilluminator (254 nm, UVG 54, UVP). After crosslinking, the RNA was digested with 1 unit RNAse T1 (USB) and 1 μg RNAse A (TEKnova) at 37° C. for 30 min. The cross-linked products were resolved by electrophoresis on a 13% SDS-polyacrylamide gel, which was then dried and analyzed using a FPL-5000 Image Reader (Fuji Photo Film Inc.).

For UV-crosslinking under denaturing condition, 50 ng of the RNA probe was added to a 50 μL crosslinking reaction containing 20 mM Tris-HCl pH 7.6, 200 mM KCl and 2 mM $MgCl_2$ with or without 0.6 μM ASO. The reaction mixture was heated to 90° C. for 3 min and moved to 37° C. for an overnight incubation. This refolding of the RNA and an ASO together insures that the latter will anneal to its target sequence. Following the overnight incubation 2.5 μg of hnRNP A1 was added to the reaction, and it was shifted to an ambient temperature for 10 min. UV-crosslinking and detection of RNA-hnRNP A1 crosslinked products were done similarly as described for "native" conditions. FIG. 10 shows the putative sites for long distance interaction and new oligos designed to interact with this site and with other locations in intron 7.

```
1. F5LNA (Targets GC-rich sequence and LDT1 in SMN2 intron 7)
   Oligonucleotide sequence: 5'-GCTGG-3'
   Oligonucleotide chemistry: Phosphorothioate backbone and
   locked nucleic acid modification 2. 2UP5LNA (Targets GC-rich sequence in SMN2 intron 7)
   Oligonucleotide sequence: 5'-TGGCA-3'
   Oligonucleotide chemistry: Phosphorothioate backbone and
   locked nucleic acid modification
```

```
3. 3UP5LNA (Targets GC-rich sequence in SMN2 intron 7)
   Oligonucleotide sequence: 5'-GGCAG-3'
   Oligonucleotide chemistry: Phosphorothioate backbone and
   locked nucleic acid modification 4. TRGT16GC (Targets LDT2 in SMN2 intron 7)
   Oligonucleotide sequence: 5'-CCUCUGUGGACACCAG-3' (SEQ ID NO: 62)
   Oligonucleotide chemistry: Phosphorothioate backbone and
   2'-O-methyl modification in sugar moiety LDT = Long-distance target
```

In a preferred embodiment, one of more oligos may be combined for example, an intron 7 oligo combined with a long distance target oligo for a synergistic response.

REFERENCES

Bartel D P, Zapp M L, Green M R, Szostak J W. 1991. HIV-1 Rev regulation involves recognition of non-Watson-Crick base pairs in viral RNA. *Cell* 67:529-536.

Bauman J, Jearawiriyapaisarn N, Kole R. 2009. Therapeutic potential of splice-switching oligonucleotides. *Oligonucleotides* 19:1-14.

Buratti E, Baralle M, Baralle F E. 2006. Defective splicing, disease and therapy: searching for master checkpoints in exon definition. *Nucleic Acids Res* 34:3494-3510.

Buratti E, Dhir A, Lewandowska M A, Baralle F E. 2007. RNA structure is a key regulatory element in pathological ATM and CFTR pseudoexon inclusion events. *Nucleic Acids Res* 35:4369-4383.

Burge C B, Tuschl T, Sharp P A. 1999. Splicing of precursors to mRNAs by the spliceosomes. In *The RNA world,* 2nd ed. (eds. R. F. Gesteland et al.), pp. 525-560. Cold Spring Harbor Laboratory Press, Cold Spring Harbor, N.Y.

Chasin L A. 2007. Searching for splicing motifs. *Adv Exp Med Biol* 623: 85-106.

Cooper T A, Wan L, and Dreyfuss G. 2009. RNA and disease. *Cell* 136:777-793.

David C J, Manley J L. 2008. The search for alternative splicing regulators: new approaches offer a path to a splicing code. *Genes & Dev* 22: 279-285.

Garcia-Blanco M A. 2006. Alternative splicing: therapeutic target and tool. *Prog Mol Subcell Bio* 44: 47-64.

Gladman J T, Chandler D S. 2009. Intron 7 conserved sequence elements regulate the splicing of the SMN genes. *Hum Genet.* 126: 833-841.

Golas M M, Sander B, Will C L, Lührmann R, Stark H. 2005. Major conformational change in the complex SF3b upon integration into the spliceosomal U11/U12 di-snRNP as revealed by electron cryomicroscopy. *Mol Cell* 17:869-83.

Graveley B R. 2005. Mutually exclusive splicing of the insect Dscam pre-mRNA directed by competing intronic RNA secondary structures. *Cell* 123: 65-73.

Grainger R J, Beggs J D. 2005. Prp8 protein: at the heart of the spliceosome. *RNA* 11: 533-557.

Hertel K J. 2008. Combinatorial control of exon recognition. *J Biol Chem* 283: 1211-1215.

Hua Y, Vickers T A, Okunola H L, Bennett C F, Krainer A R. 2008. Antisense masking of an hnRNP A1/A2 intronic splicing silencer corrects SMN2 splicing in transgenic mice. *Am J Hum Genet.* 82: 834-848.

LaBranche H, Dupuis S, Ben-David Y, Bani M R, Wellinger R J, Chabot B. 1998. Telomere elongation by hnRNP A1 and a derivative that interacts with telomeric repeats and telomerase. *Nat Genet.* 19: 199-202.

Lardelli R M, Thompson J X, Yates J R 3rd, Stevens S W. 2010. Release of SF3 from the intron branchpoint activates the first step of pre-mRNA splicing. *RNA* 16: 516-528

Lefebvre S, Burglen L, Reboullet S, Clermont O, Burlet P, Viollet L, Benichou B, Cruaud C, Millasseau P, Zeviani M, et al. 1995. Identification and characterization of a spinal muscular atrophy-determining gene. *Cell* 80:1-5.

Lin S, Fu X D. 2007. SR proteins and related factors in alternative splicing. *Adv Exp Med Biol* 623: 107-122.

Martinez-Contreras R, Cloutier P, Shkreta L, Fisette J F, Revil T, Chabot B. 2007 hnRNP proteins and splicing control. *Adv Exp Med Biol* 623: 123-147.

Matlin A J, Moore M J. 2007. Spliceosome assembly and composition. *Adv Exp Med Biol* 623: 14-35.

Matsuura M, Noah J W, Lambowitz A M. 2001. Mechanism of maturase-promoted group II intron splicing. *EMBO J* 20:7259-70.

Newman A J, Nagai K (2010) Structural studies of the spliceosome: blind men and an elephant. *Curr Opin Struct Biol* 20, 82-89.

Nilsen T W. 2003. The spliceosome: the most complex macromolecular machine in the cell. *Bioessays* 25: 1147-1149.

Nilsen T W, Graveley B R. 2010. Expansion of eukaryotic proteome by alternative splicing. Nature 463: 457-463.

Ooms M, Verhoef K, Southern E, Huthoff H, Berkhout B. 2004. Probing alternative foldings of the HIV-1 leader RNA by antisense oligonucleotide scanning arrays. *Nucleic Acids Res.* 32: 819-27.

Shepard P J, Hertel K J. 2008. Conserved RNA secondary structures promote alternative splicing. *RNA* 14: 1463-1469.

Singh N N, Androphy E J, Singh R N. 2004a. The regulation and regulatory activities of alternative splicing of the SMN gene. *Crit. Rev Eukaryot Gene Expr* 14: 271-285.

Singh N N, Androphy E J, Singh R N. 2004b. An extended inhibitory context causes skipping of exon 7 of SMN2 in spinal muscular atrophy. *Biochem Biophys Res Commun* 315: 381-388.

Singh N N, Androphy E J, Singh R N. 2004c. In vivo selection reveals combinatorial controls that define a critical exon in the spinal muscular atrophy genes. *RNA* 10: 1291-305.

Singh N K, Singh N N, Androphy E J, Singh R N. 2006. Splicing of a critical exon of human Survival Motor Neuron is regulated by a unique silencer element located in the last intron. *Mol Cell Biol* 26: 1333-1346.

Singh N N, Singh R N, Androphy E J. 2007. Modulating role of RNA structure in alternative splicing of a critical exon in the spinal muscular atrophy genes. Nucleic *Acids Res* 35: 371-389.

Singh R N. 2007a. Unfolding the mystery of alternative splicing through a unique method of in vivo selection. Front Biosci 12: 3263-3272.

Singh R N. 2007b. Evolving concepts on human SMN pre-mRNA splicing. RNA Biol 4: 7-10.

Singh N N, Shishimorova M, Cao L C, Gangwani L, Singh R N. 2009. A short antisense oligonucleotide masking a unique intronic motif prevents skipping of a critical exon in spinal muscular atrophy. *RNA Biol* 6:341-350.

Smith D J, Query C C, Konarska M M. 2008. "Nought may endure but mutability": spliceosome dynamics and the regulation of splicing. *Mol Cell* 30: 657-666.

Tazi J, Bakkour N, Stamm S. 2009. Alternative splicing and disease. *Biochim Biophys Acta* 1792:14-26.

Veedu R N, Wengel J. 2009. Locked nucleic acid as a novel class of therapeutic agents. *RNA Biol.* 6, 321-323.

Vitte J, Fassier C, Tiziano F D, Dalard C, Soave S, Roblot N, Brahe C, Saugier-Veber P, Bonnefont J P, Melki J. 2007. Refined characterization of the expression and stability of the SMN gene products. *Am J Pathol* 171: 1269-1280.

Wahl M C, Will C L, Lührmann R. 2009. The spliceosome: design principles of a dynamic RNP machine. *Cell* 136: 701-718.

Wang Z, Burge C B. 2008. Splicing regulation: from a parts list of regulatory elements to an integrated splicing code. *RNA* 14:802-13.

Ward A J, Cooper T A. 2010. The pathology of splicing. *J Pathol* 220: 152-163.

Warf M B, Diegel J V, von Hippel P H, Berglund J A. 2009. The protein factors MBNL1 and U2AF65 bind alternative RNA structures to regulate splicing. *Proc Natl Acad Sci USA* 106:9203-9208.

Williams J H, Schray R C, Patterson C A, Ayitey S O, Tallent M K, Lutz G J. 2009. Oligonucleotide-mediated survival of motor neuron protein expression in CNS improves phenotype in a mouse model of spinal muscular atrophy. *J Neurosci* 29:7633-8.

Wirth B, Brichta L, Hahnen E. 2006. Spinal muscular atrophy and therapeutic prospects. *Prog Mol Subcell Biol* 44:109-132.

Xing Y, Lee C. 2007. Relating alternative splicing to proteome complexity and genome evolution. *Adv Exp Med Biol* 623:36-49.

Yu Y, Maroney P A, Denker J A, Zhang X H, Dybkov O, Lührmann R, Jankowsky E, Chasin L A, Nilsen T W. 2008. Dynamic regulation of alternative splicing by silencers that modulate 5' splice site competition. *Cell* 135:1224-1236.

Example 2

Materials and Methods

Plasmids, cells and ASOs. Construction of SMN2 minigene is described earlier.[35] Construct SMN2/64A contains a C-to-A mutation in SMN2 minigene and was generated by PCR using Phusion High-Fidelity DNA polymerase (New England Biolabs). HeLa cells were obtained from the American Type Culture Collection and were cultured in Dulbecco's modified Eagle's medium (DMEM) supplemented with 10% fetal bovine serum (FBS). Primary fibroblast cell line from SMA type I patient (Repository number GM03813) and a healthy control (Repository number AG06814) were obtained from Coriell Cell Repositories. These cells were maintained in MEM supplemented with 2 mM GlutaMAX-1 and 15% FBS. All tissue culture media and supplements were purchased from Invitrogen. RNA ASOs used in our study were synthesized by Dharmacon Inc. These ASOs incorporated 2'-O-methyl modification and phosphorothioate backbone (2OMePS) as described earlier.

Transfections and In Vivo Splicing Assays.

Transient transfections of cells with plasmid DNA and/or with ASOs were performed using Lipofectamine 2000 (Invitrogen) following the manufacturer's recommendations. Briefly, cells were plated 24 h prior to transfection so that their density on the day of transfection was ~80%. Oligonucleotide concentration ranged from 1 to 100 nM. In a given experiment, the total amount of oligonucleotide was maintained constant by adding the control oligonucleotide (5'TGA-CATCCACTTTGCCTTTCTCTC3') (SEQ ID NO: 63). Total RNA was isolated at the indicated time points using Trizol reagent (Invitrogen). To generate cDNA reverse-transcription was carried out using SuperScript III Reverse Transcriptase (Invitrogen) and Oligo (dT) primer (Invitrogen). 1 µg and 3 µg of total RNA were used per 20 µA of reaction for amplification of minigene-specific and endogenous spliced products, respectively. Minigene-specific spliced products were identified using Taq polymerase (Invitrogen) and the pair of primers P1 and P2 for SMN2 minigenes. For PCR amplification of endogenous exons the following primer combinations were used: N-24 and P2 for SMN exon 7; 5'Ex4hSMN-RP (5'GGCCAAGACTGGGACCAGG3') (SEQ ID NO: 34) and 3'SPL8 (5'TGGTGTCATTTAGTGCTGCT3') (SEQ ID NO: 35) or 5'Ex4last1192 (5'AGGGCCAAGACTGGGACCAG-GAAAGG3') (SEQ ID NO: 36) and 3'Exon6SMN (5'CATATAATAGCCAGTATGATAGCC3') (SEQ ID NO: 37) for SMN exon 5; 5'Exon1SMN (5'CTGTTCCGGCGCG-GCACAGGCCAG3') (SEQ ID NO: 38) and 3'Exon4SMN (5'TCACTTTCATCTGTTGAAACTTGG3') (SEQ ID NO: 39) for SMN exon 3. PCR reactions were performed either in the presence of a trace amount of $[\gamma\text{-}^{32}P]$ dATP (3000 Ci/mmole) or with one of the primers being 5' end-labeled. Primers were end-labeled using $[\gamma\text{-}^{32}P]$ATP (3000 Ci/mmole) and T4 polynucleotide kinase (NEB), followed by phenol: chloroform extraction and spinning through a Micro Bio-spin 30 Chromatography Column (Bio-Rad) to get rid of unincorporated $[\gamma\text{-}^{32}P]$ATP. Analysis and quantifications of spliced products were performed using a FPL-5000 Image Reader and Multi Gauge software (Fuji Photo Film Inc.). Results were confirmed by at least three independent experiments.

Western Blot Analysis.

Whole-cell extracts were prepared using ice-cold RIPA buffer (Boston BioProducts) supplemented with protease inhibitor cocktail (Roche Applied Science). Protein concentrations were determined using BSA Protein Assay Kit (Thermo Scientific). Cell extracts were resolved on a 10% (w/v) SDS-PAGE gel and transferred onto polyvinylidene fluoride (BioTrace PVDF) membrane (Pall Life Sciences). The following primary and secondary antobodies were used: mouse monoclonal anti-SMN (BD Transduction Laboratories), mouse monoclonal anti-hnRNP Q (Sigma), rabbit polyclonal anti-Tra2 (Abcam), rabbit polyclonal anti-actin (Sigma), horseradish-peroxidase-conjugated secondary antibodies against mouse (Sigma) and rabbit (Jackson Immuno Research). Mouse monoclonal anti-Gemin 2 and anti-Gemin 8 antibodies were kindly provided by Dr. Gideon Dreyfuss. Mouse monoclonal anti-ZPR was the same as described earlier. In most cases, the membranes were stripped (15 min at room temperature) using Restore Western Blot Stripping Buffer (Thermo Scientific) and re-probed. The membranes were scanned using UVP BioSpectrum AC Imaging System (UVP). Signal intensities were quantified using Vision works LS Image Acquisition and Analysis software (UVP). Results were confirmed by at least three independent experiments.

Immunofluorescence Analysis.

Patient fibroblasts (GM03813) were cultured on coverslips and transfected with 40 nM of F8 (control) and 3UP8 CY3-labeled ASOs using Lipofectamine 2000 as described above. Cells were harvested 48 hr post-transfection, washed, fixed and processed for immunofluorescence. Double labeling (ZPR1/SMN) was carried out by sequential incubations with anti-SMN (clone 8, BD Transduction laboratories), Alexa 633-conjugated anti-mouse IgG secondary antibody (Molecular Probes) and then with FITC-conjugated LG1 (anti-ZPR1). The cover slips were mounted on slides using Vectashield with DAPI (Vector Laboratories) and examined by indirect immunofluorescence using LSM510 confocal microscope (Carl Ziess) equipped with 405 nm diode laser.
Results An Ultra-Refined Antisense Microwalk Revealed Shortest Motif for Splicing Correction.

Recent reports have confirmed the presence of a negative context located downstream of the 5' splice site (5' ss) of SMN2 exon 7. This negative context is defined by a 15-nucleotide cis-element, ISS-N1 that harbors two putative hnRNP A1/A2 motifs (FIG. 11A). ISS-N1 partially overlaps with an octamer sequence CUGCCAGC, which is the only GC-rich sequence in the first half of the intron 7 of human SMN. This sequence is predicted to reside in a single-stranded region sandwiched between two stem-loop structures (FIG. 11A). Combined with an easy accessibility and the high GC-rich content (75%), this octamer sequence has a potential to provide an ideal ASO target. However, it is not known if a short RNA:RNA duplex formed between CUGCCAGC and an ASO could displace an interacting protein and/or drastically change the negative context to reverse the splicing pattern. To explore such possibility, we performed an ultra-refined antisense microwalk downstream of the 5' ss of SMN2 exon 7. All ASOs used in our study incorporated 2'-O-methyl modification and phosphorothioate backbone (abbreviated as "2OMePS"), a widely used RNA modification with proven stability in vivo. We performed our experiments in commercially available SMA type I patient cells (GM03183), which serves as an ideal system for testing of splicing-correcting compounds in the context of the disease caused by the lack of SMN1.

Our ultra-refined antisense microwalk used four groups of ASOs of varying sizes. The ASOs from each group sequestered 0, 1, 2 or 3 residues upstream of ISS-N1. Accordingly, ASOs were named as F, 1UP, 2UP and 3UP, followed by a number representing the size of the ASO (Table A). To discriminate between the most and the least efficient ASOs, the antisense microwalk was performed at four concentrations: 1 nM, 10 nM, 50 nM and 100 nM (Table A). FIG. 11 shows the splicing pattern of representative ASOs performed at 20 nM. We observed a decrease in the antisense effect on exon 7 inclusion with a decrease in the size of F, 1UP and 2UP ASOs (Table A, FIG. 11B). However, the results were drastically different with 3UP ASOs: shortening of ASOs from 14 nucleotides to 8 nucleotides produced no significant changes in their stimulatory effects on exon 7 splicing (FIG. 11B). However, the stimulatory effect drastically decreased when ASO size was further reduced from 8 nucleotides to 7 nucleotides. Hence, we conclude that the shortest ASO to effectively restore SMN2 exon 7 inclusion was 3UP8, an 8-mer ASO that sequestered the entire octamer sequence, CUGCCAGC, discussed above. Remarkably, 3UP8 was able to fully restore SMN2 exon 7 inclusion at a relatively low concentration of 50 nM (Table A).

The finding that 3UP8 restores SMN2 exon 7 inclusion marks the discovery of the shortest ASO among ~200 ASOs tested thus far in SMA patient cells (Table A). In addition to revealing the shortest stimulatory ASO, the ultra-refined microwalk was able to accurately define the first five residues (CCAGC) of ISS-N1 as the core sequence of the antisense target. Our finding of core sequence brings a parallel with seed sequence required for miRNA and siRNA response.

Similar to seed sequence, sequestering of the core sequence was essential but not sufficient for the antisense response. In addition to sequestration of core sequence, sequestration of additional three residues (CUG) upstream of ISS-N1 was found to be essential to obtain the shortest stimulatory ASO. In the absence of the sequestration of CUG residues, an 11-nucleotide or longer target was required for realizing the stimulatory response (Table A). Underscoring the overlapping nature of splicing cis-elements and their hard-to-predict accessibility during the dynamic process of splicing, we found no direct correlation between the size of ASOs and their stimulatory response. Similarly, we found no direct correlation between sequestration of any of the individual hnRNP A1 motifs and the level of stimulatory response. For instance, F10 and L13 fully sequestered the $1^{st}$ and the $2^{nd}$ hnRNP A1 motifs, respectively, and yet did not produce any significant stimulatory response even at higher concentration of 100 nM (Table A). On the other hand, 3UP8 restored SMN2 exon 7 by sequestering an 8-mer motif that only partially overlaps the first hnRNP A1 motif.

Antisense Effect is Specific to Base Paring with the Target.

Having discovered that a short intronic motif could be targeted for splicing modulation of endogenous pre-mRNA, we next examined the efficacy and specificity of short ASO in SMN2 minigene system. Here HeLa cells were co-transfected with the minigene (0.1 μg) and an ASO of interest (50 nM) and the effect on splicing was accessed by RT-PCR. As shown in FIG. 12B, the ASO effect on splicing of minigene-derived exon 7 was consistent with the results for the endogenous SMN2 with 3UP8 being the shortest ASO to fully restore exon 7 inclusion. To compare the target specificity between long and short ASOs, we generated a mutant minigene, SMN2/64A. This minigene has a single C to A substitution at the first position of ISS-N1, hence has capability to weaken the RNA:RNA duplex between the antisense and the target (FIG. 12A). Indeed, our shortest ASO (3UP8) lost all its stimulatory response in SMN2/64A. As expected, a mutant 8-mer ASO (3UP8/64A) that reinstated the base pairing with the mutated target fully restored exon 7 inclusion in SMN2/64A minigene; at the same time 3UP8/64A had no stimulatory effect on splicing of SMN2 minigene (FIG. 12B). Note that the stimulatory impact of 3UP8/64A in SMN2/64A minigene was realized despite the fact that the C-to-A mutation reduced the GC content of the target from 75% to 62.5%. Unlike 8-mer ASOs, all four 15-mer ASOs we used effectively restored exon 7 inclusion in SMN2/64A. These results clearly suggest that an increase in ASO size could have drastic (negative) consequences on the specificity of the antisense response since longer ASO appear to be more "tolerant" to single-nucleotide mismatches.

The Shortest Stimulatory ASO has No Off-Target Effect on Other SMN2 Exons.

To examine the possible off-target effect of ASOs that promote SMN2 exon 7 inclusion in GM03183 cells, we focused on splicing of SMN2 exons 3 and 5. These exons are known to undergo alternative splicing; and therefore, have a potential to regulate the levels of full-length SMN. We have earlier reported that a 5 nM concentration of Anti-N1 had no detectable effect on splicing pattern of SMN2 exons 3 and 5. Here we increased the ASO concentration to 20 and 100 nM. We chose to use Anti-N1, F14 and 3UP8 to represent the longest, the intermediate and the shortest stimulatory ASO, respectively. F8 served as a negative control.

We started with the amplification of endogenous SMN2-spliced products using a pair of primers located within exons 4 and 8. This primer combination provided an added advantage of simultaneous detection of skipping of exons 5 and 7.

To compare the amount of the spliced products in broad size range, we used an end-labeled primer. As shown in FIG. 13A, all three functional ASOs: Anti-N1, F14 and 3UP8, were highly efficient in promoting exon 7 inclusion at 20 nM concentration, while F8 produced no effect. None of the ASOs appeared to have a pronounced effect on splicing of exon 5 at both ASO concentrations. At the same time, Anti-N1, F14 and 3UP8 caused a decrease in the amount of the co-exclusion product (mRNAs lacking both exons 5 and 7), especially at 100 nM (FIG. 13A). Skipping of exon 5 was separately measured with another primer pair that annealed to exons 4 and 6. We found no significant difference on effect on exon 5 splicing in cells treated with any of the tested ASOs (FIG. 13B). To monitor skipping of SMN2 exon 3, we used a forward primer that annealed to exon 1 and the reverse primer that annealed to exon 4. As shown in FIG. 13C, F14 and 3UP8 produced no detectable change in the level of exon 3 skipping as compared to the mock-transfected sample. Contrary to this, Anti-N1 produced a substantial increase in SMN2 exon 3 skipping at 100 nM (FIG. 13C). Mechanism by which Anti-N1 elicits this off target effect is not understood, although it clearly underscores the disadvantage of long ASOs as the therapeutic molecules.

Restoration of SMN Levels by Shortest ASO in SMA Patient Cells.

The next goal of our study was to determine whether the correction of SMN2 exon 7 splicing by 3UP8 resulted in SMN protein increase in patient cells. In particular, we wanted to compare the stimulatory effect of 3UP8 with a longer ASO, Anti-N1. F8 served as the negative control. The experiments were performed with 40 nM of a given ASO and protein levels were determined 48 hours after transfection. Simultaneously, we monitored the levels of SMN2 exon 7 inclusion. As shown in FIG. 14A, mock-treatment (mock) or treatment with F8 did not produce any change in SMN levels (left panel) as well as in levels of SMN2 exon 7 inclusion (right panel). In contrast, treatment with 3UP8 resulted in a substantial up regulation of SMN levels (FIG. 14A, left panel) and SMN2 exon 7 inclusion (FIG. 14A, right panel). Significantly, the effect of 3UP8 on SMN levels was comparable to the effect produced by Anti-N1 treatment. To determine whether increase in SMN levels in ASO-treated patient cells was accompanied by a change in cellular metabolism, we performed western blot for a number of proteins that are generally down regulated in SMA. As shown in FIG. 14A (left panel), treatment of patient cells with 3UP8 was accompanied by a marked increase in the levels of Gemin 2 and Gemin 8. These factors are associated with SMN complex, a macromolecule essential for the housekeeping role of snRNP biogenesis.[26,27] We also observed an increase in the levels of ZPR1 (FIG. 14A), another SMN-interacting protein, reduced expression of which is associated with the progressive loss of motor neurons.[51,52] Interestingly, the correction of splicing by 3UP8 resulted in increase of levels of splicing factors Tra2-β1 and hnRNP Q. Tra2-β1 and hnRNP Q have been shown to promote SMN2 exon 7 inclusion and are generally down regulated in SMA. Thus, our findings suggest that SMN may be a part of a positive feedback loop that provides signals to increase the levels of different splicing factors.

Cell division and degradation of ASOs are bound to attenuate the stimulatory effect of ASOs with respect to time. To determine the sustainability of a single 3UP8 treatment, we performed a time course analysis in which levels of SMN and other factors were examined at 24 hr intervals for six days. Simultaneously, we also monitored ASO effect on SMN2 exon 7 splicing. A single dose of 40 nM of 3UP8 was sufficient to sustain the increased levels of SMN for five days (FIG. 14B, left panel). Effect on other proteins varied with respect to time. For example, levels of Gemin 2, Gemin 8, ZPR1 and hnRNP Q peaked at day three but started decreasing after that, whereas the levels of Tra2-β1 reached maximum on day three and remained high till day five (FIG. 14B, left panel). As for the effect on exon 7 splicing, levels of exon inclusion remained high for two days followed by a graduate decrease (FIG. 14B, right panel). It is possible that increase in Tra2-β1 and hnRNP Q levels contributed to exon 7 inclusion.

SMA patient cells are usually deficient in SMN-containing in sub-nuclear bodies or gems. To test whether increase in SMN levels can induce its nuclear accumulation in gems, we performed immunofluorescence analysis of 3UP8 treated GM03813 cells. Here F8 was used as a negative control. As shown in FIG. 15, transfection of cells with 3UP8 was accompanied by a profound increase in the number of gems containing SMN. We also observed that 3UP8 but not F8 resulted in increase and redistribution to gems of SMN-interacting protein, ZPR1 (FIG. 15). It is known that ZPR1 is required for accumulation of SMN in these sub-nuclear structures. Our finding that 3UP8 is able to increase the number of gems confirms a proper assembly of SMN in the nucleus. This also marks the first evidence of a stimulatory response by a very short ASO leading to the massive macromolecular reorganization in the nucleus of a patient cell.

SMA is the second most common genetic disorder of children and infants caused by insufficient levels of SMN protein due to the loss of the SMN1 gene. Presence of a defective gene, SMN2, makes SMA a unique genetic disease that could be avoided and possibly cured by redirecting SMN2 exon 7 splicing. Among several approaches to correct aberrant splicing, an ASO-based approach provides a superior alternative due to the anticipated target specificity. Size of an ASO is an important determinant in success of an ASO-based strategy. Despite the expected advantages, it is not known if very short ASOs could anneal to the target and bring desired changes in a sequence-specific manner, particularly at the low nanomolar concentrations.

Here we report an 8-mer ASO (3UP8) as the shortest ASO to correct the aberrant splicing of SMN2 exon 7 in SMA patient cells. To the best of our knowledge, this is the first report in which an 8-mer ASO is able to effectively correct aberrant splicing in a patient cell line. Identification of this ASO was achieved through a systematic approach of ultra-refined antisense microwalk in an intronic region adjacent to the 5' ss of exon 7. The 8-mer ASO exerts its stimulatory effect through binding to a GC-rich sequence (CUGCCAGC) spanning from the $7^{th}$ to $14^{th}$ position of intron 7 (FIG. 11). Underscoring an evolutionary significance, this intronic region is not conserved between human and mice.[42] CUGCCAGC target sequence seems to be highly accessible since low nanomolar concentrations of 3UP8 fully restores SMN2 exon 7 inclusion (Table A). Consistently, the predicted secondary structure puts this target sequence in an internal loop flanked by terminal stem-loop structures (FIG. 11A).[28]

Our ultra-refined antisense microwalk with about 50 ASOs captured relative strength of multiple antisense targets that differed by a single nucleotide. As a consequence, it also revealed positions of high significance, wherein sequestering of the last five residues (CCAGC) of the GC-rich target was found to be absolutely required for the stimulatory response on SMN2 exon 7 inclusion (Table A). Hence CCAGC residues could be considered as the core motif, analogous to the seed sequence of the micro-RNA target.[50] However, unlike microRNAs that require assembly of a RNA-induced silencing complex (RISCs) on an 18-mer or longer sequence, our antisense response is solely based on the short RNA:RNA duplex. Based on the published reports, it is highly unlikely that protein factors could form a stable complex with a short RNA:RNA duplex. However, we cannot rule out the possibility of secondary contacts that might have been affected.

The GC-rich target described here does not resemble any known binding motif of a splicing factor, although, it overlaps with the first five residues of ISS-N1, an intronic element that harbors two putative hnRNP A1 binding sites. The C residue at the first position ($^1$C) of ISS-N1 is not the part of hnRNP A1 motif, yet sequestering of this position was found to be absolutely necessary for the antisense response. Further, several ASOs that did not sequester $^1$C produced an inhibitory effect even though they fully sequestered both hnRNP A1 motifs (data not shown). These results suggest that the stimulatory response of ASOs is a combination of effects not necessarily caused by blocking of hnRNP A1 motifs.

Various mechanisms may account for the stimulatory response exerted by 3UP8. The most obvious among them is the strong target affinity of 3UP8 compared to an inhibitory factor that may transiently interact with the same target during the dynamic process of splicing. It is also possible that the RNA:RNA duplex formed between 3UP8 and the GC-rich target helps bring a subtle change in the RNA structure in the vicinity of the 5' ss. Such a structural change may help improve U1 snRNP recruitment and/or the 5' ss recognition. We have previously shown that recruitment of U1 snRNP at the 5' ss of exon 7 is a limiting step for SMN2 exon 7 inclusion. Our results also suggest that the catalytic core of splicing is not affected by a RNA:RNA duplex formed between an ASO and its target immediately downstream of the U1 snRNA binding site. However, dissociation of ASO from the target sequence through a helicase reaction during the catalytic core formation could not be ruled out. In this scenario, the same antisense will be recycled several times on different SMN2 pre-mRNAs. This is an obvious advantage of short ASOs in an ASO-based therapy because frequency of drug (ASO) administration could be minimized.

Our work underscores the high target specificity of very short ASOs during RNA:RNA interactions. For instance, a single mismatch in the middle of the target caused a drastic decrease in the stimulatory response by 3UP8. On the contrary, longer ASOs tolerated this mismatch mutation due to a large duplex formed between an ASO and the target. Tolerance of mismatched mutations provides an inherent drawback and therapeutic risk associated with longer ASOs. Consistently, high concentrations of a 20-mer ASO (Anti-N1) targeting intron 7 produced an off-target effect on SMN2 exon 3 splicing, whereas identical concentrations of 3UP8 had no effect (FIG. 13C).

Owing to the high target specificity and an efficient antisense response by a short ASO, 3UP8 increased levels of SMN in SMA patient cells. It also restored levels of several key proteins that are generally down regulated in SMA (FIG. 14B). These include factors involved in snRNP biogenesis (Gemin 2 and Gemin 8) and RNA splicing (Tra2-β 1 and hnRNP Q) hnRNP Q proteins have been also implicated in other aspect of RNA metabolism, such as RNA transcription, translation, stability and trafficking. Increase in ZPR1 in 3UP8-treated cells suggests that a short ASO is capable of restoring SMN-interacting factors, reduced expressions of which are associated with the progressive loss of motor neurons. Despite a gradual decrease in the levels of SMN2 exon 7 inclusion after two days, high SMN levels were maintained for five days after single treatment with 40 nM 3UP8. These findings suggest a substantially longer half-life of SMN owing to the stabilization of SMN through association with itself and/or with other factors. Consistent with the restoration of the SMN-interacting partners, 3UP8-treated cells showed increased numbers of sub-nuclear bodies (gems) in the nucleus (FIG. 15).

Currently SMA has no cure, although several small compounds capable of increasing levels of SMN in SMA have been identified.[23] Mechanisms of actions and side effects of these compounds remain unknown. Earlier ASO-based strategies promised high target specificity and focused on large ASOs in the anticipation that small motifs could not be targeted by small ASOs. In general, literature is replete with studies using 15-mer or longer ASOs for modulation of alternative splicing. Our work provides the first evidence of high target specificity for a very short ASO and sets a unique precedence of pathogenic splicing modulation by RNA molecules less than half the size of the most reported ASOs. Compared to large ASOs that carry the inherent risk of partial sequestration of different kinds of small motifs and tolerate mismatch mutations, we show that the stimulatory activity of a small ASO is exclusively dependent upon the perfect match with a single motif that is uniquely located within an accessible region of a negative context. Short ASOs offer additional advantages including low cost of synthesis, ease of chemical modifications, reduced chances of immune response, and higher probability of crossing biological barriers.[58] When promotion of exon inclusion is the goal, a short intronic target brings the desired benefits of non-interference with nuclear export and translation. Hence, our findings represent further advancement towards an ASO-based therapy of SMA and bring a unique perspective to our understanding of splicing regulation of a defective gene associated with a major genetic disease of children and infants.

REFERENCES

1. Xing Y, Lee C. Relating alternative splicing to proteome complexity and genome evolution. Adv Exp Med Biol 2007; 623:36-49.
2. Nilsen T W. The spliceosome: the most complex macromolecular machine in the cell. Bioessays 2003; 25:1147-49.
3. Matlin A J, Moore M J. Spliceosome assembly and composition. Adv Exp Med Biol 2007; 623:14-35.
4. Hertel, K J. Combinatorial control of exon recognition. J Biol Chem 2008; 283:1211-15.
5. Lin S, Fu X D. SR proteins and related factors in alternative splicing. Adv Exp Med Biol 2007, 623: 107-122.
6. Martinez-Contreras R, Cloutier P, Shkreta L, Fisette J F, Revil T, Chabot B hnRNP proteins and splicing control. Adv Exp Med Biol 2007, 623: 123-147.
7. Singh R N. Unfolding the mystery of alternative splicing through a unique method of in vivo selection. Front Biosci 2007; 12: 3263-3272.
8. Chasin L A. Searching for splicing motifs. Adv Exp Med Biol 2007; 623: 85-106.
9. David C J, Manley J L. The search for alternative splicing regulators: new approaches offer a path to a splicing code. Genes Dev 2008; 22:279-85.
10. Wang Z, Burge C B. Splicing regulation: from a parts list of regulatory elements to an integrated splicing code. RNA 2008; 14:802-13.
11. Buratti E, Baralle F E. Influence of RNA secondary structure on the pre-mRNA splicing process. Mol Cell Biol 2004; 24:10505-14.
12. Graveley B R. Mutually exclusive splicing of the insect Dscam pre-mRNA directed by competing intronic RNA secondary structures. Cell 2005; 123:65-73.

13. Singh N N, Singh R N, Androphy E J. Modulating role of RNA structure in alternative splicing of a critical exon in the spinal muscular atrophy genes. Nucleic Acids Res 2007; 35:371-89.
14. Hiller M, Zhang Z, Backofen R, Stamm S. Pre-mRNA secondary structures influence exon recognition. PLoS Genet. 2007; 3:e204.
15. Cooper T A, Wan L, Dreyfuss G. RNA and disease. Cell 2009; 136:777-93.
16. Garcia-Blanco M A 2006. Alternative splicing: therapeutic target and tool. Prog Mol Subcell Biol 2006; 44:47-64.
17. Madsen E C, Morcos P A, Mendelsohn B A, Gitlin J D. In vivo correction of a Menkes disease model using antisense oligonucleotides. Proc Natl Acad Sci USA. 2008; 105: 3909-14.
18. van Deutekom J C, Janson A A, Ginjaar I B, Frankhuizen W S, Aartsma-Rus A, Bremmer-Bout M, den Dunnen J T, Koop K, van der Kooi A J, Goemans N M, de Kimpe S J, Ekhart P F, Venneker E H, Platenburg G J, Verschuuren J J, van Ommen G J. Local dystrophin restoration with antisense oligonucleotide PRO051. N Engl J Med 2008; 357: 2677-86.
19. Bauman J, Jearawiriyapaisarn N, Kole R. Therapeutic potential of splice switching oligonucleotides. Oligonucleotides 2009; 19:1-14.
20. Lefebvre S, Burglen L, Reboullet S, Clermont O, Burlet P, Viollet L, Benichou B, Cruaud C, Millasseau P, Zeviani M, LePaslier D, Frezal F, Cohen D, Weissenbach J, Munnich A, Melki J. Identification and characterization of a spinal muscular atrophy-determining gene. Cell 1995; 80:1-5.
21. Vitte J, Fassier C, Tiziano F D, Dalard C, Soave S, Roblot N, Brahe C, Saugier-Veber P, Bonnefont J P, Melki J. Refined characterization of the expression and stability of the SMN gene products. Am J Pathol 2007; 171:1269-80.
22. Hsieh-Li H M, Chang J G, Jong Y J, Wu M H, Wang N M, Tsai C H, Li H. A mouse model for spinal muscular atrophy. Nat Genet. 2002; 24: 66-70.
23. Wirth B, Brichta L, Hahnen E. Spinal muscular atrophy and therapeutic prospects. Prog Mol Subcell Biol 2006; 44: 109-32.
24. Corcia P, Camu W, Praline J, Gordon P H, Vourch P, Andres C. The importance of the SMN genes in the genetics of sporadic ALS. Amyotroph Lateral Scler 2009; 6:1-5.
25. Turner B J, Parkinson N J, Davies K E, Talbot K. Survival motor neuron deficiency enhances progression in an amyotrophic lateral sclerosis mouse model. Neurobiol Dis. 2009 Mar. 27. PMID: 19332122
26. Gabanella F, Butchbach M E, Saieva L, Carissimi C, Burghes A H, Pellizzoni, L. Ribonucleoprotein assembly defects correlate with spinal muscular atrophy severity and preferentially affect a subset of spliceosomal snRNPs. PLoS. ONE 2007; 2: e921.
27. Zhang Z, Lotti F, Dittmar K, Younis I, Wan L, Kasim M, Dreyfuss G. SMN deficiency causes tissue-specific perturbations in the repertoire of snRNAs and widespread defects in splicing. Cell 2008; 133:585-600.
28. Singh N N, Androphy E J, Singh R N. The regulation and regulatory activities of alternative splicing of the SMN gene. Crit. Rev. Eukaryote Gene Expr 2004; 14:271-85.
29. Singh R N. Evolving concepts on human SMN pre-mRNA splicing. RNA Biol. 2007; 4: 7-10.
30. Kashima T, Rao N, Manley J L. An intronic element contributes to splicing repression in spinal muscular atrophy. Proc Natl Acad Sci USA 2007; 104:3426-31.
31. Scholl R, Marquis J, Meyer K, Schümperli D. Spinal muscular atrophy: position and functional importance of the branch site preceding SMN exon 7. RNA Biol. 2007; 4:34-7.
32. Martins de Araújo M, Bonnal S, Hastings M L, Krainer A R, Valcárcel J. Differential 3' splice site recognition of SMN1 and SMN2 transcripts by U2AF and U2 snRNP. RNA 2009; 15:515-23.
33. Cartegni L, Krainer A R. Disruption of an SF2/ASF-dependent exonic splicing enhancer in SMN2 causes spinal muscular atrophy in the absence of SMN1. Nat Genet. 2002; 30:377-384.
34. Kashima T, Manley J L. A negative element in SMN2 exon 7 inhibits splicing in spinal muscular atrophy. Nat Genet. 2003; 34:460-63.
35. Singh N N, Androphy E J, Singh R N. An extended inhibitory context causes skipping of exon 7 of SMN2 in spinal muscular atrophy. Biochem Biophys Res Commun 2004; 315: 381-88.
36. Cartegni L, Hastings M L, Calarco J A, de Stanchina E, Krainer A R. Determinants of exon 7 splicing in the spinal muscular atrophy genes, SMN1 and SMN2. Am J Hum Genet. 2006; 78:63-77.
37. Singh N N, Androphy E J, Singh R N. In vivo selection reveals combinatorial controls that define a critical exon in the spinal muscular atrophy genes. RNA 2004; 10:1291-305.
38. Hofmann Y, Lorson C L, Stamm S, Androphy E J, Wirth B. Htra2-beta 1 stimulates an exonic splicing enhancer and can restore full-length SMN expression to survival motor neuron 2 (SMN2). Proc Natl Acad Sci USA 2000; 97:9618-23.
39. Hua Y, Vickers T A, Baker B F, Bennett C F, Krainer A R. Enhancement of SMN2 exon 7 inclusion by antisense oligonucleotides targeting the exon. PLoS Biol 2007; 5:e73.
40. Miyajima H, Miyaso H, Okumura M, Kurisu J, Imaizumi K. Identification of a cis-acting element for the regulation of SMN exon 7 splicing. J Biol Chem 2002; 277:23271-77.
41. Miyaso H, Okumura M, Kondo S, Higashide S, Miyajima H, Imaizumi K. An intronic splicing enhancer element in Survival Motor Neuron (SMN) pre-mRNA. J Biol Chem 2003; 278:15825-31.
42. Singh N K, Singh N N, Androphy E J, Singh R N. Splicing of a critical exon of human Survival Motor Neuron is regulated by a unique silencer element located in the last intron. Mol Cell Biol 2006; 26:1333-46.
43. Hua Y, Vickers T A, Okunola H L, Bennett C F, Krainer A R. Antisense masking of an hnRNP A1/A2 intronic splicing silencer corrects SMN2 splicing in transgenic mice. Am J Hum Genet. 2008; 82:834-48.
44. Cartegni L, Krainer A R. Correction of disease-associated exon skipping by synthetic exon-specific activators. Nat Struct Biol 2003; 10:120-25.
45. Skordis L A, Dunckley, M G, Yue B, Eperon I C, Muntoni F. Bifunctional antisense oligonucleotides provide a trans-acting splicing enhancer that stimulates SMN2 gene expression in patient fibroblasts. Proc Natl Acad Sci USA 2003; 100:4114-19.
46. Marquis J, Meyer K, Angehrn L, Kämpfer S S, Rothen-Rutishauser B, Schümperli D. Spinal muscular atrophy: SMN2 pre-mRNA splicing corrected by a U7 snRNA derivative carrying a splicing enhancer sequence. Mol Ther 2007; 15:1479-86.
47. Coady T H, Baughan T D, Shababi M, Passini M A, Lorson C L. Development of a single vector system that enhances trans-splicing of SMN2 transcripts. PLoS. ONE 2008; 3:e3468.

48. Lim S R, Hertel K J. Modulation of survival motor neuron pre-mRNA splicing by inhibition of alternative 3' splice site pairing. J Biol Chem 2001; 276:45476-83.
49. Madocsai C, Lim S R, Geib T, Lam B J, Hertel K J. Correction of SMN2 Pre-mRNA splicing by antisense U7 small nuclear RNAs. Mol Ther 2005; 12:1013-22.
50. Rana T M. Illuminating the silence: understanding the structure and function of small RNAs. Nat Rev Mol Cell Biol 2007; 8:23-36.
51. Gangwani L, Mikrut M, Theroux S, Sharma M, Davis R J. Spinal muscular atrophy disrupts the interaction of ZPR1 with the SMN protein. Nat Cell Biol 2001; 3:376-83.
52. Doran B, Gherbesi N, Hendricks G, Flavell R A, Davis R J, Gangwani L. Deficiency of the zinc finger protein ZPR1 causes neurodegeneration. Proc Natl Acad Sci USA 2006; 103:7471-75.
53. Helmken C, Hofmann Y, Schoenen F, Oprea G, Raschke H, Rudnik-Schöneborn S, Zerres K, Wirth B. Evidence for a modifying pathway in SMA discordant families: reduced SMN level decreases the amount of its interacting partners and Htra2-beta1. Hum Genet. 2003; 114:11-21.
54. Rossoll W, Kröning A K, Ohndorf U M, Steegborn C, Jablonka S, Sendtner M. Specific interaction of Smn, the spinal muscular atrophy determining gene product, with hnRNP—R and gry-rbp/hnRNP-Q: a role for Smn in RNA processing in motor axons. Hum Mol Genet. 2002; 11:93-105.
55. Chen H H, Chang, J G, Lu R M, Peng T Y, Tarn, W Y. The RNA binding protein hnRNP Q modulates the utilization of exon 7 in the survival motor neuron 2 (SMN2) gene. Mol Cell Biol 2008; 28:6929-38.
56. Lefebvre S, Burlet P, Liu Q, Bertrandy S, Clermont O, Munnich A, Dreyfuss G, Melki J. Correlation between severity and SMN protein level in spinal muscular atrophy. Nat Genet. 1997; 16:265-69.
57. Gangwani L, Flavell R A, Davis R J. ZPR1 is essential for survival and is required for localization of the survival motor neurons (SMN) protein to Cajal bodies. Mol Cell Biol 2005; 25:2744-56.
58. Jaeger L B, Banks W A. Transport of antisense across the Blood-brain barrier. In: Methods in Molecular Medicine: Antisense Therapeutics (ed. Phillips, M. I., Humana Press, Totowa, N.J.) 2005; 106:237-51.

TABLE A

Effect of ASOs on skipping of SMN2 exon 7 in SMA type 1 fibroblasts (GM03183). SEQ ID NOS 40-61

| | Intron 7 → | g | u | a | a | g | u | c | u | g | | | | | | | ISSN-N1 | | | | | | | | | | | | | | | | |
|---|---|---|---|---|---|---|---|---|---|---|---|---|---|---|---|---|---|---|---|---|---|---|---|---|---|---|---|---|---|---|---|---|
| | | | | | | | | GC-rich sequence | | | CORE | | | | hnRNP A1 | | | | | | hnRNP A1 | | | | | | | | | | | |
| | Intron Position → | 1 | 2 | 3 | 4 | 5 | 6 | 7 | 8 | 9 | 10 | c | a | g | c | u | a | u | u | a | u | g | a | a | a | g | u | g | a | a | u | |
| No. | ASO Name | | | | | | | | | | | 11 | 12 | 13 | 14 | 15 | 16 | 17 | 18 | 19 | 20 | 21 | 22 | 23 | 24 | 25 | 26 | 27 | 28 | 29 | | |
| | | | | | | | | | | | | | | | | ASO Sequence | | | | | | | | | | | | | | | | |

| No. | ASO Name | ASO Sequence | % Exon Skipping SEQ ID NO: 2 ASO Conc. (nM) | | | | SEQ ID NO: |
|---|---|---|---|---|---|---|---|
| | | | 1 | 10 | 50 | 100 | |
| 1 | Anti-N1 | U A A U A C U U U C A C U U U A | 24 | 19 | 19 | 48 | SEQ ID NO: 4 |
| 2 | F19 | U U A A U A C U U U C A C U U U | 33 | 19 | 8 | 6 | SEQ ID NO: 40 |
| 3 | F18 | U U U A A U A C U U U C A C U U | 34 | 14 | 8 | 8 | SEQ ID NO: 41 |
| 4 | F17 | G U U U A A U A C U U U C A C U | 35 | 15 | 6 | 6 | SEQ ID NO: 42 |
| 5 | F16 | C G U U U A A U A C U U U C A C | 35 | 14 | 8 | 6 | SEQ ID NO: 43 |
| 6 | F15 | C C G U U U A A U A C U U U C A | 39 | 23 | 18 | 6 | SEQ ID NO: 5 |
| 7 | F14 | U C C G U U U A A U A C U U U C | 38 | 15 | 11 | 5 | SEQ ID NO: 12 |
| 8 | F13 | G U C C G U U U A A U A C U U U | 37 | 26 | 10 | 6 | SEQ ID NO: 14 |
| 9 | F12 | U G U C C G U U U A A U A C U U | 49 | 33 | 14 | 9 | SEQ ID NO: 17 |
| 10 | F11 | C U G U C C G U U U A A U A C U | 43 | 36 | 13 | 11 | SEQ ID NO: 20 |
| 11 | F10 | U C U G U C C G U U U A A U A C | 50 | 42 | 19 | 19 | SEQ ID NO: 21 |
| 12 | F9 | U U C U G U C C G U U U A A U A | 46 | 48 | 36 | 36 | |
| 13 | F8 | A U U C U G U C C G U U U A A U | 50 | 44 | 41 | 42 | |
| 14 | F7 | A A U U C U G U C C G U U U A A | 46 | 49 | 49 | 48 | |
| 15 | 1UP15 | C G G U C U G U C C G U U U A | 32 | 28 | 8 | 5 | SEQ ID NO: 6 |
| 16 | 2UP15 | C U G G U C U G U C C G U U U | 37 | 19 | 12 | 7 | SEQ ID NO: 7 |
| 17 | 3UP15 | G C U G G U C U G U C C G U U U | 40 | 25 | 15 | 8 | SEQ ID NO: 8 |
| 18 | L15EX | C A C U U U A A U A C U U U A | 52 | 51 | 50 | 45 | SEQ ID NO: 44 |
| 19 | L13 | C A C U U U A A U A C | 50 | 51 | 47 | 46 | SEQ ID NO: 13 |
| 20 | L12 | U C A C U U U A A U A C | 47 | 41 | 55 | 47 | SEQ ID NO: 45 |
| 21 | L10Ex | A C U A A U A C | 49 | 49 | 48 | 45 | SEQ ID NO: 46 |
| 22 | L9Ex | U A C U A A U A C | 50 | 49 | 49 | 48 | |
| 23 | L8MEx | U A C U A A U A | 50 | 49 | 49 | 48 | |
| 24 | L7 | U A A U A C | 50 | 49 | 49 | 48 | |
| 25 | 1UP14 | C G G U C U G U C C G U U U A A U | 27 | 14 | 6 | 5 | SEQ ID NO: 47 |
| 26 | 1UP13 | C G G U C U G U C C G U U U A A U A C U | 34 | 15 | 7 | 5 | SEQ ID NO: 48 |
| 27 | 1UP12 | A C G G U C U G U C C G U U U A A U A C | 44 | 20 | 8 | 8 | SEQ ID NO: 49 |
| 28 | 1UP11 | A C G G U C U G U C C G U U U A A U A | 51 | 37 | 24 | 20 | SEQ ID NO: 50 |
| 29 | 1UP10 | A C G G U C U G U C C G U U U A A U A C | 50 | 43 | 30 | 26 | SEQ ID NO: 51 |
| 30 | 1UP9 | A C G G U C U G U C C G U U U A A U A C U | 50 | 48 | 31 | 29 | |
| 31 | 1UP8 | A C G G U C U G U C C G U U U A A U A C U U | 50 | 48 | 42 | 37 | |
| 32 | 2UP14 | C U G G U C U G U C C G U U U A A U | 35 | 16 | 6 | 5 | SEQ ID NO: 52 |
| 33 | 2UP13 | C U G G U C U G U C C G U U U A A U A C | 39 | 20 | 7 | 8 | SEQ ID NO: 53 |
| 34 | 2UP12 | C U G G U C U G U C C G U U U A A U A C U | 46 | 35 | 13 | 10 | SEQ ID NO: 54 |
| 35 | 2UP11 | A C U G G U C U G U C C G U U U A A U A | 46 | 34 | 14 | 10 | SEQ ID NO: 55 |
| 36 | 2UP10 | A C U G G U C U G U C C G U U U A A U A C | 54 | 32 | 8 | 7 | SEQ ID NO: 56 |
| 37 | 2UP9 | A C U G G U C U G U C C G U U U A A U A C U | 49 | 37 | 17 | 12 | |
| 38 | 2UP8 | A C U G G U C U G U C C G U U U A A U A C U U | 48 | 48 | 22 | 17 | |
| 39 | 3UP14 | G C U G G U C U G U C C G U U U A A U | 38 | 24 | 7 | 5 | SEQ ID NO: 57 |
| 40 | 3UP13 | G C U G G U C U G U C C G U U U A A U A C | 43 | 28 | 19 | 7 | SEQ ID NO: 58 |
| 41 | 3UP12 | G C U G G U C U G U C C G U U U A A U A C U | 41 | 27 | 11 | 9 | SEQ ID NO: 59 |
| 42 | 3UP11 | G A C U G G U C U G U C C G U U U A A U A | 40 | 25 | 12 | 7 | SEQ ID NO: 60 |
| 43 | 3UP10 | G A C U G G U C U G U C C G U U U A A U A C | 39 | 24 | 15 | 12 | SEQ ID NO: 61 |
| 44 | 3UP9 | G A C U G G U C U G U C C G U U U A A U A C U | 40 | 23 | 10 | 7 | |
| 45 | 3UP8 | G A C U G G U C U G U C C G U U U A A U A C U U | 40 | 21 | 6 | 7 | |
| 46 | 3UP7 | G A C U G G U C U G U C C G U U U A A U A C U U U | 49 | 46 | 42 | 38 | |
| 47 | 3UP6 | G A C U G G U C U G U C C G U U U A A U A C U U U A | 49 | 49 | 49 | 47 | |

Cells were transfected with 1, 10, 50 and 100 nM of ASOs and the total RNA for splicing assay was isolated 24 h post transfection. First 29 residues of intron 7 of human SMN are shown in small-case letters. Numbering starts from position 1 of intron 7. GC-rich sequence is highlighted in pink. Positions of ISS-N1 residues are boxed. Two hnRNP A1 motifs within ISS-N1 are indicated.[43] First five residues of ISS-N1 constitute the core of the antisense target and are marked as "CORE" and highlighted in blue. Sequences of ASOs are shown in large case letters in 3' to 5' direction and are arranged against the target sequence of intron 7. Percentage of SMN2 exon 7 skipping is shown on the right. Values highlighted in blue, green and light green colors represent 10% or less, 25% or less and 40% or less exon 7 skipping, respectively. Values highlighted in tan color represent no appreciable effect on SMN2 exon 7 splicing. Mock transfection (without any ASO) produced 50% of SMN2 exon 7 skipping.

The contents of any patents, patent applications, and references cited throughout this specification are hereby incorporated by reference in their entireties.

Those skilled in the art will recognize, or be able to ascertain using no more than routine experimentation, many equivalents to the specific embodiments of the invention described herein. Such equivalents are intended to be encompassed by the following claims.

What is claimed is:

1. A method of enhancing the level of exon 7-containing SMN2 mRNA relative to exon-deleted SMN2 mRNA in a cell or cell extract, comprising:
contacting the cell or cell extract with an isolated oligonucleotide reagent comprising a nucleotide sequence at least 90% complementary over its entire length to a target region of the sequence 5'-CUGGUGUCCACAGAGGAC-3 (SEQ ID NO:3), wherein said oligonucleotide contains between about 10 nucleotide bases and about 20 nucleotide bases, and said nucleotide sequence is effective to hybridize to at least 10 contiguous bases of said target region, such that the level of exon 7-containing SMN2 mRNA relative to exon-deleted SMN2 mRNA in the cell or cell extract is enhanced.

2. The method of claim 1, wherein the cell or cell extract is a spinal muscular atrophy (SMA) patient-derived neuronal cell, muscle cell or fibroblast, or extract thereof.

3. The method of claim 1, wherein the cell or cell extract is selected from the group consisting of an embryonic stem cell, an embryonic stem cell extract, a neuronal stem cell and a neuronal stem cell extract.

4. A method of enhancing the level of exon 7-containing SMN2 mRNA relative to exon-deleted SMN2 mRNA in an organism, comprising administering to the organism an isolated oligonucleotide reagent comprising a nucleotide sequence at least 90% complementary over its entire length to a target region of the sequence 5'-CUGGUGUCCACAGAGGAC-3' (SEQ ID NO:3), wherein said oligonucleotide contains between about 10 nucleotide bases and about 20 nucleotide bases, and said nucleotide sequence is effective to hybridize to at least 10 contiguous bases of said target region, such that the level of exon 7-containing SMN2 mRNA relative to exon-deleted SMN2 mRNA in the organism extract is enhanced.

5. The method of claim 4, wherein the organism is a mammal.

6. The method of claim 5, wherein the organism is a human.

7. The method of claim 6, wherein the human has spinal muscular atrophy (SMA).

8. A method of treating spinal muscular atrophy (SMA) in a patient, comprising administering to the patient an isolated oligonucleotide reagent comprising a nucleotide sequence at least 90% complementary over its entire length to a target region of the sequence 5'-CUGGUGUCCACAGAGGAC-3' (SEQ ID NO:3), wherein said oligonucleotide contains between about 10 nucleotide bases and about 20 nucleotide bases, and said nucleotide sequence is effective to hybridize to at least 10 contiguous bases of said target region in a dose effective to enhance the level of exon 7-containing SMN2 mRNA relative to exon-deleted SMN2 mRNA in cells of the patient, such that SMA in the patient is treated.

9. A method for inhibiting an SMN2 pre-mRNA intronic splicing silencer site in a cell or cell comprising contacting the cell with an isolated oligonucleotide reagent comprising a nucleotide sequence at least 90% complementary over its entire length to a target region of the sequence 5'-CUGGUGUCCACAGAGGAC-3' (SEQ ID NO:3), wherein said oligonucleotide contains between about 10 nucleotide bases and about 20 nucleotide bases, and said nucleotide sequence is effective to hybridize to at least 10 contiguous bases of said target region, such that the SMN2 intronic splicing silencer site is inhibited.

10. A method of enhancing the level of exon 7-containing SMN2 mRNA relative to exon-deleted SMN2 mRNA in a cell or cell extract, comprising contacting the cell or cell extract with an isolated oligonucleotide reagent comprising a nucleotide sequence at least 90% complementary over its entire length to a target region of the sequence 5'-CUGGUGUCCACAGAGGAC-3" (SEQ ID NO:3), wherein said oligonucleotide contains between about 10 nucleotide bases and about 20 nucleotide bases, and said nucleotide sequence is effective to hybridize to at least 10 contiguous bases of said target region, such that the level of exon 7-containing SMN2 mRNA relative to exon-deleted SMN2 mRNA in the cell or cell extract is enhanced.

11. The method of claim 10, wherein the cell or cell extract is a spinal muscular atrophy (SMA) patient-derived neuronal cell, muscle cell or fibroblast, or extract thereof.

12. The method of claim 10, wherein the cell or cell extract is selected from the group consisting of an embryonic stem cell, an embryonic stem cell extract, a neuronal stem cell and a neuronal stem cell extract.

13. A method of enhancing the level of exon 7-containing SMN2 mRNA relative to exon-deleted SMN2 mRNA in an organism, comprising administering to the organism an isolated oligonucleotide reagent comprising a nucleotide sequence at least 90% complementary over its entire length to a target region of the sequence 5'-CUGGUGUCCACAGAGGAC-3' (SEQ ID NO:3), wherein said oligonucleotide contains between about 10 nucleotide bases and about 20 nucleotide bases, and said nucleotide sequence is effective to hybridize to at least 10 contiguous bases of said target region, such that the level of exon 7-containing SMN2 mRNA relative to exon-deleted SMN2 mRNA in the organism extract is enhanced.

14. The method of claim 13, wherein the organism is a mammal.

15. The method of claim 14, wherein the organism is a human.

16. The method of claim 15, wherein the human has spinal muscular atrophy (SMA).

17. A method of treating spinal muscular atrophy (SMA) in a patient, comprising administering to the patient an isolated oligonucleotide reagent comprising a nucleotide sequence at least 90% complementary over its entire length to a target region of the sequence 5'-CUGGUGUCCACAGAGGAC-3' (SEQ ID NO:3), wherein said oligonucleotide contains between about 10 nucleotide bases and about 20 nucleotide bases, and said nucleotide sequence is effective to hybridize to at least 10 contiguous bases of said target region in a dose effective to enhance the level of exon 7-containing SMN2 mRNA relative to exon-deleted SMN2 mRNA in cells of the patient, such that SMA in the patient is treated.

18. A method for inhibiting an SMN2 pre-mRNA intronic splicing silencer site in a cell or cell comprising contacting the cell with an isolated oligonucleotide reagent comprising a nucleotide sequence at least 90% complementary over its entire length to a target region of the sequence 5'-CUGGUGUCCACAGAGGAC-3' (SEQ ID NO:3), wherein said oligonucleotide contains between about 10 nucleotide bases and about 20 nucleotide bases, and said nucleotide sequence is effective to hybridize to at least 10 contiguous bases of said target region, such that the SMN2 intronic splicing silencer site is inhibited.

\* \* \* \* \*

SEQUENCE LISTING

```
<160> NUMBER OF SEQ ID NOS: 77

<210> SEQ ID NO 1
<211> LENGTH: 15
<212> TYPE: RNA
<213> ORGANISM: Homo sapiens

<400> SEQUENCE: 1
ccagcauuau guuug                                                         15

<210> SEQ ID NO 2
<211> LENGTH: 29
<212> TYPE: RNA
<213> ORGANISM: Homo sapiens

<400> SEQUENCE: 2
guaagucugc cagcauuaug aaagugaau                                          29

<210> SEQ ID NO 3
<211> LENGTH: 18
<212> TYPE: RNA
<213> ORGANISM: Homo sapiens

<400> SEQUENCE: 3
cuggugucca cagaggac                                                      18

<210> SEQ ID NO 4
<211> LENGTH: 20
<212> TYPE: RNA
<213> ORGANISM: Homo sapiens

<400> SEQUENCE: 4
auucacuuuc auaaugcugg                                                    20

<210> SEQ ID NO 5
<211> LENGTH: 15
<212> TYPE: RNA
<213> ORGANISM: Homo sapiens

<400> SEQUENCE: 5
cuuucauaau gcugg                                                         15

<210> SEQ ID NO 6
<211> LENGTH: 15
<212> TYPE: RNA
<213> ORGANISM: Homo sapiens

<400> SEQUENCE: 6
uuucauaaug cuggc                                                         15
```

```
<210> SEQ ID NO 7
<211> LENGTH: 15
<212> TYPE: RNA
<213> ORGANISM: Homo sapiens

<400> SEQUENCE: 7
uucauaaugc uggca                                                        15

<210> SEQ ID NO 8
<211> LENGTH: 15
<212> TYPE: RNA
<213> ORGANISM: Homo sapiens

<400> SEQUENCE: 8
ucauaaugcu ggcag                                                        15

<210> SEQ ID NO 9
<211> LENGTH: 15
<212> TYPE: RNA
<213> ORGANISM: Homo sapiens

<400> SEQUENCE: 9
acuuucauaa ugcug                                                        15

<210> SEQ ID NO 10
<211> LENGTH: 15
<212> TYPE: RNA
<213> ORGANISM: Homo sapiens

<400> SEQUENCE: 10
cacuuucaua augcu                                                        15

<210> SEQ ID NO 11
<211> LENGTH: 15
<212> TYPE: RNA
<213> ORGANISM: Homo sapiens

<400> SEQUENCE: 11
ucacuuucau aaugc                                                        15

<210> SEQ ID NO 12
<211> LENGTH: 14
<212> TYPE: RNA
<213> ORGANISM: Homo sapiens

<400> SEQUENCE: 12
uuucauaaug cugg                                                         14

<210> SEQ ID NO 13
<211> LENGTH: 14
<212> TYPE: RNA
<213> ORGANISM: Homo sapiens

<400> SEQUENCE: 13
cuuucauaau gcug                                                         14

<210> SEQ ID NO 14
<211> LENGTH: 13
<212> TYPE: RNA
<213> ORGANISM: Homo sapiens

<400> SEQUENCE: 14
uucauaaugc ugg                                                          13
```

```
<210> SEQ ID NO 15
<211> LENGTH: 13
<212> TYPE: RNA
<213> ORGANISM: Homo sapiens

<400> SEQUENCE: 15
cuuucauaau gcu                                                      13

<210> SEQ ID NO 16
<211> LENGTH: 13
<212> TYPE: RNA
<213> ORGANISM: Homo sapiens

<400> SEQUENCE: 16
uuucauaaug cug                                                      13

<210> SEQ ID NO 17
<211> LENGTH: 12
<212> TYPE: RNA
<213> ORGANISM: Homo sapiens

<400> SEQUENCE: 17
ucauaaugcu gg                                                       12

<210> SEQ ID NO 18
<211> LENGTH: 12
<212> TYPE: RNA
<213> ORGANISM: Homo sapiens

<400> SEQUENCE: 18
uucauaaugc ug                                                       12

<210> SEQ ID NO 19
<211> LENGTH: 12
<212> TYPE: RNA
<213> ORGANISM: Homo sapiens

<400> SEQUENCE: 19
uuucauaaug cu                                                       12

<210> SEQ ID NO 20
<211> LENGTH: 11
<212> TYPE: RNA
<213> ORGANISM: Homo sapiens

<400> SEQUENCE: 20
cauaaugcug g                                                        11

<210> SEQ ID NO 21
<211> LENGTH: 10
<212> TYPE: RNA
<213> ORGANISM: Homo sapiens

<400> SEQUENCE: 21
auaaugcugg                                                          10

<210> SEQ ID NO 22
<211> LENGTH: 14
<212> TYPE: RNA
<213> ORGANISM: Homo sapiens

<400> SEQUENCE: 22
```

```
uuucauacuu cugg                                                  14

<210> SEQ ID NO 23
<211> LENGTH: 14
<212> TYPE: RNA
<213> ORGANISM: Homo sapiens

<400> SEQUENCE: 23
cuuucauacu ucug                                                  14

<210> SEQ ID NO 24
<211> LENGTH: 14
<212> TYPE: DNA
<213> ORGANISM: Homo sapiens

<400> SEQUENCE: 24
tttcataatg ctgg                                                  14

<210> SEQ ID NO 25
<211> LENGTH: 14
<212> TYPE: DNA
<213> ORGANISM: Homo sapiens

<400> SEQUENCE: 25
ctttcataat gctg                                                  14

<210> SEQ ID NO 26
<211> LENGTH: 50
<212> TYPE: DNA
<213> ORGANISM: Homo sapiens

<400> SEQUENCE: 26
gtggtggtac catggcctct aagtcagagt ctcctaaaga gcccgaacag            50

<210> SEQ ID NO 27
<211> LENGTH: 36
<212> TYPE: DNA
<213> ORGANISM: Homo sapiens

<400> SEQUENCE: 27
ccctccaata aagagcttcc tcagctgttc gggctc                           36

<210> SEQ ID NO 28
<211> LENGTH: 35
<212> TYPE: DNA
<213> ORGANISM: Homo sapiens

<400> SEQUENCE: 28
aggaagctct ttattggagg gttgagcttt gaaac                            35

<210> SEQ ID NO 29
<211> LENGTH: 46
<212> TYPE: DNA
<213> ORGANISM: Homo sapiens

<400> SEQUENCE: 29
ctggtggttg ctcttccgca aaatcttctg ccactgccat agctac                46

<210> SEQ ID NO 30
<211> LENGTH: 10
<212> TYPE: RNA
<213> ORGANISM: Homo sapiens

<400> SEQUENCE: 30
```

-continued uugccuuucu                                                          10

<210> SEQ ID NO 31
<211> LENGTH: 18
<212> TYPE: RNA
<213> ORGANISM: Homo sapiens

<400> SEQUENCE: 31
auuaugaaag ugaaucuu                                                 18

<210> SEQ ID NO 32
<211> LENGTH: 32
<212> TYPE: RNA
<213> ORGANISM: Homo sapiens

<400> SEQUENCE: 32
cauuccuuaa auuaaggagu aagucugcca gc                                 32

<210> SEQ ID NO 33
<211> LENGTH: 40
<212> TYPE: DNA
<213> ORGANISM: Homo sapiens

<400> SEQUENCE: 33
ggaatttaat tcctcattca gacggtcgta atactttcac                         40

<210> SEQ ID NO 34
<211> LENGTH: 19
<212> TYPE: DNA
<213> ORGANISM: Homo sapiens

<400> SEQUENCE: 34
ggccaagact gggaccagg                                                19

<210> SEQ ID NO 35
<211> LENGTH: 20
<212> TYPE: DNA
<213> ORGANISM: Homo sapiens

<400> SEQUENCE: 35
tggtgtcatt tagtgctgct                                               20

<210> SEQ ID NO 36
<211> LENGTH: 26
<212> TYPE: DNA
<213> ORGANISM: Homo sapiens

<400> SEQUENCE: 36
agggccaaga ctgggaccag gaaagg                                        26

<210> SEQ ID NO 37
<211> LENGTH: 24
<212> TYPE: DNA
<213> ORGANISM: Homo sapiens

<400> SEQUENCE: 37
catataatag ccagtatgat agcc                                          24

<210> SEQ ID NO 38
<211> LENGTH: 24
<212> TYPE: DNA
<213> ORGANISM: Homo sapiens

```
<400> SEQUENCE: 38
ctgttccggc gcggcacagg ccag                                       24

<210> SEQ ID NO 39
<211> LENGTH: 24
<212> TYPE: DNA
<213> ORGANISM: Homo sapiens

<400> SEQUENCE: 39
tcactttcat ctgttgaaac ttgg                                       24

<210> SEQ ID NO 40
<211> LENGTH: 19
<212> TYPE: RNA
<213> ORGANISM: Homo sapiens

<400> SEQUENCE: 40
ggucguaaua cuuucacuu                                             19

<210> SEQ ID NO 41
<211> LENGTH: 18
<212> TYPE: RNA
<213> ORGANISM: Homo sapiens

<400> SEQUENCE: 41
ggucguaaua cuuucacu                                              18

<210> SEQ ID NO 42
<211> LENGTH: 17
<212> TYPE: RNA
<213> ORGANISM: Homo sapiens

<400> SEQUENCE: 42
ggucguaaua cuuucac                                               17

<210> SEQ ID NO 43
<211> LENGTH: 16
<212> TYPE: RNA
<213> ORGANISM: Homo sapiens

<400> SEQUENCE: 43
ggucguaaua cuuuca                                                16

<210> SEQ ID NO 44
<211> LENGTH: 15
<212> TYPE: RNA
<213> ORGANISM: Homo sapiens

<400> SEQUENCE: 44
uaauacuuuc acuua                                                 15

<210> SEQ ID NO 45
<211> LENGTH: 12
<212> TYPE: RNA
<213> ORGANISM: Homo sapiens

<400> SEQUENCE: 45
cguaauacuu uc                                                    12

<210> SEQ ID NO 46
<211> LENGTH: 10
<212> TYPE: RNA
<213> ORGANISM: Homo sapiens
```

```
<400> SEQUENCE: 46
cuuucacuua                                                              10

<210> SEQ ID NO 47
<211> LENGTH: 14
<212> TYPE: RNA
<213> ORGANISM: Homo sapiens

<400> SEQUENCE: 47
cggucguaau acuu                                                         14

<210> SEQ ID NO 48
<211> LENGTH: 13
<212> TYPE: RNA
<213> ORGANISM: Homo sapiens

<400> SEQUENCE: 48
cggucguaau acu                                                          13

<210> SEQ ID NO 49
<211> LENGTH: 12
<212> TYPE: RNA
<213> ORGANISM: Homo sapiens

<400> SEQUENCE: 49
cggucguaau ac                                                           12

<210> SEQ ID NO 50
<211> LENGTH: 11
<212> TYPE: RNA
<213> ORGANISM: Homo sapiens

<400> SEQUENCE: 50
cggucguaau a                                                            11

<210> SEQ ID NO 51
<211> LENGTH: 10
<212> TYPE: RNA
<213> ORGANISM: Homo sapiens

<400> SEQUENCE: 51
cggucguaau                                                              10

<210> SEQ ID NO 52
<211> LENGTH: 14
<212> TYPE: RNA
<213> ORGANISM: Homo sapiens

<400> SEQUENCE: 52
acggucguaa uacu                                                         14

<210> SEQ ID NO 53
<211> LENGTH: 13
<212> TYPE: RNA
<213> ORGANISM: Homo sapiens

<400> SEQUENCE: 53
acggucguaa uac                                                          13

<210> SEQ ID NO 54
<211> LENGTH: 12
<212> TYPE: RNA
```

```
<213> ORGANISM: Homo sapiens

<400> SEQUENCE: 54
acggucguaa ua                                                          12

<210> SEQ ID NO 55
<211> LENGTH: 11
<212> TYPE: RNA
<213> ORGANISM: Homo sapiens

<400> SEQUENCE: 55
acggucguaa u                                                           11

<210> SEQ ID NO 56
<211> LENGTH: 10
<212> TYPE: RNA
<213> ORGANISM: Homo sapiens

<400> SEQUENCE: 56
acggucguaa                                                             10

<210> SEQ ID NO 57
<211> LENGTH: 14
<212> TYPE: RNA
<213> ORGANISM: Homo sapiens

<400> SEQUENCE: 57
gacggucgua auac                                                        14

<210> SEQ ID NO 58
<211> LENGTH: 13
<212> TYPE: RNA
<213> ORGANISM: Homo sapiens

<400> SEQUENCE: 58
gacggucgua aua                                                         13

<210> SEQ ID NO 59
<211> LENGTH: 12
<212> TYPE: RNA
<213> ORGANISM: Homo sapiens

<400> SEQUENCE: 59
gacggucgua au                                                          12

<210> SEQ ID NO 60
<211> LENGTH: 11
<212> TYPE: RNA
<213> ORGANISM: Homo sapiens

<400> SEQUENCE: 60
gacggucgua a                                                           11

<210> SEQ ID NO 61
<211> LENGTH: 10
<212> TYPE: RNA
<213> ORGANISM: Homo sapiens

<400> SEQUENCE: 61
gacggucgua                                                             10

<210> SEQ ID NO 62
<211> LENGTH: 16
```

```
<212> TYPE: RNA
<213> ORGANISM: Homo sapiens

<400> SEQUENCE: 62
ccucugugga caccag                                                      16

<210> SEQ ID NO 63
<211> LENGTH: 24
<212> TYPE: DNA
<213> ORGANISM: Homo sapiens

<400> SEQUENCE: 63
tgacatccac tttgcctttc tctc                                             24

<210> SEQ ID NO 64
<211> LENGTH: 25
<212> TYPE: RNA
<213> ORGANISM: Homo sapiens

<400> SEQUENCE: 64
guaagucugc cagaaguaug aaagu                                            25

<210> SEQ ID NO 65
<211> LENGTH: 23
<212> TYPE: RNA
<213> ORGANISM: Homo sapiens

<400> SEQUENCE: 65
guaagucugc agcauuauga aag                                              23

<210> SEQ ID NO 66
<211> LENGTH: 15
<212> TYPE: RNA
<213> ORGANISM: Homo sapiens

<400> SEQUENCE: 66
ugucguaaua cuuuc                                                       15

<210> SEQ ID NO 67
<211> LENGTH: 39
<212> TYPE: RNA
<213> ORGANISM: Homo sapiens

<400> SEQUENCE: 67
guaagucugc cagcauuaug aaagugaauc uuacuuuug                             39

<210> SEQ ID NO 68
<211> LENGTH: 44
<212> TYPE: RNA
<213> ORGANISM: Homo sapiens

<400> SEQUENCE: 68
guaagucuga aaaccagca uuaugaaagu gaaucuuacu uuug                        44

<210> SEQ ID NO 69
<211> LENGTH: 44
<212> TYPE: RNA
<213> ORGANISM: Homo sapiens

<400> SEQUENCE: 69
guaagucugg ggggccagca uuaugaaagu gaaucuuacu uuug                       44

<210> SEQ ID NO 70
```

```
<211> LENGTH: 34
<212> TYPE: RNA
<213> ORGANISM: Homo sapiens

<400> SEQUENCE: 70
guaagucugc cagcauuaug aaagugaauu uuug                                  34

<210> SEQ ID NO 71
<211> LENGTH: 29
<212> TYPE: RNA
<213> ORGANISM: Homo sapiens

<400> SEQUENCE: 71
guaagucugc cagcauuaug aaaguuuug                                        29

<210> SEQ ID NO 72
<211> LENGTH: 20
<212> TYPE: RNA
<213> ORGANISM: Homo sapiens

<400> SEQUENCE: 72
cuggugagaa cgccuagguu                                                  20

<210> SEQ ID NO 73
<211> LENGTH: 30
<212> TYPE: RNA
<213> ORGANISM: Homo sapiens

<400> SEQUENCE: 73
uuaaauuaac uggugagaac gccuagguua                                       30

<210> SEQ ID NO 74
<211> LENGTH: 36
<212> TYPE: RNA
<213> ORGANISM: Homo sapiens

<400> SEQUENCE: 74
cuggugagaa cgccagcauu augaaagccu agguua                                36

<210> SEQ ID NO 75
<211> LENGTH: 45
<212> TYPE: RNA
<213> ORGANISM: Homo sapiens

<400> SEQUENCE: 75
uuaaauuaac uggugagaac gccagcauua ugaaagccua gguua                      45

<210> SEQ ID NO 76
<211> LENGTH: 45
<212> TYPE: RNA
<213> ORGANISM: Homo sapiens

<400> SEQUENCE: 76
uuaaauuaag gaguaagucu gccagcauua ugaaagccua gguua                      45

<210> SEQ ID NO 77
<211> LENGTH: 25
<212> TYPE: RNA
<213> ORGANISM: Homo sapiens

<400> SEQUENCE: 77
guaagucuga cagcauuaug aaagc                                            25
```